United States Patent
Rodgers et al.

(10) Patent No.: US 7,557,196 B2
(45) Date of Patent: Jul. 7, 2009

(54) HGC-1, A GENE ENCODING A MEMBER OF THE OLFACTOMEDIN-RELATED PROTEIN FAMILY

(75) Inventors: Griffin P. Rodgers, Kensington, MD (US); Wen-li Liu, Chicago, IL (US); Jiachang Zhang, Ellicot City, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 661 days.

(21) Appl. No.: 10/497,890

(22) PCT Filed: Dec. 9, 2002

(86) PCT No.: PCT/US02/39148

§ 371 (c)(1),
(2), (4) Date: Jun. 15, 2004

(87) PCT Pub. No.: WO03/050293

PCT Pub. Date: Jun. 19, 2003

(65) Prior Publication Data

US 2005/0155096 A1    Jul. 14, 2005

Related U.S. Application Data

(60) Provisional application No. 60/338,759, filed on Dec. 7, 2001.

(51) Int. Cl.
*C07H 21/04* (2006.01)
(52) U.S. Cl. .................................... 536/23.1
(58) Field of Classification Search ............... 536/23.1; 435/320.1, 325, 252.3
See application file for complete search history.

(56) References Cited

U.S. PATENT DOCUMENTS 5,503,995 A    4/1996   Khudyakov et al. ......... 435/91.1

FOREIGN PATENT DOCUMENTS

WO    WO 99/63088    * 12/1999

OTHER PUBLICATIONS

Overbeek (1994, Transgenic animal technology, pp. 96-98).*
Wall, 1996 Theriogenology, vol. 45, pp. 57-68.*
Houdebine, 1994, J. Biotech. vol. 34, pp. 269-287.*
Kappell, 1992, Current Opinions in Biotechnology, vol. 3, pp. 548-553).*
Cameron, 1997, Molec. Biol. 7, pp. 253-265.*
Niemann, 1997, Transg. Res. 7, pp. 73-75.*
Mullins (1993, Hypertension, vol. 22, pp. 630-633.*
Mullins (1990, Nature, vol. 344, 541-544).*
Hammer (1990, Cell, vol. 63, 1099-1112.*
(Mullins, 1989, EMBO J., vol. 8, pp. 4065-4072.*
Taurog, 1988, Jour. Immunol., vol. 141, pp. 4020-4023).*
Mullins (1996, J. Clin. Invest. vol. 98, pp. S37-S40).*
Jansen, M et al, 1995, Pediatric Res, 37 (6): 681-686.*
Alberts et al. (Molecular Biology of the Cell, 3rd edition, 1994, p. 465).*
Shantz and Pegg (Int J of Biochem and Cell Biol., 1999, vol. 31, pp. 107-122).*
McClean and Hill (Eur J of Cancer, 1993, vol. 29A, pp. 2243-2248).*
Fu et al (EMBO Journal, 1996, vol. 15, pp. 4392-4401.*
Yokota, J et al (Oncogene, 1988,vol. 3, pp. 471-475.*
Orkin and Motulsky, NIH ad hoc committee Dec. 1995.*
Theodore Friedmann (Scientific American Jun. 1997, p. 96-101.*
Inder Verma (Nature Sep. 1997; 389:239-242).*
Rubanyi (Molecular Aspects of Medicine 2001;22:113-142).*
Ross et al., Human Gene Therapy Sep. 1996;7:1781-1790, see p. 1789.*
Abrahmsen et al. "Engineering subtilisin and its substrates for efficient ligation of peptide bonds in aqueous solution." (1991)*Biochemistry*, 30:4151.
Akashi et al. "A clonogenic common myeloid progenitor that gives rise to all myeloid lineages." (2000) *Nature* 404, 193-7.
Alexander, "Thrombopoietin." (1999) *Growth Factors* 17, 13-24.
Clark-Lewis et al. "Chemical synthesis, purification, and characterization of two inflammatory proteins, neutrophil activating peptide 1 (interleukin-8) and neutrophil activating peptide." (1991)*Biochemistry*, 30:3128.
Baggiolini and Clark-Lewis, "Interleukin-8, a chemotactic and inflammatory cytokine." FEBS Lett. Jul. 27, 1992;307(1):97-101.
Clark-Lewis et al., "Structural requirements for interleukin-8 function identified by design of analogs and CXC chemokine hybrids." (1994) *J.Biol.Chem.*, 269:16075.
Cunningham, et al., "Receptor and Antibody Epitopes in Human Growth Hormone Identified by Homolog-Scanning Mutagenesis," *Science*, 243:1330-1336 (1989.
Dawson et al. "Synthesis of Proteins by Native Chemical Ligation," *Science*, 266:776-779 (1994.
deLisle Milton et al. "Techniques in Protein Chemistry IV," Academic Press, New York, pp. 257-267 (1992.
Ferretti, et al., "Total synthesis of a gene for bovine rhodopsin." *Proc. Nat. Acad. Sci.* 83:599-603 (1986).
Kunkel et al. "Rapid and efficient site-specific mutagenesis without phenotypic selection." *Methods Enzymol.* 1987:154:367 (1987).

(Continued)

*Primary Examiner*—Christopher H Yaen
(74) *Attorney, Agent, or Firm*—Ballard Spahr Andrews & Ingersoll, LLP

(57) ABSTRACT

An isolated acid having the sequence of a) SEQ ID NO: 1; b) the sequence of SEQ ID NO: 2; c) the sequence of SEQ ID NO: 3; d) a sequence complementary to any of a), b), or c); or e) a sequence of at least 10 contiguous nucleotides specific for any of a)-d). The invention relates to the identification and characterization of a hitherto unidentified human gene, hGC-1. The protein encoded by hGC-1 appears to be a member of the olfactomedin-related proteins. The invention relates generally to the gene (hGC-1), nucleic acids, cDNA, vectors, polypeptides, protein, antibodies, cells, transgenic animal, and other compositions related to hGC-1. Additionally, primers are provided for identifying hGC-1. The invention further relates to methods of using these compositions, such as diagnosis and treatment of various cancers, and kits comprising these compositions.

16 Claims, 15 Drawing Sheets

OTHER PUBLICATIONS

Ness & Engel "Vintage reds and whites: combinatorial transcription factor utilization in hematopoietic differentiation." (1994) *Curr Opin Genet Dev* 4, 718-24.

Pevny et al., "Development of hematopoietic cells lacking transcription factor GATA-1." *Development.* Jan. 1995;121(1):163-72.

Rajarathnam et al. 1H NMR studies of interleukin 8 analogs: characterization of the domains essential for function. Biochemistry. May 31, 1994;33(21):6623-30.

Schnolzer et al. "Constructing proteins by dovetailing unprotected synthetic peptides: backbone-engineered HIV protease." *Science.* Apr. 10, 1992;256(5054):221-5.

Scott et al. "Requirement of transcription factor PU.1 in the development of multiple hematopoietic lineages." *Science.* Sep. 9, 1994;265(5178):1573-7.

Shinozaki et al. "Upregulation of Reg 1α and GW112 in the epithelium of inflamed colonic mucosa," Gut 2001;48:623-629.

Shivdasani & Orkin, "The transcriptional control of hematopoiesis." *Blood.* May 15, 1996;87(10):4025-39).

Smith, "In vitro mutagenesis" Ann. Rev. Gen., 19:423-462 (1985).

Tidow & Welte, "Advances in understanding postreceptor signaling in response to granulocyte colony-stimulating factor." *Curr Opin Hematol.* May 1997;4(3):171-5.

Wojchowski et al. "Signal transduction in the erythropoietin receptor system." *Exp Cell Res.* Nov. 25, 1999;253(1):143-56.

Zhang et al. "Absence of granulocyte colony-stimulating factor signaling and neutrophil development in CCAAT enhancer binding protein alpha-deficient mice." *Proc Natl Acad Sci* U S A. Jan. 21, 1997;94(2):569-74.).

Zhang et al. "Identification and characterization of a novel member of olfactomedin-related protein family, hGC-1, expressed during myeloid lineage development," Molecular and Clinical Hematology Branch, National Institute of Diabetes, Digestive and Kidney Disease, Molecular Pathogenesis Unit, Surgical Neurology Branch, National Institute of Neurological Disorders and Stroke, National Institutes of Health, Building 10, Room 9N115, 10 Center Drive, Bethesda MD 20892, USA.

Zoller, "New molecular biology methods for protein engineering" *Curr. Opin. Struct. Biol.*, 1:605-610 (1991).

\* cited by examiner

1: Glycophorin A+
2: CD13+
3: CD61+

```
aagatgaggccggcctctcattctcctagccctctgttcttcttgcttgcaagctgcaggggatttggggggatgtgtggacctccaatt                    90
                    M  R  P  G  L  S  F  L  L  A  L  F  F  L  G  Q  A  A  G  D  L  G  D  V  G  P  P  I       29
cccagccccggccttcagctcttccaggtgttgatccagcttcagtcccagctccagtcccagccgcagc                                        180
 P  S  P  G  F  S  S  F  P  G  V  D  S  S  S  F  S  S  S  R  S  G  S  S  S  R  S                             59
ttaggcaggcgggagttctgtcccgtcccagttcacgctccgtgatgaccgtgccagtgcctgtgtcttccctg                                    270
 L  G  G  G  S  V  S  Q  L  F  S (N) F  T  G  S  V  D  D  R  G  T  C  Q  C  S  V  S  L                       89
ccagacacacctttcccgtgacagagtgaactgagctcatgtcttctcagaagtttgagaagaacttccaaa                                      360
 P  D  T  F  P  V  D  R  V  R  L  E  F  T  A  H  V  L  S  Q  K  F  E  K  E  L  S  K                          119
gtgaggaatatgtccaattagtgtgtaaaagaaactgttaacc(N)ltaacctgtccgaattgacatcatgagaaggatacatt                            450
 V  R  E  Y  V  Q  L  I  S (N) L  T  V  R  I  D  I  M  E  K  D  T  I                                         149
tcttacactgaacttgaccagctggatcgagctgtgaggtgaaggagagagaaactagacactgagagacttgagaaaacaatgtc                        540
 S  Y  T  E  L  D  F  E  L  I  K  V  E  V  K  E  M  E  K  L  V  I  Q  L  K  E  S  F  G  G                    179
agctcagaaattgttgaccagctgtgttggtcatgtggtgaacagcagcaaaccgtctctgttgagacacttgagaagctt                              630
 S  S  E  I  V  D  Q  L  E  V  E  I  R (N) M  T  L  L  V  E  K  L  E  T  L  D  K  N  N  V                    209
cttgccattcgccgagaatcgtggctcgaaagagtgtgaggccaagagtgtgaacatcagcaaacaaaggactctgtgg                              720
 L  A  I  R  R  E  I  V  A  L  K  T  K  L  K  E  C  E  A  S  K  D  Q  N  T  P  V  V  H  P                    239
cctcccactccaggagctgctgggtagggattactctcccagcatccaacaaaggactgtatggtgcgccattgaatacagatgggagactg                  810
 P  T  P  G  S  C  G  H  G  G  V  V (N) I  S  K  P  S  V  V  Q  L  N  W  R  G  F  S  Y                       269
ctatatgctgcttgggtgggtaggattactctcccagccatgatttgctctattgtatataatgctcggagagttcgcgccttgacttactggcggagactg        900
 L  Y  G  A  W  G  R  D  Y  S  P  Q  H  P  N  K  G  L  Y  W  V  A  P  L  N  T  D  G  R  L                    299
ttggagtatatagactgtacaacacactgatttgctattgtatataatgctcgagagttgcgatcactatggccaaggtagt                            990
 L  E  Y  R  L  Y  N  T  L  D  D  L  L  Y  I  N  A  R  E  L  R  I  T  Y  G  G  S                             329
ggtacacagtttacaacacaacaacatgtacgtcaacatgtaactgccagagtattgccagagtgttaactgccaagattgct                           1080
 G  T  A  V  Y  N  N  M  Y  N  M  Y  N  T  G  N  I  A  R  V (N) L  T  T  N  T  I  A                          359
```

FIG.2B-1

```
1081  gtgactcaaactctccctaatgctgctataataaccgctttcatatgctaatgttgcttggcaagatattgacttgctgtggatgag  1170
 360  V  T  Q  T  L  P  N  A  A  Y  N  R  F  S  Y  A  N  V  A  W  Q D I D F A V D E         389
1171  aatggattgtgggttattatattcaactgagccagctgtaacatggtagtaatccacacttcaggtgctaaac                1260
 390  N  G  L  W  V  I  Y  S  T  E  A  S  T  G  N  M  V  I  S  K  L (N) D T T L Q V L N     419
1261  acttggtataccaagcagtataaaccatctgcttctaacgcctctcatggtatcgggttctgtatgccaccgtatgaacaccaga   1350
 420  T  W  Y  T  K  Q  Y  K  P  S  A  S  N  A  F  M  V  C  G  V  L  Y  A  T  R  T  M  N  T  R  449
1351  acagagagattttttactattgtgaccagaaactttatgtctataacgatggttacctttctgaattatgatctttctgcagagccc 1440
 450  T  E  E  I  F  Y  Y  D  T  N  T  G  K  E  G  K  L  D  I  V  M  H  K  M  Q  E  K  V  Q   479
1441  agcattaactataaccctttgaccagaaacttttatgtctataacgatggttacctttctgaattatgatctttctgcagagccc   1530
 480  S  I  N  Y  N  P  F  D  Q  K  L  Y  V  Y  N  D  G  Y  L  L  N  Y  D  L  S  V  L  Q  K  P  509
1531  cagtaagctgtttaggagtgtttaggggtgaaagagaaatgtttgttgaaaaatagtcttctccacttactgatatctcaggggtgtct 1620
 510  Q  *                                                                                   511
1621  aaaagtgtgttcattttgcagcaatgtttagtgcatagttctaccacactagagatctagaacattgtcttgattgtggttctct   1710
1711  tggaatcatctgcctcttcaggcgcatttgcaataaagtctgtcagaggttcagagtcagaggtcagagatctagaagtcagaggtcctagt 1800
1801  gaagcctactgtgaggagcttcactagagagcttaaattaggaatcagagagagttaaaaactcagtgcatatgggcgtctaggattcttgta 1890
1891  caggaaatatgcccaatgactagtctcatcatgactagtcctcatcatagcaccactttttttccctcactagatcgagaaaaactctggttaggtag 1980
1981  attaatatctggagctcctcgagggaccaaatctccaactttttttccctcactagtgagtttgtgagagaggccttttatgcattaatttgtacatgca 2070
2071  agtaaatttggcatgcatgtatatcttatatatttatatattgcttttatgcattaatttgtacatgcaccattgtccacattg 2160
2161  aataaatccagaaggatctgtagatgaggcacctgttccaccttgtccaccttactaaagtcagtagaatcagtgcatcctact 2250
2251  tcataacttcctgtccaaggcagctcagagaaagctgcagaggtacaacctgttccaccttgtccaccttgtccaccttgtccaccttactaaagtcagtagaatcagtgcatcctact 2340
2341  ttaaaaaattaatagtttctatgatctagagaactgatctagaaagtgctagcaagtgctagttcattgtttgttatctaataaagacct 2430
2431  tctaggactataagaaaatctgatgtcagttgttgcatgtaattttgccttttgtttaagctgaacttgtaggagaacatgtgcaactat 2520
2521  ggtgtatcagttgttgcatgtaattttgccttttgtttaagctgtagagaattgaaatttaattttttctaggacga                2610
2611  gctatagaaagtctattgagagtatcagtgagtatcagtcagtgcaagttgaaccttggagtgtgatgtgtctgtgcttgaa     2700
2700  tgacttatcatcagtctttctatttttctttctttgattgttcaagtcctagtctatagattggcagttggcagttggcagtttaatgcttacctcccctt 2790
2791  ttaaaataatgattaaaatgtgcttcgaaaaaaaaaaaaaaaaaaaaaaaaa  2849
```

FIG.2B-2

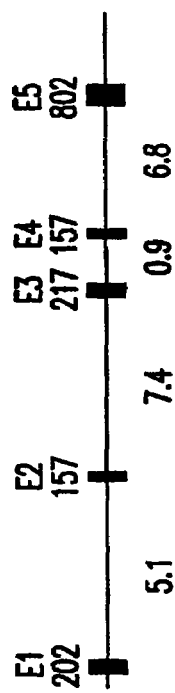
FIG.3A
FIG.3B
FIG.3C

```
OLFACT        1                                                    ---------MYICLLTLV
hGC-1         1   MRPGLSFLLALLFFLGQAAGDLGDVGPPIPSPGFISSFPGVDSSSSFSSSSRSGSSSSRSL
NOELIN-2      1                    ---MQPASKLLTLFFLIL.MGTELTQVLPTNPEESWQVYSSAQDSE
TIGR          1              ---MRFFCARCCSFGPEMPAVQLLLLACLVWDVGARTAQLRKANDQSGRCQYTFSVASP
latrophilin-1 1
consensus     1                                                    :

OLFACT       10   LIHAAAAFVAQNATGILAGKDHCVCEVLLPDSSFPAKRVGALEDETIRLSN..RVEDEMQ
hGC-1        61   GSGGSVSQLFSNFTGSVDDRGTCQCSVSLPDTTFPVDRVERLEFTAHVLSQ..KFEKELS
NOELIN-2     43   GRCICTVVAPQQTM...CSRDARTKQL.....RQLLEKVQNMSQSIEVLD.....RRTQR
TIGR         57   NESSCPEQSQAMSVIHNLQRDSSTQRLDLEATKARLSSLESLLHQL.TLDQAARPQETQE
latrophilin-1 1                                                  ---MA
consensus    61                                                   .   :

OLFACT       68   KLEEQDIILDTYSEKIINLTRRVEYLEKLHPESLVEISFEVLKREIR.ELEMYISAMRVK
hGC-1       119   KVREYVQLISVYEKKLLNLTVRIDIMEK.DTISYTELDFELIKVEVK.EMEKLVIQLKES
NOELIN-2     90   DLQYV........EKMENQMRGLESKF.........KQVEESHKQHLARQFKAIKAKMEEL
TIGR        116   GLQRELGTLRRERDQLETQTRELETAY..SNLLRDKSVLEEKKRLRQENENLARRLESS
latrophilin-1 3   RLAAVLWSLCVTAILVTSATQGLSRAGLPFGLMRRELACEGYPIELRCPGSDVIMENAN
consensus   121       ::                         *             .

OLFACT      127   PNGNSVQVETLYNEVKNMSKTV..GQLETLDKNNVLQAKREIVNLKKRL..VDCEKNLKA
hGC-1       177   FGGSSEIVDQLEVEIRNMTLLV..EKLETLDKNNVLAIRREIVALKTKL..KECEASKDQ
NOELIN-2    134   RPLIPVLE.....EYKADAKLVLQFKEEVQ..NL.TSVLNELQEEIGAYDYEELQNRVSN
TIGR        174   SQEVARLRRGQCPQTRDTARAVPPGSREVSTWNLDTLAFQELKSELTEVPASRILK..ES
latrophilin-1 63  YGRTDDKICDADPFQMENVQCYLPDAFKIMSQRCNNRTQCVVVAGSDAFP.DPCPGTYKY
consensus   181                             :         :              :

FIG. 6B-1
```

```
OLFACT         183  KPSLMVP...LGSCQHQGLAHISKPNLMQLNMKGNAYKSGAWGKDAAWNTTK.KSLYW.V
hGC-1          233  NTPVVHPPPTPGSCGHGGVVNISKPSVVQLNMRGFSYLYGAWGRDYSPQHPN.KGLYW.V
NOELIN-2       186  LEERLRACMQKLAC..GKLTGISDPITIKTS.GS...RFGSWMTD..PLAPEGENKVWYM
TIGR           232  PSGYLRSGEGDTGC..GELVWWGEPLTLRTA.ETITGKYGVWMRDPKPTYPYTQETTWRI
latrophilin-1  122  LEVQYDCVPYIFVCP.GTLQKVLEPTSTHES.E...HQSGAWCKDPLQAGDRIYVMPWI.
consensus      241                                                       *
                         .    *                          .*.*                 *

OLFACT         238  APLNTDGRVLESIRIYPSMSDLQMYKNPIDLPLSMLIKNKLNNTFAGQGAGVVHNNNLY
hGC-1          291  APLNTDGRLLEYYRLYNTLDDLLYINARELRI........TY.GQGSGTAVYNNMY
NOELIN-2       238  DSYHNN.RFVRE...YKSMAD...FMNTDNFTSHRLPHPW......SGTGQVVYNGSIY
TIGR           289  DTVGTDVRQVFE...YDLISQ..FMQGYPSKVHILPRPL......ESTGAVVYSGSLY
latrophilin-1  176  .PYRTDT..LTE...YASWED..YVAARHTTYRLPNRV......DGTGFVVYDGAVF
consensus      301                                                        *
                         .   :    *          :               .**.**    ** :

OLFACT         398  YNCFNSHDMCRASLTSG.VYQKKPLLNALFNNRFSYAGTMFQDMDFSSDEKGLWIFTTE
hGC-1          340  VNMYNTGNIARVNLTTNTIAVTQTLPNAAYNNRFSYANVAWQDIDFAVDENGLWIYSTE
NOELIN-2       284  FNKYQSHIIIRFDLKTETILKTRSLDYAGYNMYHYAWGGHSDIDLMVDENGLWAVYATN
TIGR           336  FQGAESRTVIRYELNTETVKAEKEIPGAGYHGQFPYSWGGYTDIDLAVDEAGLWIYSTD
latrophilin-1  220  YNKERTRNIVKYDLRTRIKSGETVINTANYHDTSPYRMGGKTDIDLAVDENGLWIYSTD
consensus      361                                                       **
                     .  :      .   .  :      ..            .*.***

OLFACT         357  KSAGKIVVGKVNVATFTVDNIWITTQNKSDASNAFMICCGVLYVTRSLGPKME......EV
hGC-1          400  ASTGMVISKLNDTTLQVLNTWYTKQYKPSASNAFMVCGVLYATRTMNTRTE......EI
NOELIN-2       344  QNAGNIVISKLDPNTLQSLQTWNTSYPKRSAGEAFIICGTLYVTNG.Y......SGGTKV
TIGR           396  EAKGAIVLSKLNPENLELEQTWETNIRKQSVANAFIICGTLYTVSS.YT....SADATV
latrophilin-1  280  GNNGRLVVSQLNPYTLRFEGTWETGYDKRSASNAFMVCGVLYLRSVYVDDDSEAAGNRV
consensus      421                                                              .
                              .                 :       *. *.**.  :
```

FIG. 6B-2

| | | |
|---|---|---|
| OLFACT | 411 | FYMFDTKTGKEGHLSIMEKMAEKVHSLSYNSNDRKLYMFSEGYLLLHYDIAL..KP~~~ |
| hGC-1 | 454 | FYYYDTNTGKEGKLDIVMHKMQEKVQSINYNPFDQKLYVVNDGYLLNYDLSVLQKPQ~~~ |
| NOELIN-2 | 397 | HYAYQTNASTYEYIDIPFQNKYSHISMLDYNPKDRALYAWNNGHQILYNVTLFHVIRSDE |
| TIGR | 450 | NFAYDTGTGISKTLTIPFKNRYKYSSMIDYNPLEKKLFAWDNLNMVTYDIKLSKM~~~ |
| latrophilin-1 | 340 | DYAFNTNANREEPVSLAFPNPYQFVSSVDYNPRDNQLYWNNYFVVRYSLEFGPPDPSAG |
| consensus | 481 | ...:.....*.........:**...:*...*...... |

FIG. 6B-3

HGC-1, A GENE ENCODING A MEMBER OF THE OLFACTOMEDIN-RELATED PROTEIN FAMILY

This application claims priority to U.S. application Ser. No. 60/338,759, filed Dec. 7, 2001, which is hereby incorporated in its entirety by this reference.

BACKGROUND OF THE INVENTION

1. Field of the Invention

The present invention is related to the identification and characterization of a hitherto unidentified human gene, hGC-1. The invention relates generally to the gene (hGC-1), nucleotide sequences, vectors, polypeptides, antibodies, and other compositions related to hGC-1. Additionally, primers are provided for identifying hGC-1. The invention further relates to methods of using these compositions, such as diagnosis and treatment of various cancers, and kits comprising these compositions.

2. Background

During the process of hematopoiesis, pluripotent hematopoietic stem cells become committed to one lineage and eventually differentiate into functional, morphologically distinct end-stage cells (Akashi, K., Traver, D., Miyamoto, T. & Weissman, I. L. (2000) *Nature* 404, 193-7). In the bone marrow, pluripotent stem cells differentiate into either the lymphoid stem cell line, where they are further induced to differentiate into B- or T-derived lymphocytes, or the myeloid stem cell (CFU-GEMM) line, where they are further induced to become erythrocytes, granulocytes (neutrophils, eosinophils, or basophils), macrophages, or megakaryocytes (platelets).

Proliferation and differentiation of blood cells in the bone marrow are regulated by hematopoietic factors. Hematopoietic factors that are continuously produced include erythropoietin (EPO), granulocyte colony-stimulating factor (G-CSF) and thrombopoietin (TPO). EPO, G-CSF and TPO bind to their corresponding receptors, thereby inducing tyrosine phosphorylation of a number of cellular proteins and activating specific intracellular signaling cascades, including the signal transducer and activator of transcription (STAT) and mitogen-activated protein kinase (MAPK) pathways (Tidow, N. & Welte, K. (1997) *Curr Opin Hematol* 4, 171-5; Wojchowski, D. M., Gregory, R. C., Miller, C. P., Pandit, A. K. & Pircher, T. J. (1999) *Exp Cell Res* 253, 143-56; Alexander, W. S. (1999) *Growth Factors* 17, 13-24). Differentiation in response to hematopoietic factor signaling is accompanied by coordinate expression of specific genes. However, knowledge about the differences in the signal transduction pathways and gene expression profiles stimulated by these three hematopoietic factors remains limited.

Identification of elements that regulate hematopoietic differentiation and of the genes expressed in response to such regulators is an active area of research. For example, genetic studies in mice have revealed critical lineage-specific roles for transcriptional regulators such as C/EBP (Zhang, D. E., Zhang, P., Wang, N. D., Hetherington, C. J., Darlington, G. J. & Tenen, D. G. (1997) *Proc Natl Acad Sci USA* 94, 569-74), GATA-1 (Pevny, L., Lin, C. S., D'Agati, V., Simon, M. C., Orkin, S. H. & Costantini, F. (1995) *Development* 121, 163-72), PU.1 (Scott, E. W., Simon, M. C., Anastasi, J. & Singh, H. (1994) *Science* 265, 1573-7), and many others (Ness, S. A. & Engel, J. D. (1994) *Curr Opin Genet Dev* 4, 718-24). Elucidation of the genetic alterations underlying certain leukemias, including chromosomal translocations and more subtle mutations, has revealed the hematopoietic functions of proteins such as PLZF and AML-1 (Shivdasani, R. A. & Orkin, S. H. (1996) *Blood* 87, 4025-39).

A mRNA differential display approach was used to examine potentially novel genes associated with hematopoietic lineage commitment and to explore new lineage-specific markers for monitoring lineage differentiation. One of these cDNA fragments derived from differentiation pathways of various lineages was cloned and sequenced. hGC-1 (human G-CSF-stimulated clone-1), is selectively expressed in normal human myeloid lineage cells and is a marker for various cancers.

The following describes the identification and characterization of the hGC-1 gene, its induction properties in hematopoietic cells, and potentially important aspects of its corresponding extracellular protein/glycoprotein structure. Additionally, related compositions and methods for using those compositions are described.

SUMMARY OF THE INVENTION

In accordance with the purpose(s) of this invention, as embodied and broadly described herein, this invention, relates to the identification and characterization of a hitherto unidentified human gene, hGC-1. The protein encoded by hGC-1 appears to be a member of the olfactomedin-related proteins. The invention relates generally to the gene (hGC-1), nucleic acids, cDNA, vectors, polypeptides, protein, antibodies, cells, transgenic animals, and other compositions related to hGC-1. Additionally, primers and probes are provided for identifying hGC-1. The invention further relates to methods of using these compositions, such as diagnosis and treatment of various cancers, and kits comprising these compositions.

The findings of the invention indicate that hGC-1 is primarily expressed as an extracellular olfactomedin-related glycoprotein during normal myeloid-specific lineage differentiation, suggesting the possibility of a matrix-related function for hGC-1 in differentiation. The invention establishes a link between hGC-1 and various cancers, including myeloma, B-cell leukemia, and prostate cancer.

Advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various aspects of the invention and together with the description, serve to explain the principles of the invention.

FIG. 3. Chromosomal localization and gene structure of hGC-1. (A) The gene is shown schematically with its five exons (boxes) and introns (lines). Transcription initiation sites are indicated by arrows. (B) FISH using BAC DNA containing the hGC-1 sequence as a probe. The probe was labeled with digoxigenin and visualized by FITC (red). Fluorescence signals were detected at chromosome 13q14.3 as indicated by arrows. (C) Idiogram of human chromosome 13, illustrating the location of the hGC-1 gene on chromosome band 13q14.3.

DETAILED DESCRIPTION OF THE INVENTION

Figure 1:
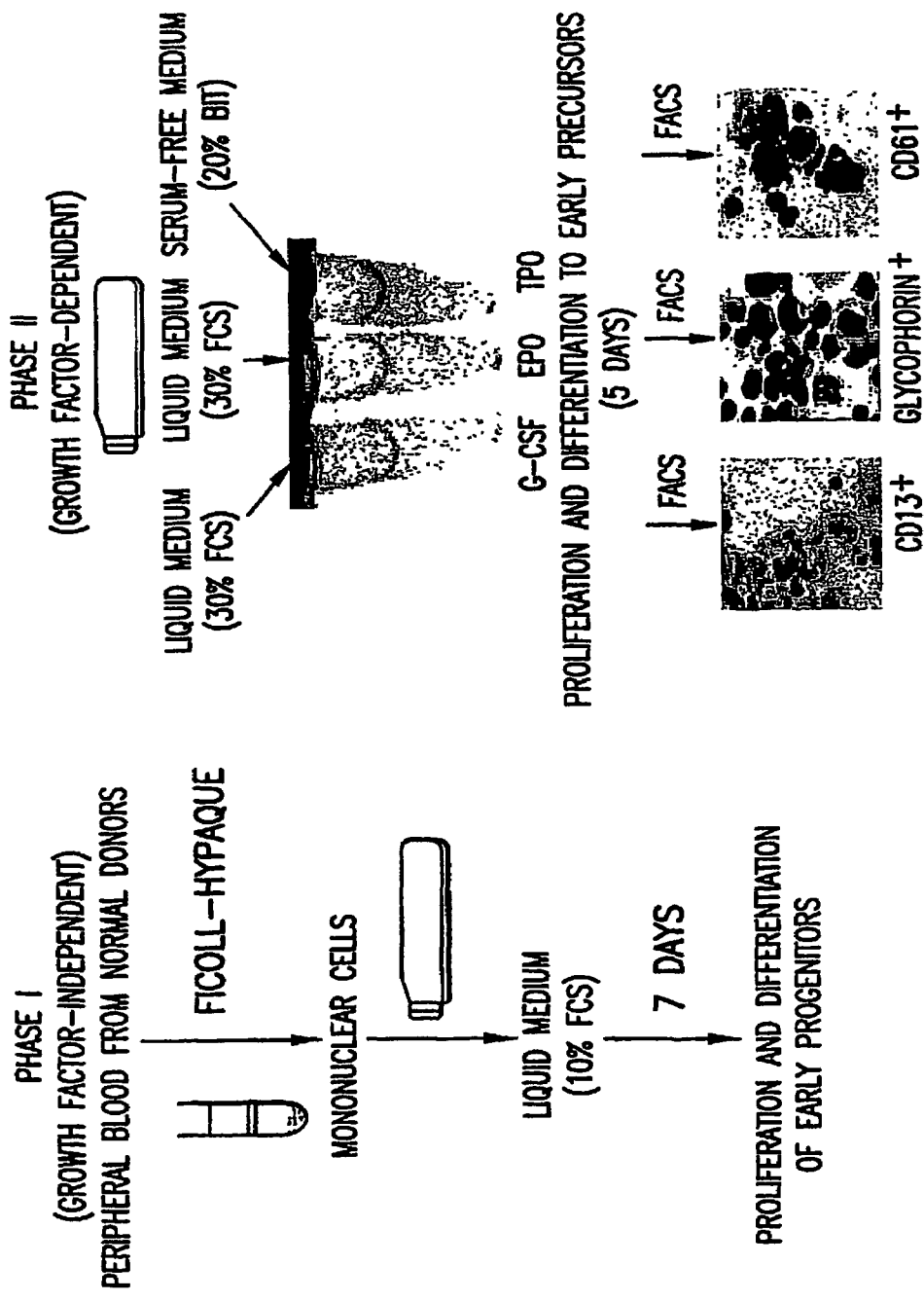
FIG. 1. Overview of the two-phase liquid culture system. Phase I allows for the synchronization, proliferation and differentiation of early (myeloid) stem cell progenitors. Phase II permits lineage-specific proliferation and differentiation under the influence of G-CSF, EPO and TPO. The cells are further enriched by cell sorting (FACS) with lineage-specific markers.

Before the present compounds, compositions, articles, devices, and/or methods are disclosed and described, it is to be understood that this invention is not limited to the specific methods of making and using them, since they may, of course, vary. It is also to be understood that the terminology used herein is for the purpose of describing particular embodiments only and is not intended to be limiting.

Definitions and Use of Terms

It must be noted that, as used in the specification and the appended claims, the singular forms "a," "an" and "the" include plural referents unless the context clearly dictates otherwise. Thus, for example, reference to "a nucleic acid" includes mixtures of nucleic acids, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

By an "effective amount" of a compound as provided herein is meant a sufficient amount of the compound to provide the desired effect. The exact amount required will vary from subject to subject, depending on the species, age, and general condition of the subject, the severity of disease (or underlying genetic defect) that is being treated, the particular compound used, its mode of administration, and the like. Thus, it is not possible to specify an exact "effective amount." However, an appropriate "effective amount" may be determined by one of ordinary skill in the art using only routine experimentation.

By "pharmaceutically acceptable" is meant a material that is not biologically or otherwise undesirable, i.e., the material may be administered to an individual along with the selected compound without causing any undesirable biological effects or interacting in a undesirable manner with any of the other components of the pharmaceutical composition in which it is contained. The carrier may depend on the method of administration and the particular patient.

"hGC-1" refers to the gene or nucleic acid. A hGC-1 gene or nucleic acid refers to any gene or nucleic acid identified with or derived from a wild-type hGC-1 gene. For example, a mutant hGC-1 gene is a form of a hGC-1 gene.

The term "gene" as used herein means a unit of heredity that occupies a specific locus on a chromosome as well as any sequences associated with the expression of that nucleic acid. For example, the gene includes any introns normally present within the coding region as well as regions preceding and following the coding region. Examples of these non-coding regions include, but are not limited to transcription termination regions, promoter regions, enhancer regions and modulation regions. Since the genomic location of the hGC-1 gene is provided herein, the present invention includes any examples of the hGC-1 gene that occur at that locus.

As used herein, the term "nucleic acid" refers to single-or multiple stranded molecules which may be DNA or RNA, or any combination thereof, including modifications to those nucleic acids. The nucleic acid may represent a coding strand or its complement, or any combination thereof. Nucleic acids may be identical in sequence to the sequences which are naturally occurring for any of the novel genes discussed herein, or they may include alternative codons which encode the same amino acid as that which is found in the naturally-occurring sequence. These nucleic acids can also be modified from their typical structure. Such modifications include, but are not limited to, methylated nucleic acids, the substitution of a non-bridging oxygen on the phosphate residue with either a sulfur (yielding phosphorothioate deoxynucleotides), selenium (yielding phosphorselenoate deoxynucleotides), or methyl groups (yielding methylphosphonate deoxynucleotides).

As used herein, the term "specific" refers to having a unique relation to. For example, "species specific" refers to an amino acid or nucleic acid sequence that is found only in a particular species. In another example, "protein/nucleic acid-specific" in the context of a fragment refers to an amino acid or nucleic acid fragment of the referenced protein or nucleic acid that is found only in the referenced protein or nucleic acid.

As used herein, the term "isolated" refers to a nucleic acid separated or significantly free from at least some of the other components of the naturally occurring organism, for example, the cell structural components commonly found associated with nucleic acids in a cellular environment and/or other nucleic acids. The isolation of the native nucleic acids can be accomplished, for example, by techniques such as cell lysis followed by phenol plus chloroform extraction, followed by ethanol precipitation of the nucleic acids. The nucleic acids of this invention can be isolated from cells according to any of many methods well known in the art.

By "isolated nucleic acid" or "purified nucleic acid" is meant DNA that is free of some or all of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, the terms "genomic variant" and "allelic variant" mean a similar gene in another organism of the same species. For example, a nucleic acid from one member of a species can encode a particular hGC-1 protein while another member of the same species has a different nucleic acid which encodes that same hGC-1 protein. A similar gene in another species is defined herein as a "homolog" of a hGC-1 protein. For example, a hGC-1 protein from one species can be different than a hGC-1 protein from another species, yet both may have the same function as the exemplified hGC-1 protein.

By "hGC-1 biological activity" is meant any physiological function attributable to a hGC-1 polypeptide molecule, including signal transduction. hGC-1 biological activity, as referred to herein, is relative to that of the normal hGC-1 polypeptide molecule. It may be desirable to increase or decrease hGC-1 biological activity.

Mechanisms by which a compound may increase hGC-1 biological activity include, but are not limited to, mimicry of endogenous hGC-1 polypeptide activity; stimulation of the activity of a less active or inactive version (for example, a mutant) of the hGC-1 polypeptide; or increasing the amount of hGC-1 polypeptide in a cell (for example, by stimulating hGC-1 transcription and/or translation or by inhibiting hGC-1 mRNA or polypeptide degradation).

hGC-1 biological activity in a sample, such as a cell, tissue, or animal, may be indirectly measured by measuring the relative amount of hGC-1 mRNA (for example, by reverse transcription-polymerase chain reaction (RT-PCR) amplification, ribonuclease protection assay or Northern hybridization); the level of hGC-1 polypeptide (for example, by ELISA or Western blotting); or the activity of a reporter gene under the transcriptional regulation of a hGC-1 transcriptional regulatory region (by reporter gene assay, for example, employing beta-galactosidase, chloramphenicol acetyltransferase (CAT), luciferase, or green fluorescent protein, as is well known in the art). For example, a compound that increases the amount of wild-type hGC-1 polypeptide (or any other version of the polypeptide that maintains at least some activity) in a cell is a compound that increases biological activity of hGC-1.

The terms "peptide", "polypeptide" and "protein" are used interchangeably and as used herein refer to more than one amino acid joined by a peptide bond.

By "hGC-1 polypeptide" is meant a polypeptide that has, or is related to, the amino acid sequence of SEQ ID NO:4. A hGC-1 polypeptide contains an amino acid sequence that bears at least 70% sequence identity, to the amino acid sequence of SEQ ID NO:4.

"Isolated" or "purified" is meant to encompass items, e.g., peptides, which are not naturally occurring, in that they are isolated, purified, synthesized, or otherwise manipulated by man. The isolated or purified peptides, polypeptide, proteins or nucleic acids need not be homogeneous, but must be sufficiently separated from the other components in their naturally environment to allow them to be used for clinical diagnosis or treatment, or for scientific research. By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length polypeptides.

By "wild-type hGC-1 polypeptide" is meant a hGC-1 polypeptide that has normal biological activity, e.g., is produced by a normal subject not suffering from or predisposed to diseases affected by the polypeptide. An example of a wild-type hGC-1 polypeptide is the amino acid sequence of SEQ ID NO:4.

By "wild-type hGC-1 nucleic acid" is meant a nucleic acid that encodes a wild-type hGC-1 polypeptide. Examples of a wild-type hGC-1 nucleic acids include SEQ ID NO:2 and the hGC-1 ORF shown in FIG. 2. Other wild-type hGC-1 nucleic acids include those containing introns, such as genomic hGC-1 nucleic acid, SEQ ID NO:1.

By "polymorphic variant of an hGC-1 polypeptide" is meant an hGC-1 polypeptide containing an amino acid change, relative to wild type, that does not cause disease. Such polymorphic amino acid variations in hGC-1 are seen in both patients and in normal individuals. However, a polymorphic variant, while not the underlying cause of a disease or clinical condition, may subtly increase or decrease hGC-1 biological activity such that hGC-1 is either more efficient or less efficient than that performed by a wild type hGC-1 polypeptide molecule.

By "mutant hGC-1 polypeptide" is meant an hGC-1 polypeptide that prematurely terminates (i.e., is not full length) or that contains an amino acid substitution such that the polypeptide displays less biological activity than the wild type hGC-1 polypeptide, e.g., because it is less stable than the wild type polypeptide (and is thus degraded more rapidly). Examples of mutant hGC-1 polypeptides are those encoded by the genes of patients suffering from cancer or hyperplasia, as described herein.

By "mutated hGC-1 nucleic acid" is meant a nucleic acid that encodes a mutant hGC-1 polypeptide.

By "transfected" or "transformed" is meant an exogenous gene physically introduced into a cell or culture of cells, such that the new nucleic acid is detectable, can be expressed as an RNA or protein, or can be passed on to successive generations.

By "increased susceptibility for developing cancer" is meant a subject who has a greater than normal chance of developing cancer, compared to the general population. Such subjects include, for example, a subject that harbors a mutation in a hGC-1 gene such that biological activity of hGC-1 polypeptide is altered.

By "test compound" is meant a molecule, be it naturally-occurring or artificially derived, that is surveyed for its ability to modulate hGC-1 activity. Test compounds may include, for example, peptides, polypeptides, synthesized organic molecules, naturally occurring organic molecules, nucleic acid molecules, and components thereof.

By "sample" is meant an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g., a polypeptide or nucleic acid), which is assayed as described herein. A sample may also be any body fluid or excretion (for example, but not limited to, blood, urine, stool, saliva, tears, bile) that contains cells or cell components.

By "modulate" is meant to alter, by increase or decrease.

By "normal subject" is meant an individual who does not have an increased susceptibility for developing cancer.

The "subject" or "patient" of this method can be any animal. The animal of the present invention may be a human. In addition, non-human animals which can be treated by the methods of this invention can include, but are not limited to, cats, dogs, birds, horses, cows, goats, sheep, guinea pigs, hamsters, gerbils and rabbits.

By a "transgene" is meant a nucleic acid sequence that is inserted by artifice into a cell and becomes a part of the genome of that cell and its progeny. Such a transgene may be (but is not necessarily) partly or entirely heterologous (for example, derived from a different species) to the cell.

By "transgenic animal" an animal comprising a transgene as described above. Transgenic animals are made by techniques that are well known in the art.

By "knockout mutation" is meant an alteration in the nucleic acid sequence that reduces the biological activity of the polypeptide normally encoded therefrom by at least 80% relative to the unmutated gene. The mutation may, without limitation, be an insertion, deletion, frameshift, or missense mutation. A "knockout animal," for example, a knockout mouse, is an animal containing a knockout mutation. The knockout animal may be heterozygous or homozygous for the knockout mutation. Such knockout animals are generated by techniques that are well known in the art. A form of knockout mutation is one where the biological activity of the hGC-1 polypeptide is not completely eliminated.

By "treat" is meant to administer a compound or molecule of the invention to a subject, such as a human or other mammal (for example, an animal model), that has an increased susceptibility for developing cancer, or that has cancer, in order to prevent or delay a worsening of the effects of the disease or condition, or to partially or fully reverse the effects of the disease.

By "prevent" is meant to minimize the chance that a subject who has an increased susceptibility for developing cancer will develop cancer.

By "specifically binds" is meant that an antibody recognizes and physically interacts with its cognate antigen (for example, a hGC-1 polypeptide) and does not significantly recognize and interact with other antigens; such an antibody may be a polyclonal antibody or a monoclonal antibody, which are generated by techniques that are well known in the art.

By "probe," "primer," or oligonucleotide is meant a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide, and is determined by methods known to one skilled in the art. Probes or primers specific for hGC-1 nucleic acids can (for example, genes and/or mRNAs) have at least 80%, 81%, 82%, 83%, 84%, 85%, 86%, 87%, 88%, 89%, 90%, 91%, 92%, 93%, 94% or 95% sequence complementarity, and should have at least 96%, 97%, 98%, 99% or 100% sequence complementarity, to the region of the hGC-1 nucleic acid to which they hybridize. Probes, primers, and oligonucleotides may be detectably-labeled, either radioactively, or non-radioactively, by methods well-known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

By "specifically hybridizes" is meant that a probe, primer, or oligonucleotide recognizes and physically interacts (that is, base-pairs) with a substantially complementary nucleic acid (for example, a hGC-1 nucleic acid) under high stringency conditions, and does not substantially base pair with other nucleic acids.

By "high stringency conditions" is meant conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1× Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well-known by those skilled in the art of molecular biology. See, for example, F. Ausubel et al., Current Protocols in Molecular Biology, John Wiley & Sons, New York, N.Y., 1998.

By "familial mutation" or "inherited mutation" is meant a mutation in an individual that was inherited from a parent and that was present in somatic cells of the parent. By "sporadic mutation" or "spontaneous mutation" is meant a mutation in an individual that arose in the individual and was not present in a parent of the individual.

The term "cancer," when used herein refers to or describes the physiological condition, such as in a mammalian subject, that is typically characterized by unregulated cell growth. Examples of cancer include but are not limited to myeloma, B-cell leukemia, and prostate cancer. While the term "cancer" as used herein is not limited to any one specific form of the disease, it is believed that the methods of the invention will be particularly effective for cancers which are found to be accompanied by decreased levels of hGC-1 expression.

We have identified and characterized a hematopoietic granulocyte colony-stimulating factor (G-CSF)-induced olfactomedin-related glycoprotein and its corresponding gene, termed hGC-1.

The corresponding protein sequence of hGC-1 indicated that it is a glycoprotein of the olfactomedin family, which includes olfactomedin, TIGR, Noelin-2 and latrophilin-1. Olfactomedin-like genes show characteristic tissue-restricted patterns of expression; the specific tissues that express these genes differ among the various family members. hGC-1 was strongly expressed in the prostate, small intestine, and colon, moderately expressed in the bone marrow and stomach, and not detectable in other tissues. In vitro translation and ex vivo expression showed hGC-1 to be an N-linked glycoprotein. The hGC-1 gene locus mapped to chromosome 13q14.3.

The present data indicate that hGC-1 is primarily expressed as an extracellular olfactomedin-related glycoprotein during normal myeloid-specific lineage differentiation, suggesting the possibility of a matrix-related function for hGC-1 in differentiation.

The present invention provides an isolated nucleic acid encoding a human hGC-1 gene comprising the nucleic acid set forth in the sequence listing SEQ ID NO:1 and described more fully herein infra. Further provided is cDNA clone comprising the sequence SEQ ID NO:2 and described more fully herein infra.

Also provided is a mouse cDNA sequence comprising the sequence SEQ ID NO:3 and described more fully herein infra.

The present invention provides an isolated nucleic acid comprising a) the sequence of SEQ ID NO:1; b) the sequence of SEQ ID NO:2; c) the sequence of SEQ ID NO:3; d) a sequence complementary to any of a), b), or c); and e) a sequence of at least 10 contiguous nucleotides specific for any of a)-d). A nucleic acid comprising one or more of the following structural characteristics: 2849 bp, 5 exons, a polyadenylation signal at bp 2818, an open reading frame of 1530 nucleotides, and having a chromosomal locus of 13q14.3 is disclosed. A nucleic acid comprising an open reading frame (ORF) of approximately 1530 nucleotides that encodes a protein of approximately 510 amino acids is provided. The nucleic acid can be the genomic sequence of hGC-1 (e.g., SEQ ID NO:1) or it can be the cDNA of hGC-1 (e.g., SEQ ID NO:2) or it can be the 1530 nucleotide ORF of hGC-1 disclosed herein.

Figure 4A:
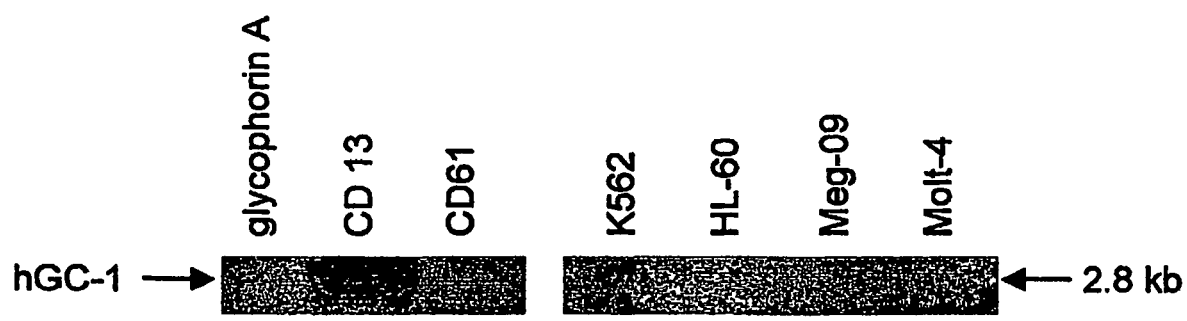
FIG. 4. Northern blot hybridization analysis of hGC-1 expression. Northern blots were hybridized under stringent conditions with uniformly labeled full-length hGC-1 probes, as described in Methods and Materials. Numbers on the right indicate positions of hGC-1 bands. (A) hGC-1 expression in Phase II, day 5, FACS-selected hematopoietic cells and in four leukemia cell lines. (B) Expression of hGC-1 in multiple human tissues was determined by hybridization cDNA probes to Multiple Tissue Northern (MTN™) Blots (Clontech).
Figure 4B:
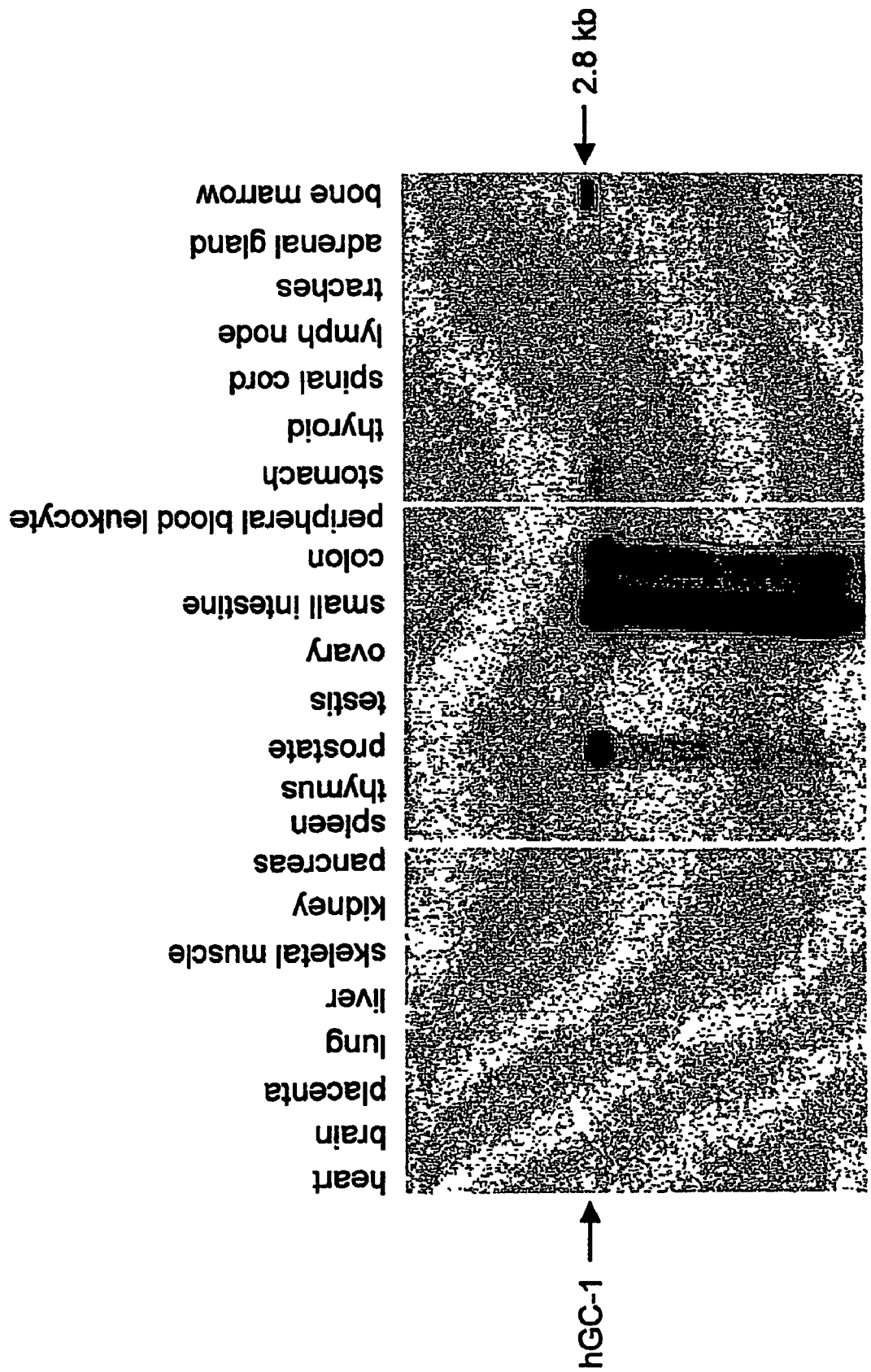

A nucleic acid, defined by a band at about 2.8 KB on a Northern blot, such as depicted in FIG. 4.

A nucleic acid with about 70% or greater homology to the nucleic acid comprising a) the sequence of SEQ ID NO:1; b) the sequence of SEQ ID NO:2; c) the sequence of SEQ ID NO:3; d) a sequence complementary to any of a), b), or c); or e) a sequence of at least 10 contiguous nucleotides specific for any of a)-d) is disclosed. A nucleic acid, which hybridizes to this nucleic acid under stringent conditions is additionally provided.

An isolated nucleic acid comprising a sequence of nucleotides encoding a hGC-1 protein is provided. The hGC-1 protein has the characteristics and structure as described herein, and, for example, can have the an amino acid sequence of SEQ ID NO:4. The nucleic acid can have the sequence of SEQ ID NO:1 or SEQ ID NO:2 or the hGC-1 ORF shown in FIG. 2.

These nucleic acids can be cDNA sequences.

Compositions comprising these nucleic acids are disclosed.

An isolated gene is provided which comprises the nucleic acid of SEQ ID NO: 1, or an allelic variation thereof.

Compositions comprising the gene are disclosed.

Further, the present invention provides products encoded by the nucleic acids or gene of the present invention. These products can be peptides, polypeptides, or proteins. An example of a protein or polypeptide of the present invention is provided in sequence listing SEQ ID NO:4.

A purified protein consisting essentially of the sequence set forth in SEQ ID NO:4, or the sequence set forth in SEQ ID NO:4 having amino acid substitutions which conserve the biological or biochemical or structural properties of the amino acid sequence of SEQ ID NO:4, is disclosed. The amino acid sequence set forth in SEQ ID NO:4 can be a human hGC-1 protein.

A purified polypeptide having one or more of the following characteristics: 510 amino acids, 6 N-linked glycosylation sites (motifs), extracellular protein, member of the olfactomedin family, and lacks a transmembrane domain is disclosed.

A polypeptide encoded by a nucleic acid of the invention can have a deletion in the region encoded by exon 5.

Compositions comprising the products encoded by the gene are disclosed.

A vector comprising the nucleic acid of the invention is disclosed. The vectors are suitable for expressing the nucleic acid. A vector of the present invention expresses human hGC-1 protein in a host cell. The human hGC-1 protein expressed may have the sequence of SEQ ID NO:4.

A cell comprising the vector is given. A cell transfected or transformed by the nucleic acid of the invention is disclosed.

A transgenic animal is disclosed. The transgenic animal comprises a cell that has been transfected with the nucleic acid of the invention.

Further nucleic acids are described herein. These are nucleic acids comprising the sequence of SEQ ID NO:5, SEQ ID NO:6, SEQ ID NO:9, SEQ ID NO:10, SEQ ID NO:11, or SEQ ID NO:12. These nucleic acids can be used as primers. Compositions comprising these nucleic acids are also disclosed.

A purified antibody or fragment thereof, which specifically binds to the polypeptide of the invention is provided. An antibody or fragment thereof of the present invention has binding affinity for an antigenic region of the polypeptide consisting essentially of SEQ ID NO:4 or other polypeptides of the invention.

Compositions comprising the antibody or fragment thereof are disclosed.

A method comprising identifying the expression of hGC-1 in a sample of cells by detecting a nucleic acid specific for the nucleic acid of the invention is provided. Expression of hGC-1 can indicate a cell is of the normal myeloid lineage of cells.

A method is disclosed comprising identifying a patient at increased risk for cancer by measuring the level of hGC-1 in the tissues of the patient that normally expresses hGC-1, and comparing the measured hGC-1 level with hGC-1 levels found in healthy subjects, wherein a decrease in hGC-1 in the patient indicates increased risk.

Also provided is a method of diagnosing cancer comprising detecting a mutation of the hGC-1 gene in suspected cancer cells from a subject.

Further provided is a method of treating cancer comprising administering to a subject a therapeutically effective amount of a non-mutant copy of the gene of the invention, fragment of the gene, nucleic acid of the invention, or polypeptide of the invention to affected cells.

Additionally, a method of preventing cancer in a subject comprising administering a preventative amount of the hGC-1 gene, fragment of the gene, or nucleic acid of the invention to cells of the subject having a mutant copy of the gene is provided.

Still further provided is a method of preventing cancer in a subject comprising administering a preventative amount of a polypeptide of the invention to a subject.

A method of detecting antibodies that bind to hGC-1 in a biological sample is disclosed, comprising the steps of: a) contacting the polypeptide of the invention with the biological sample suspected of containing the polypeptide antibodies under conditions that allow for formation of an antibody-antigen complex; and b) detecting the antibody-antigen complex, whereby the presence of the complex indicates the presence of antibodies that bind to hGC-1.

A method of detecting hGC-1 or an antigenic fragment thereof in a sample is also disclosed, comprising a) contacting the sample with an antibody which selectively binds with the polypeptide of the invention and b) detecting binding of the antibody and antigen, whereby the presence of the complex indicates the presence of antibodies that bind to hGC-1.

The invention discloses a method for detecting the presence of hGC-1 antibodies comprising a) binding an hGC-1 polypeptide to a substrate, b) contacting the bound polypeptide with a sample, c) adding secondary antibodies which bind with the hGC-1 antibodies and which are labeled or bound with a detectable moeity, and d) visualizing the secondary antibody as well.

A method of detecting a mutant hGC-1 gene comprising a) contacting the sample with an antibody which selectively binds with a mutant hGC-1 and b) detecting binding of the antibody and antigen, whereby the presence of the complex indicates the presence of antibodies that bind to a mutant hGC-1 is provided.

The invention also provides kits comprising the compositions of the present invention. Such kits include the following. A kit comprising a packaging, containing the nucleic acid, the polypeptide, or antibodies of the present invention. A kit for amplifying hGC-1 comprising a packaging, containing, separately packaged a forward primer and a reverse primer comprising nucleic acids of the invention are also disclosed. A diagnostic kit for diagnosing cancer or identifying a subject with an increased susceptibility for cancer comprising a packaging, containing, separately packaged reagents for detecting a mutant hGC-1 polypeptide or mutated hGC-1 nucleic acid in the subject are further disclosed.

mRNA differential display analysis was used to identify lineage-specific expressed genes in induced early precursors of blood cell lineages. One clone specifically induced by G-CSF, hGC-1, was further characterized. The corresponding amino acid sequence of hGC-1 indicated that the hGC-1 protein is a glycoprotein of the olfactomedin family. The hGC-1 gene showed tissue-restricted patterns of expression characteristic of the olfactomedin family. hGC-1 was strongly expressed in the prostate, small intestine, and colon, moderately expressed in the bone marrow and stomach, and not detectable in other tissues. In vitro translation and ex vivo expression showed hGC-1 to be an N-linked glycoprotein. The hGC-1 gene locus mapped to chromosome 13q14.3.

The following compositions and methods are provided.

Compositions

The compositions of the present invention include, but are not limited to, the following.

Suitable experimental methods for making the compositions of the invention could be determined by one of ordinary skill in the art. Methods for making specific and preferred compositions of the present invention are described in detail in the Examples below.

Although any methods and materials capable of producing the compositions of the present invention can be used, such as those similar or equivalent to those described herein, in the preparation, practice or testing of the present invention, those methods and materials used to date by the inventors are described herein.

Gene/Nucleic Acids/cDNA

The gene, hGC-1 is provided. An example of an hGC-1 gene is the nucleic acid of SEQ ID NO:1. Allelic variations of hGC-1 are included in this invention. Compositions comprising the gene, or its allelic variants, are also included.

The invention provides isolated nucleic acids that comprise, consist essentially of or consist of the nucleic acids set forth in the Sequence Listing as SEQ ID NO:1 (corresponding to a genomic DNA for an hGC-1 gene, also depicted in FIG. 3A), SEQ ID NO:2 (corresponding to a cDNA encoding a human hGC-1) and SEQ ID NO:3 (corresponding to a nucleic acid encoding a mouse GC-1 cDNA).

The nucleic acids, gene or its allelic variants may be synthesized, isolated, purified, or otherwise made according to methods generally known by one of skill in the art by standard methods. For example, see Sambrook et al., "Molecular Cloning: A Laboratory Manual" 2nd Ed., Cold Spring Harbor Laboratory, Cold Spring Harbor, N.Y. (1989) and Kunkel et al. Methods Enzymol. 1987:154:367 (1987). Compositions comprising the gene, or its variants, may also be made according to methods generally known by one of skill in the art, for example, by simply adding the gene, or its variants, to another composition, such as a carrier. The nucleic acids, gene, or its variants, may likewise be added to other known or yet to be discovered compositions.

Additionally, contemplated by the present invention are nucleic acids, from any desired species, such as mammalian and more specifically human, having 99.9%, 99.7%, 99.5%, 99.3%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall homology or homology in the region being compared to the same region of a nucleic acid set forth in SEQ ID NO:1, SEQ ID NO:2, SEQ ID NO:3 or to a nucleic acid encoding the polypeptide set forth in SEQ ID NO:4, or to allelic variants or homologs thereof. The assessment of homology is preferably based on a base-by-base comparison of the regions being compared. These genes and nucleic acids can be synthesized or obtained by the same methods used to isolate homologs, with stringency of hybridization and washing, if desired, reduced accordingly as homology desired is decreased, and further, depending upon the G-C or A-T richness of any area wherein variability is searched for. Allelic variants of any of the present genes and nucleic acids or of their homologs can readily be isolated and sequenced by screening additional libraries following the examples given herein and procedures well known in the art.

The gene or nucleic acid encoding any selected protein of the present invention can be any nucleic acid that functionally encodes that protein. A nucleic acid encoding a selected protein can readily be determined based upon the amino acid sequence of the selected protein, and, clearly, many nucleic acids will encode any selected protein.

The present invention additionally provides a nucleic acid that selectively hybridizes under stringent conditions with a nucleic acid set forth in SEQ ID NO:1, SEQ ID NO:2, or SEQ ID NO:3. This hybridization can be specific. The degree of complementarity between the hybridizing nucleic acid and the sequence to which it hybridizes should be at least enough to exclude hybridization with a nucleic acid encoding an unrelated protein. Thus, a nucleic acid that selectively hybridizes with a nucleic acid of a present protein coding sequence will not selectively hybridize under stringent conditions with a nucleic acid for a different, unrelated protein, and vice versa. The temperature and salt conditions are readily determined empirically in preliminary experiments in which samples of reference DNA immobilized on filters are hybridized to a labeled nucleic acid of interest and then washed under conditions of different stringencies.

Hybridization temperatures are typically higher for DNA-RNA and RNA-RNA hybridizations. The washing temperatures can be used as described above to achieve selective stringency, as is known in the art. (See, for example, Sambrook et al., "Molecular Cloning: A Laboratory Manual" 2nd Ed., Cold Spring Harbor Laboratory, Cold Spring Harbor, N.Y. (1989) and Kunkel et al. Methods Enzymol. 1987:154: 367 (1987)). Nucleic acid fragments that selectively hybridize to any given nucleic acid can be used, e.g., as primers and or probes for further hybridization or for amplification methods (e.g., polymerase chain reaction (PCR), ligase chain reaction (LCR)).

cDNA of the present invention comprises SEQ ID NO:2 or SEQ ID NO:3. Compositions comprising the cDNA are also included.

The cDNA may be synthesized, isolated, purified, or otherwise obtained according to methods generally known by one of skill in the art. Compositions comprising the cDNA may also be made according to methods generally known by one of skill in the art, for example, by simply adding the cDNA to another composition, such as a carrier. The cDNA may likewise be added to other known or yet to be discovered compositions.

One skilled in the art will appreciate that the cDNA or cDNA fragments (probes, primers etc.) encoding hGC-1 provide information with which the genomic nucleic acids corresponding to this cDNA, or genomic variants of this gene can be isolated. For example, primers for amplifying the hGC-1 gene that encodes the hGC-1 protein can be designed using the sequence information disclosed in SEQ ID NO:1 or 2. Alternatively, those same disclosed nucleic acids can be used to design probes for detecting a nucleic acid containing all or part of the genomic nucleic acid in a genomic library.

The invention includes fragments of the nucleic acids. The fragments may, for example, be probes or primers of expression sequences. For example, the fragments may comprise SEQ ID NO:5, SEQ ID NO:6, SEQ ID NO:9, SEQ ID NO:10, SEQ ID NO:11, or SEQ ID NO:12.

Examples of primers according to the present invention comprise SEQ ID NO:5, SEQ ID NO:6, SEQ ID NO:9, SEQ ID NO:10, SEQ ID NO:11, or SEQ ID NO:12.

Compositions comprising the primers are also included.

The primers may be synthesized or otherwise made according to methods generally known by one of skill in the art. Compositions comprising one of or both of the primers may also be made according to methods generally known by one of skill in the art, for example, by simply adding the primer(s) to another composition, such as a carrier. The primer(s) may likewise be added to other known or yet to be discovered compositions.

The present invention also contemplates polynucleotide probes for detecting a hGC-1 gene, wherein the polynucleotide probe hybridizes to the nucleotide sequence set forth in the Sequence Listing as SEQ ID NO:1, SEQ ID NO:2.

As used herein, the term "polynucleotide probe" refers to a nucleic acid fragment that selectively hybridizes under stringent conditions with a nucleic acid comprising a nucleic acid set forth in a sequence listed herein. This hybridization must be specific. The degree of complementarity between the hybridizing nucleic acid and the sequence to which it hybridizes should be at least enough to exclude hybridization with a nucleic acid encoding an unrelated protein.

Thus, allelic variants can be identified and isolated by nucleic acid hybridization techniques. Probes selective to the nucleic acid set forth in the Sequence Listing as SEQ ID NO:1 or SEQ ID NO:2 can be synthesized and used to probe the nucleic acid from various cells, tissues, libraries etc. High sequence complementarity and stringent hybridization conditions can be selected such that the probe selectively hybridizes to allelic variants of the sequence set forth in the Sequence Listing as SEQ ID NO:1 or SEQ ID NO:2. For example, the selectively hybridizing nucleic acids of the invention can have at least 90%, 91%, 92%, 93%, 94%, 95%, 96%, 97%, 98% and 99% complementarity with the segment of the sequence to which it hybridizes. The nucleic acids can be at least 10, 12, 50, 100, 150, 200, 300, 500, 750, 1000, 1250, 1500, 1750, 2000, 2250, 2500, 2750, 2800, 2849, 2861, or 2870 nucleotides in length. Thus, the nucleic acid can be a coding sequence for a hGC-1 protein or fragments thereof that can be used as a probe or primer for detecting the presence of these genes. If used as primers, the invention provides compositions including at least two nucleic acids which hybridize with different regions so as to amplify a desired region. Several primers are provided below as examples of amplification primers. Depending on the length of the probe or primer, target region can range between 90% complementary bases and full complementarity and still hybridize under stringent conditions. For example, for the purpose of detecting the presence of an allelic variant of the sequence set forth SEQ ID NO:1 or SEQ ID NO:2, the degree of complementarity between the hybridizing nucleic acid (probe or primer) and the sequence to which it hybridizes is at least enough to distinguish hybridization with a nucleic acid from other species. The invention provides examples of nucleic acids unique to SEQ ID NO:1 or SEQ ID NO:2 so that the degree of complementarity required to distinguish selectively hybridizing from nonselectively hybridizing nucleic acids under stringent conditions can be clearly determined for each nucleic acid.

"Stringent conditions" refers to the washing conditions used in a hybridization protocol. In general, the washing conditions should be a combination of temperature and salt concentration chosen so that the denaturation temperature is approximately 5-20° C. below the calculated $T_m$ of the nucleic acid hybrid under study. The temperature and salt conditions are readily determined empirically in preliminary experiments in which samples of reference DNA immobilized on filters are hybridized to the probe or protein coding nucleic acid of interest and then washed under conditions of different stringencies. The $T_m$ of such an oligonucleotide can be estimated by allowing 2° C. for each A or T nucleotide, and 4° C. for each G or C. For example, an 18 nucleotide probe of 50% G+C would, therefore, have an approximate $T_m$ of 54° C.

The present invention also contemplates any unique fragment of the gene or of the nucleic acids set forth in SEQ ID NO:1 or SEQ ID NO:2. To be unique, the fragment must be of sufficient size to distinguish it from other known sequences, most readily determined by comparing any nucleic acid fragment to the nucleotide sequences of nucleic acids in computer databases, such as GenBank. Such comparative searches are standard in the art. Typically, a unique fragment, useful as a primer or probe, will be at least about 20 to about 25 nucleotides in length, depending upon the specific nucleotide content of the sequence. Additionally, fragments can be, for example, at least about 10, 12, 30, 40, 50, 75, 100, 200, 210, 211, 212, 213, 214, 215, 216, 220, 230, 240, 245, 246, 247, 248, 249, 250, 300, 350, 400, 500, 600, 700, 800, 900, 1000, 1250, 1500, 1750, 2000, 2250, 2500, 2750, 2849, 2861 nucleotides in length or any number in between. All of the genes, nucleic acids, and fragments of the genes' and nucleic acids disclosed and contemplated herein can be single or double stranded, depending upon the purpose for which it is intended.

The invention also contemplates compounds comprising the genes, nucleic acids, and fragments of the hGC-1 genes and nucleic acids as disclosed and contemplated herein. For example, a compound comprising a nucleic acid can be a derivative of a typical nucleic acid such as nucleic acids which are modified to contain a terminal or internal reporter molecule and/or those nucleic acids containing non-typical bases or sugars. These reporter molecules include, but are not limited to, isotopic and non-isotopic reporters. Examples include, a FLAG tag or a human IgG Fc. Therefore, any molecule which may aid in detection, amplification, replication, expression, purification, uptake, etc. may be added to the nucleic acid construct.

The genes and nucleic acids provided for by the present invention may be obtained in any number of ways. For example, a DNA molecule encoding a hGC-1 protein can be isolated from the organism in which it is normally found. For example, a genomic DNA or cDNA library can be constructed and screened for the presence of the gene or nucleic acid of interest. Methods of constructing and screening such libraries are well known in the art and kits for performing the construction and screening steps are commercially available (for example, Stratagene Cloning Systems, La Jolla, Calif.). Once isolated, the gene or nucleic acid can be directly cloned into an appropriate vector, or if necessary, be modified to facilitate the subsequent cloning steps. Such modification steps are routine, an example of which is the addition of oligonucleotide linkers which contain restriction sites to the termini of the nucleic acid. General methods are set forth in Sambrook et al., "Molecular Cloning, a Laboratory Manual," Cold Spring Harbor Laboratory Press (1989).

Once the gene or nucleic acid sequence of the desired hGC-1 protein is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type hGC-1 protein coding sequence in order to obtain any of a number of possible combinations of amino acids at any position of the hGC-1 protein. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423-462 (1985) and Zoller, M. J. "New molecular biology methods for protein engineering" Curr. Opin. Struct. Biol., 1:605-610 (1991). Techniques such as these can also be used to modify the genes or nucleic acids in regions other than the coding regions, such as the promoter regions for the hGC-1 protein. Likewise, these techniques can be used to alter the coding sequence without altering the amino acid sequence that is encoded.

Another example of a method of obtaining a DNA molecule encoding a specific hGC-1 protein, polypeptide, or peptide is to synthesize a recombinant DNA molecule which encodes the hGC-1 protein. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330-1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599-603 (1986), wherein synthesis of a 1057 base pair synthetic bovine rhodopsin gene from synthetic oligonucleotides is disclosed. By constructing a hGC-1 protein in this manner, one skilled in the art can readily obtain any particular hGC-1 protein with desired amino acids at any particular position or positions within the hGC-1 protein. See also, U.S. Pat. No. 5,503,995, which describes an enzyme template reaction method of making synthetic genes. Techniques such as this are routine in the art and are well-documented. These nucleic acids or fragments of a nucleic acid encoding a hGC-1 protein can then be expressed in vivo or in vitro as discussed below.

Amino Acid Sequence/Polypeptide/Protein

The invention provides the hGC-1 protein. The amino acid sequence of hGC-1 can correspond to the nucleotide sequence of hGC-1 as described herein. The protein of the present invention comprises the amino acid sequence of SEQ ID NO:4. The invention includes the immature and mature protein or polypeptides. Compositions comprising the protein, amino acid sequence, or polypeptides are also included.

The amino acid sequence, protein, and peptides may be synthesized, isolated, purified, or otherwise obtained according to methods generally known by one of skill in the art. Compositions comprising the amino acid sequence, protein, and peptides may also be made according to methods generally known by one of skill in the art, for example, by simply adding the amino acid sequence, protein, or polypeptide to another composition, such as a carrier. The amino acid sequence, protein, and polypeptide may likewise be added to other known or yet to be discovered compositions, such as other proteins or polypeptides.

FIG. 6 and its corresponding description indicate the predicted secondary structure of the hGC-1 protein and its homology to olfactomedin-related proteins. It is understood that a polypeptide having one or more of the defined secondary structural characteristics is within the scope of the invention. The polypeptide should also possess at least one of the functions of hGC1.

The invention also provides polypeptides encoded by the nucleic acid set forth in SEQ ID NO:1 or SEQ ID NO:2, and the polypeptides set forth the Sequence Listing as SEQ ID NO:4. The invention also provides fragments of unmodified and modified hGC-1 proteins. The fragments can be specific for hGC-1 or specific for the hGC-1 shown in SEQ ID NO:4. The fragments can be at least 5 amino acids long, and any greater length up to one amino acid less than the full-length protein. The polypeptide fragments of the present invention can be recombinant proteins obtained by cloning nucleic acids encoding the polypeptide in an expression system capable of producing the polypeptide fragments thereof. For example, one skilled in the art can determine the active regions of a hGC-1 protein which can interact with another protein and cause a biological effect associated with the hGC-1 protein. In one example, amino acids found to not contribute to either the activity, binding specificity, or other biological effect associated with the hGC-1 protein can be deleted and/or substituted without a loss in the respective activity. The fragments, whether attached to other sequences or not, can also include insertions, deletions, substitutions, or other selected modifications of particular regions or specific amino acid residues, provided the activity of the peptide is not significantly altered or impaired.

The fragments of hGC-1 protein disclosed herein are identified in FIG. 6 by selecting fragments (regions) that are not 100% identical to the region of a related protein. The fragments can exclude the stretch of 223 amino acids in the carboxy terminus of hGC-1 which are highly conserved among other olfactomedin proteins, but, to the extent that there is any region lacking 100% identity, that region can constitute a fragment of the invention.

Further contemplated are polypeptides encoded by fragments of the hGC-1 nucleic acids provided herein. It is noted that the hGC-1 protein fragment and that other examples of hGC-1 and hGC-1 fragments having slightly different sequences may be found in nature using routine protocols or generated by design. Additional fragments of hGC-1 can be identified based on correspondence to functional regions of other previously known members of the olfactomedin family.

By "active fragment" is meant a subpart of a whole hGC-1 protein that exhibits an activity of hGC-1.

The hGC-1 polypeptides of this invention can also be fused to another protein such as alkaline phosphatase for detection methods. This fusion polypeptide can be utilized in an ELISA or Western blot to detect the receptor for hGC-1. The hGC-1-alkaline phosphatase (hGC-1AP) polypeptides of this invention can be used to measure hGC-1 in an ELISA-based assay. For example, plates can be coated with an anti-hGC-1 antibody. Samples can then be added to the plates that contain a given amount of hGC-1AP which will bind to the plates. Therefore, in the absence of antigen, hGC-1AP should bind to the plates and produce the maximal amount of alkaline phosphatase activity. Upon addition of samples containing hGC-1, the antigen may compete with hGC-1AP for the hGC-1 antibody on the plates. The presence of antigen will competitively inhibit the binding of hGC-1AP.

Once the gene or nucleic acid sequence of the desired hGC-1 protein is obtained, the sequence encoding specific amino acids can be modified or changed at any particular amino acid position by techniques well known in the art. For example, PCR primers can be designed which span the amino acid position or positions and which can substitute any amino acid for another amino acid. Then a nucleic acid can be amplified and inserted into the wild-type hGC-1 protein coding sequence in order to obtain any of a number of possible combinations of amino acids at any position of the hGC-1 protein. Alternatively, one skilled in the art can introduce specific mutations at any point in a particular nucleic acid sequence through techniques for point mutagenesis. General methods are set forth in Smith, M. "In vitro mutagenesis" Ann. Rev. Gen., 19:423-462 (1985) and Zoller, M. J. "New molecular biology methods for protein engineering" Curr. Opin. Struct. Biol., 1:605-610 (1991). Techniques such as these can also be used to modify the genes or nucleic acids in regions other than the coding regions, such as the promoter regions for the hGC-1 protein. Likewise, these techniques can be used to alter the coding sequence without altering the amino acid sequence that is encoded.

Another example of a method of obtaining a DNA molecule encoding a specific hGC-1 protein is to synthesize a recombinant DNA molecule which encodes the hGC-1 protein. For example, oligonucleotide synthesis procedures are routine in the art and oligonucleotides coding for a particular protein region are readily obtainable through automated DNA synthesis. A nucleic acid for one strand of a double-stranded molecule can be synthesized and hybridized to its complementary strand. One can design these oligonucleotides such that the resulting double-stranded molecule has either internal restriction sites or appropriate 5' or 3' overhangs at the termini for cloning into an appropriate vector. Double-stranded molecules coding for relatively large proteins can readily be synthesized by first constructing several different double-stranded molecules that code for particular regions of the protein, followed by ligating these DNA molecules together. For example, Cunningham, et al., "Receptor and Antibody Epitopes in Human Growth Hormone Identified by Homolog-Scanning Mutagenesis," Science, 243:1330-1336 (1989), have constructed a synthetic gene encoding the human growth hormone gene by first constructing overlapping and complementary synthetic oligonucleotides and ligating these fragments together. See also, Ferretti, et al., Proc. Nat. Acad. Sci. 82:599-603 (1986), wherein synthesis of a 1057 base pair synthetic bovine rhodopsin gene from synthetic oligonucleotides is disclosed. By constructing a hGC-1 protein in this manner, one skilled in the art can readily obtain any particular hGC-1 protein with desired amino acids at any particular position or positions within the hGC-1 protein. See also, U.S. Pat. No. 5,503,995, which describes an enzyme template reaction method of making synthetic genes. Techniques such as this are routine in the art and are well-documented. These nucleic acids or fragments of a nucleic acid encoding a hGC-1 protein can then be expressed in vivo or in vitro as discussed below.

The hGC-1 polypeptides can be obtained in any of a number of procedures well known in the art. One method of producing a polypeptide is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to a particular protein can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a larger polypeptide. (Grant, "Synthetic Peptides: A User Guide," W. H. Freeman and Co., N.Y. (1992) and Bodansky and Trost, Ed., "Principles of Peptide Synthesis," Springer-Verlag Inc., N.Y. (1993)). Alternatively, the peptide or polypeptide can be independently synthesized in vivo as described above. Once isolated, these independent peptides or polypeptides may be linked to form a larger protein via similar peptide condensation reactions.

For example, enzymatic ligation of cloned or synthetic peptide segments can allow relatively short peptide fragments to be joined to produce larger peptide fragments, polypeptides or whole protein domains (Abrahmsen et al. Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. "Synthesis of Proteins by Native Chemical Ligation," Science, 266:776-779 (1994)). The first step is the chemoselective reaction of an unprotected synthetic peptide-α-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site. Application of this native chemical ligation method to the total synthesis of a protein molecule is illustrated by the preparation of human interleukin 8 (IL-8) (Clark-Lewis et al. FEBS Lett., 307:97 (1987), Clark-Lewis et al., J. Biol. Chem., 269:16075 (1994), Clark-Lewis et al. Biochemistry, 30:3128 (1991), and Rajarathnam et al. Biochemistry, 29:1689 (1994)).

Alternatively, unprotected peptide segments can be chemically linked where the bond formed between the peptide segments as a result of the chemical ligation is an unnatural (non-peptide) bond (Schnolzer et al. Science, 256:221 (1992)). This technique has been used to synthesize analogs of protein domains as well as large amounts of relatively pure proteins with full biological activity (deLisle Milton et al. "Techniques in Protein Chemistry IV," Academic Press, New York, pp. 257-267 (1992)).

Vector/Cells/Cell Line/Transgenic Animal

The invention provides a vector comprising the nucleic acids of the invention. Examples of the vectors of the invention include those comprising the nucleotide sequence of SEQ ID NO:1. SEQ ID NO:2, or SEQ ID NO:3. The vector can further comprise any regulatory elements necessary for expression of the sequence in a cell. Compositions comprising the vector are also included.

The vector may be synthesized or otherwise made according to methods generally known by one of skill in the art Compositions comprising the vector may also be made according to methods generally known by one of skill in the art, for example, by simply adding the vector to another composition, such as a carrier. The vector may likewise be added to other known or yet to be discovered compositions.

The invention also provides for the isolated nucleic acids of SEQ ID NO:1 and SEQ ID NO:2 in a vector suitable for expressing the nucleic acid. Once a nucleic acid encoding a particular hGC-1 protein of interest, or a region of that nucleic acid, is constructed, modified, or isolated, that nucleic acid can then be cloned into an appropriate vector, which can direct the in vivo or in vitro synthesis of that wild-type and/or modified hGC-1 protein. The vector is contemplated to have the necessary functional elements that direct and regulate transcription of the inserted gene, or nucleic acid. These functional elements include, but are not limited to, a promoter, regions upstream or downstream of the promoter, such as enhancers that may regulate the transcriptional activity of the promoter, an origin of replication, appropriate restriction sites to facilitate cloning of inserts adjacent to the promoter, antibiotic resistance genes or other markers which can serve to select for cells containing the vector or the vector containing the insert, RNA splice junctions, a transcription termination region, or any other region which may serve to facilitate the expression of the inserted gene or hybrid gene. (See generally, Sambrook et al.).

The invention includes cells transformed or transfected by a vector of the present invention. The cells may be in vitro or in vivo. The cells may comprise a transgenic animal, such as a mouse. The invention includes a knock-out mouse which can be used to test compositions of the present invention or other compositions related to expression of hGC-1.

The cells may be transformed or transfected by any method known in the art that is capable of transforming or transfecting the chosen cells.

This invention also contemplates producing a selected cell line or a non-human transgenic animal model for the analysis of the function of a gene comprising introducing into an embryonic stem cell a vector having a selectable marker which, when the vector is inserted within a gene, the inserted vector can inhibit the expression of the gene, selecting embryonic stem cells expressing the selectable marker, excising the vector from the embryonic stem cells expressing the selectable marker such that host DNA from the gene is linked to the excised vector, sequencing the host DNA in the excised vector, comparing the sequence of the host DNA to known gene sequences to determine which host DNA is from a gene for which a model for the analysis of the function the gene is desired, selecting the embryonic stem cell containing the inhibited gene for which a model for the analysis of gene function is desired, and forming a cell line or a non-human transgenic animal from the selected embryonic stem cell.

Transgenic animals are provided, which either overproduce the polypeptides of this invention or fail to produce the polypeptides of this invention in a functional form. For example, a transgenic animal which overproduces a hGC-1 of this invention can be produced according to methods well known in the art, whereby a nucleic acid encoding hGC-1 is introduced into embryonic stem cells, at which stage it is incorporated into the germline of the animal, resulting in the production of hGC-1 in the transgenic animal in increased amounts relative to a normal animal of the same species. One skilled in the art can determine if overproduction or underproduction of hGC-1 results in altered characteristics, such as predisposition to prostate cancer. Specifically, it has been shown that the hGC-1 gene is normally expressed in prostate epithelial cells, but not in prostate cancer tissues, nor in samples derived from men with benign prostate hypertrophy (BPH). Furthermore, the gene was not expressed in 4 prostate cancer cell lines (Example 12). The mutation(s) in hGC1 associated with cancer can be used to make a transgenic mouse model of the relevant cancer, for example, to search for anti-cancer drugs. Such a transgenic animal can be used to clarify the process of carcinogenesis from normal to pre-cancerous to cancer, thereby allowing targets for pharmaceutical intervention.

A transgenic animal in which the expression of hGC-1, for example, is tissue specific is also contemplated for this invention. For example, transgenic animals that express or overexpress these genes at specific sites, such as bone marrow, gastrointestinal tract, or genitourinary tract can be produced by introducing a nucleic acid into the embryonic stem cells of the animal, wherein the nucleic acid is under the control of a specific promoter which allows expression of the nucleic acid in specific types of cells (e.g., a bone marrow cell, gastrointestinal tract cell or genitourinary tract cell promoter which allows expression only in those cells). One skilled in the art can determine if a tissue-specific alteration in hGC-1 expression results in altered cancer incidence.

Alternatively, the transgenic animal of this invention can be a "knock out" animal (see, e.g., Willnow et al., 1996), which can be an animal that, for example, normally produces hGC-1 but has been altered to prevent the expression of the animal's nucleic acid which encodes hGC-1, thereby resulting in an animal which does not produce hGC-1 in a functional form. Such an animal may lack the ability to express all of the nucleic acids encoding hGC-1 or the transgenic animal may lack the ability to express some (one or more than one) but not all of the nucleic acids encoding the hGC-1.

For example, the transgenic "knock out" animal of this invention can have the expression of a gene or genes knocked out in specific tissues. This approach obviates viability problems that can be encountered if the expression of a widely expressed gene is completely abolished in all tissues.

There are numerous E. coli (Escherichia coli) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxy-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, et al., "α-Factor-Directed Synthesis and Secretion of Mature Foreign Proteins in *Saccharomyces cerevisiae*." Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The nucleic acid coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or β-galactosidase, used to facilitate purification of the fusion protein by affinity chromatography. The insertion of protease cleavage sites to separate the components of the fusion protein is applicable to constructs used for expression in yeast. Efficient post translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes or nucleic acids in mammalian cells, those similar to those developed for the expression of human gamma-interferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acids in mammalian cells (such as COS-7).

Insect cells also permit the expression of mammalian proteins. Recombinant proteins produced in insect cells with baculovirus vectors undergo post-translational modifications similar to that of wild-type proteins. Briefly, baculovirus vectors useful for the expression of active proteins in insect cells are characterized by insertion of the protein coding sequence downstream of the *Autographica californica* nuclear polyhedrosis virus (AcNPV) promoter for the gene encoding polyhedrin, the major occlusion protein. Cultured insect cells such as *Spodoptera frugiperda* cell lines are transfected with a mixture of viral and plasmid DNAs and the viral progeny are plated. Deletion or insertional inactivation of the polyhedrin gene results in the production of occlusion negative viruses which form plaques that are distinctively different from those of wild-type occlusion positive viruses. These distinctive plaque morphologies allow visual screening for recombinant viruses in which the AcNPV gene has been replaced with a hybrid gene of choice. High quantity expression and production of a hGC-1 protein can also be achieved by transgenic animal technology by which animals can be made to produce hGC-1 in serum, milk, etc. in large amounts.

The invention also provides for the vectors containing the contemplated nucleic acids in a host suitable for expressing the nucleic acids. The vectors containing the nucleic acid segments of interest can be transferred into host cells by well-known methods, which vary depending on the type of cellular host. For example, calcium chloride transformation, transduction, and electroporation are commonly utilized for prokaryotic cells, whereas calcium phosphate, DEAE dextran, or lipofection mediated transfection or electroporation may be used for other cellular hosts.

Alternatively, the genes or nucleic acids of the present invention can be operatively linked to one or more of the functional elements that direct and regulate transcription of the inserted gene as discussed above and the gene or nucleic acid can be expressed. For example, a gene or nucleic acid can be operatively linked to a bacterial or phage promoter and used to direct the transcription of the gene or nucleic acid in vitro. A further example includes using a gene or nucleic acid provided herein in a coupled transcription-translation system where the gene directs transcription and the RNA thereby produced is used as a template for translation to produce a polypeptide. One skilled in the art will appreciate that the products of these reactions can be used in many applications such as using labeled RNAs as probes and using polypeptides to generate antibodies or in a procedure where the polypeptides are being administered to a cell or a subject.

Expression of the gene or nucleic acid, in combination with a vector, can be by either in vivo or in vitro. In vivo synthesis comprises transforming prokaryotic or eukaryotic cells that can serve as host cells for the vector. Alternatively, expression of the gene or nucleic acid can occur in an in vitro expression system. For example, in vitro transcription systems are commercially available which are routinely used to synthesize relatively large amounts of mRNA. In such in vitro transcription systems, the nucleic acid encoding the hGC-1 protein would be cloned into an expression vector adjacent to a transcription promoter. For example, the Bluescript II cloning and expression vectors contain multiple cloning sites which are flanked by strong prokaryotic transcription promoters. (Stratagene Cloning Systems, La Jolla, Calif.). Kits are available which contain all the necessary reagents for in vitro synthesis of an RNA from a DNA template such as the Bluescript vectors. (Stratagene Cloning Systems, La Jolla, Calif.). RNA produced in vitro by a system such as this can then be translated in vitro to produce the desired hGC-1 protein. (Stratagene Cloning Systems, La Jolla, Calif.).

Antibodies/Ligands

The invention includes isolated antibodies or fragments thereof with binding affinity for antigenic region(s) of a polypeptide or nucleic acid of the present invention. Compositions comprising the antibodies are also included.

The antibodies may be isolated, purified, synthesized or otherwise obtained according to methods generally known by one of skill in the art. Compositions comprising the antibodies may also be made according to methods generally known by one of skill in the art, for example, by simply adding the antibodies to another composition, such as a carrier. The antibodies may likewise be added to other known or yet to be discovered compositions, such as other antibodies.

Also provided herein are purified antibodies that selectively or specifically bind to the hGC-1 polypeptides provided and contemplated herein, for example, purified antibodies which selectively or specifically bind to a polypeptide encoded by the nucleic acid set forth in any of SEQ ID NO:1 or SEQ ID NO:2, and purified antibodies which selectively or specifically bind to the polypeptide set forth in SEQ ID NO:4. The antibody (either polyclonal or monoclonal) can be raised to any of the polypeptides provided and contemplated herein, both naturally-occurring and recombinant polypeptides, and immunogenic fragments, thereof. The antibody can be used in techniques or procedures such as diagnostics, treatment, or vaccination. Anti-idiotypic antibodies and affinity-matured antibodies are also considered.

Antibodies against hGC-1 are provided. Antibodies can be raised against the whole hGC-1 molecule or against immunogenic fragments of it.

The purified antibodies of this invention include monoclonal antibodies which can be used for diagnostic or analytical purposes. For example, the monoclonal antibody could be utilized in a clinical testing kit to monitor levels of hGC-1 in human tissues or secretions.

The invention includes ligands that specifically bind to a polypeptide of the present invention. Compositions comprising the ligands are also included.

The ligands may be synthesized or otherwise made according to methods generally known by one of skill in the art. Compositions comprising the ligands may also be made according to methods generally known by one of skill in the art, for example, by simply adding the ligands to another composition, such as a carrier. The ligands may likewise be added to other known or yet to be discovered compositions.

Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al. Bio/Technology, 10:163-167 (1992); Bebbington et al. Bio/Technology, 10:169-175 (1992)). Humanized and chimeric antibodies are also contemplated in this invention. Heterologous antibodies can be made by well-known methods (See, for example, U.S. Pat. Nos. 5,545,806; 5,569,825; 5,625,126; 5,633,425; 5,661,016; 5,770,429; 5,789,650; and 5,814,318).

The specifically binding polypeptide or antibody can interact in a binding reaction, which is determinative of the presence of the protein in a heterogeneous population of proteins and other biologics. Thus, under designated immunoassay conditions, the specified antibodies bound to a particular protein do not bind in a significant amount to other proteins present in the sample. Selective binding to an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

Kits

The invention includes kits comprising the compositions of the present invention. The compositions may be separately packaged and provided in kits for use in various methods, such as the diagnostic method described below.

The present invention provides a kit for detecting the binding of an antibody to the hGC-1 or the hGC-1 receptor, or a fragment thereof. Particularly, the kit can detect the presence of an antigen specifically reactive with the antibody or an immunoreactive fragment thereof. The kit can include an antibody bound to a substrate, a secondary antibody reactive with the antigen and a reagent for detecting a reaction of the secondary antibody with the antigen. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein. The particular reagents and other components included in the diagnostic kits of the present invention can be selected from those available in the art in accord with the specific diagnostic method practiced in the kit. Such kits can be used to detect the binding of the antibody with hGC-1 and hGC-1 receptor, or a fragment thereof, in tissue and fluid samples from a patient.

One skilled in the art will be able to correlate the levels of hGC-1 antigen detected using the methods disclosed herein with a particular stage of the cancer, thus utilizing the detection method for prognostic purposes. The prognostic evaluation can determine what type of anti-cancer therapy to employ at different stages of cancer depending on the amounts of hGC-1 antigen detected in the patient's sample.

Methods

Diagnostic Methods

One method of the present invention is using the nucleic acid of the present invention as a marker for the early stages of myeloid lineage development in hematopoiesis. The method can comprise identifying the presence of the nucleic acid in a sample of cells. The presence of the nucleic acid can signify the cells tested are of myeloid lineage.

We have shown that hGC-1 expression was limited to early granulocytic precursor cells in a two phase liquid culture system. In that study, hGC-1 expression in the multipotent prepromyelocytic cell line HL-60 was observed only after induction of granulocytic differentiation, not monocytic differentiation. 32D is a mouse myeloid progenitor cell line, which can differentiate into granulocytes in response to G-CSF. We found that expression of mGC-1 (mouse GC-1) was detected on day 7 when 32D cells were cultured with G-CSF. Therefore, regulation of hGC-1 expression is under developmental control during granulocytic differentiation.

A method comprising identifying the expression of hGC-1 in a sample of cells by detecting a nucleic acid specific for the nucleic acid of the invention is provided. The detection can occur, for example, via differential display, northern analysis, or RT-PCR. Expression of hGC-1 can indicate a cell is of the normal myeloid lineage of cells.

A method is disclosed comprising identifying a patient at increased risk for cancer by detecting in the patient a mutation in the gene of the invention (or identifying a mutation in the hGC-1 gene to determine whether the patient is at risk for cancer), wherein the presence of a mutation indicates increased risk when compared with the hGC-1 level of a healthy subject, wherein a decrease in the hGC-1 in the patient indicates increased risk. The cancer can be myeloma, B-cell leukemia or prostate cancer; specifically, it can be prostate cancer. The mutation may be in exon 5 of the gene and may be a deletion. In prostate cancer, it is believed that the mutation, which may be a deletion, may be found in exon 5.

In a method of the invention, a mutant hGC-1 polypeptide identified is associated with cancer. Having provided the hGC1 gene and protein, and having shown a connection between mutations and disease, the invention provides a method for identifying any specific cancer in which hGC1 may play a role.

The subject having an increased susceptibility for developing cancer is identified by detecting a mutated hGC-1 nucleic acid in the subject. The mutated hGC-1 nucleic acid may comprise a missense mutation, that is, a mutation that changes a codon specific for one amino acid to a codon specific for another amino acid. The hGC-1 nucleic acid having a sequence associated with cancer may also comprise a nucleic acid sequence having an insertion mutation, where one or more nucleotides are inserted into the wild-type sequence. The mutated hGC-1 nucleic acid may comprise a deletion mutation, where one or more nucleotides are deleted from the wild-type sequence. Such a deletion or insertion mutation may, for example, result in a frameshift mutation, altering the reading frame. Frameshift mutations typically result in truncated (that is, prematurely terminated) hGC-1 polypeptide.

A deletion or insertion mutation may comprise at least one deletion or insertion at an amino acid position of the sequence set forth in SEQ ID NO:4.

The mutant hGC-1 nucleic acid may also comprise a nonsense mutation, that is, a mutation that changes a codon specific for an amino acid to a chain termination codon. Nonsense mutations result in truncated (that is, prematurely terminated) hGC-1 polypeptide.

A nonsense mutation may comprise at least one mutation at an amino acid position of the sequence set forth in SEQ ID NO:4.

The mutated hGC-1 nucleic acid may also comprise a truncation mutation, that is, a mutated hGC-1 nucleic acid which encodes a truncated hGC-1 polypeptide. This may occur where, for example, the hGC-1 nucleic acid has a nonsense mutation.

The mutated hGC-1 nucleic acid may comprise a missense mutation, that is, the mutation can result in a change in a codon such that the mutated codon now encodes a different amino acid. The mutation can result in a polypeptide having a non-conservative substitution at the relevant amino acid residue. One of ordinary skill will readily understand the concept of a "non-conservative substitution." Substitutions such as a charged amino acid for an uncharged amino acid, or an uncharged amino acid for a charged amino acid, or any amino acid in place of a Cys, or visa versa, or any amino acid in place of a Pro, or visa versa, are well known in the art to alter the structure and often the function of a protein. The mutation can also result in reduction or elimination of hGC-1 mRNA production, incorrect or altered processing of hGC-1 RNA, increased hGC-1 RNA instability, or other effects on expression of hGC-1 prior to translation. A mutation, which does not alter the encoded amino acid, can affect RNA production, processing, or function.

A missense mutation may comprise at least one mutation at an amino acid position of the sequence set forth in SEQ ID NO:4.

A non-conservative substitution may comprise at least one substitution at an amino acid position of the sequence set forth in SEQ ID NO:4.

The hGC-1 nucleic acid having a sequence associated with cancer encodes a mutant hGC-1 polypeptide.

For example, the mutant hGC-1 polypeptide having a sequence associated with cancer can comprise at least one mutation at an amino acid position of the sequence set forth in SEQ ID NO:4. The hGC-1 polypeptide can comprise at least one mutation at an amino acid position of the sequence set forth in SEQ ID NO:4.

For example, the hGC-1 polypeptide acid having a sequence associated with cancer may comprise at least one mutation at an amino acid position of the sequence set forth in SEQ ID NO:4.

The hGC-1 polypeptide having a sequence associated with cancer can have a non-conservative amino acid substitution of at least one amino acid residue of a hGC-1 having the amino acid sequence set forth in SEQ ID NO:4.

The mutated hGC-1 nucleic acid and mutant polypeptide that is detected can be from any cause. For example, mutant hGC-1 nucleic acid can be the result of a familial mutation or sporadic mutation.

Also provided is a method of diagnosing cancer comprising detecting a mutation of the hGC-1 gene in suspected cancer cells from a subject. The mutation can be in exon 5.

A method of detecting antibodies that bind to hGC-1 in a biological sample comprising the steps of: a) contacting the polypeptide of the invention with the biological sample suspected of containing the polypeptide antibodies under conditions that allow for formation of an antibody-antigen complex; and b) detecting the antibody-antigen complex, whereby the presence of the complex indicates the presence of antibodies that bind to hGC-1 is disclosed.

A method of detecting hGC-1 or an antigenic fragment thereof in a sample comprising a) contacting the sample with an antibody which selectively binds with the polypeptide of the invention and b) detecting binding of the antibody and antigen, whereby the presence of the complex indicates the presence of antibodies that bind to hGC-1 is also disclosed. The antibody may be a purified antibody or fragment thereof, which specifically binds to the polypeptide encoded by a nucleic acid of the invention.

The invention provides a method for detecting the presence of hGC-1 antibodies comprising a) binding an hGC-1 polypeptide to a substrate, b) contacting the bound polypeptide with a sample, c) adding secondary antibodies which bind with the hGC-1 antibodies and which are labeled or bound with a detectable moeity, and d) visualizing the secondary antibody as well.

A method of detecting a mutant hGC-1 gene comprising a) contacting the sample with an antibody which selectively binds with a mutant hGC-1 and b) detecting binding of the antibody and antigen, whereby the presence of the complex indicates the presence of antibodies that bind to a mutant hGC-1 is provided. The mutant hGC-1 may be associated with disease such as cancer. The cancer can be myeloma, B-cell leukemia or prostate cancer, specifically prostate cancer.

Therapeutic Methods

A method of delivering a normal hGC-1 gene to cells in a cancer patient or repairing the abnormal hGC-1 gene as a preventative for patients at risk for cancer or as a treatment for existing cancer is within the scope of the invention. The cancer may be, for example, myeloma, B-cell leukemia, or prostate cancer.

Further provided is a method of treating cancer, comprising administering to affected cells of a subject a therapeutically effective amount of a non-mutant copy of the gene of the invention, fragment of the gene, nucleic acid of the invention, or polypeptide of the invention. The cancer can be myeloma, B-cell leukemia or prostate cancer. Specifically, the cancer can be prostate cancer.

Additionally, a method of preventing cancer in a subject comprising administering a preventative amount of the hGC-1 gene, fragment of the gene, or nucleic acid of the invention to cells of the subject having a mutant copy of the gene is provided. The subject may not produce the normal polypeptide, produce too little of the normal polypeptide, or produce a mutant of the normal polypeptide.

Still further provided is a method of preventing cancer in a subject comprising administering a preventative amount of a polypeptide of the invention (such as a polypeptide encoded by SEQ ID NO:1; SEQ ID NO:2; SEQ ID NO:3; a sequence complementary to SEQ ID NO:1, SEQ ID NO:2 or SEQ ID NO:3; or a sequence of at least 10 contiguous nucleotides specific for SEQ ID NO:1, SEQ ID NO:2, SEQ ID NO:3 or a sequence complementary to SEQ ID NO:1, SEQ ID NO:2 or SEQ ID NO:3) to a subject. The subject may not produce the normal polypeptide, produce too little of the normal polypeptide, or produce a mutant of the normal polypeptide.

Nucleic Acid Delivery

In the method described herein which includes the introduction of exogenous DNA into the cells of a subject (i.e., gene transduction or transfection), the nucleic acids of the present invention can be in the form of naked DNA or the nucleic acids can be in a vector for delivering the nucleic acids to the cells for expression of the nucleic acid inside the cell. For example, hGC-1 biological activity can be stimulated (or correct activity provided) in a subject by administering to the subject a nucleic acid encoding hGC-1, using any method known for nucleic acid delivery into the cells of a subject. The hGC-1 nucleic acid is taken up by the cells of the subject and directs expression of the encoded hGC-1 in those cells that have taken up the nucleic acid. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN®, LIPOFECTAMINE® (GIBCO-BRL, Inc., Gaithersburg, Md.), SUPERFECT® (Qiagen, Inc. Hilden, Germany) and TRANSFECTAM® (Promega Biotec, Inc., Madison, Wis.), as well as other liposomes developed according to procedures standard in the art. In addition, the nucleic acid or vector of this invention can be delivered in vivo by electroporation, the technology for which is available from Genetronics, Inc. (San Diego, Calif.) as well as by means of a SONOPORATION® machine (ImaRx Pharmaceutical Corp., Tucson, Ariz.).

As one example, vector delivery can be via a viral system, such as a retroviral vector system which can package a recombinant retroviral genome (see e.g., Pastan et al., Proc. Natl. Acad. Sci. U.S.A. 85:4486, 1988; Miller et al., Mol. Cell. Biol. 6:2895, 1986). The recombinant retrovirus can then be used to infect and thereby deliver to the infected cells a nucleic acid that encodes a hGC-1 polypeptide. The exact method of introducing the altered nucleic acid into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naidini et al., Science 272:263-267, 1996), pseudotyped retroviral vectors (Agrawal et al., Exper. Hematol. 24:738-747, 1996). Physical transduction techniques can also be used, such as liposome delivery and receptor-mediated and other endocytosis mechanisms (see, for example, Schwartzenberger et al., Blood 87:472-478, 1996). The present invention can be used in conjunction with any of these or other commonly used gene transfer methods.

In a particular example, to deliver a hGC-1 nucleic acid to the cells of a human subject in an adenovirus vector, the dosage can range from about 107 to 109 plaque forming unit (pfu) per injection but can be as high as 1012 pfu per injection (for disclosure of exemplary, non-limiting, dosage ranges, please see Crystal, Hum. Gene Ther. 8:985-1001, 1997; Alvarez and Curiel, Hum. Gene Ther. 8:597-613, 1997, which are hereby incorporated by reference in their entireties, and specifically for the teaching of gene therapy dosing). Ideally, a subject will receive a single injection. If additional injections are necessary, they can be repeated at three to six month intervals for an indefinite period and/or until the efficacy of the treatment has been established.

For in vivo administration, the cells can be in a subject and the nucleic acid can be administered in a pharmaceutically acceptable carrier. The subject can be any animal in which it is desirable to selectively express a nucleic acid in a cell. The animal of the present invention may be any animal in which selective expression of a nucleic acid in a cell can be carried out according to the methods described herein.

hGC-1 could be used to modulate hGC-1 activity in vitro in the context of gene therapy such as for the treatment of cancer. For example, cells can be collected from the patient and treated ex vivo with hGC-1, washed to remove the hGC-1, then readministered to the patient. This approach offers the advantage of reducing any side-effects of administration of hGC-1 in vivo.

The nucleic acid and the nucleic acid delivery vehicles of this invention, (e.g., viruses; liposomes, plasmids, vectors) can be in a pharmaceutically acceptable carrier for in vivo administration to a subject. The carrier would naturally be selected to minimize any degradation of the active ingredient and to minimize any adverse side effects in the subject, as would be well known to one of skill in the art.

The nucleic acid or vehicle may be administered orally, parenterally (e.g., intravenously), by intramuscular injection, by intraperitoneal injection, transdermally, extracorporeally, topically or the like. The exact amount of the nucleic acid or vector required will vary from subject to subject, depending on the species, age, weight and general condition of the subject, the severity or mechanism of any disorder being treated, the particular nucleic acid or vehicle used, its mode of administration and the like.

Parenteral administration of the nucleic acid or vector of the present invention, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795. For additional discussion of suitable formulations and various routes of administration of therapeutic compounds, see, e.g., Remington: The Science and Practice of Pharmacy (19th ed.) ed. A. R. Gennaro, Mack Publishing Company, Easton, Pa. 1995.

Contemplated in this invention is a method of treating or preventing cancer in a subject by administering hGC-1, and, optionally, a pharmaceutically acceptable carrier. Alternatively, an active fragment of hGC-1, or a hGC-1 encoding nucleic acid in an expressible construct, can be administered. For any of the methods described herein for using hGC-1 or hGC-1 fragments, nucleic acids encoding hGC-1 or its fragments can be administered.

The subject which can be treated by this method can be any animal. The animal of the present invention can be a human. In addition, non-human animals which can be treated by the methods of this invention can include, but are not limited to, cats, dogs, birds, horses, cows, goats, sheep, guinea pigs, hamsters, gerbils and rabbits.

Optimal dosages used will vary according to the individual being treated and the hGC-1 being used. The amount of hGC-1 will also vary among individuals on the basis of age, size, weight, condition, etc. One skilled in the art will realize that dosages are best optimized by the practicing physician and methods for determining dose amounts and regimens and preparing dosage forms are described, for example, in Remington's Pharmaceutical Sciences. For example, suitable doses and dosage regimens can be determined by comparison to agents presently used in the treatment or prevention of hGC-1 related disorders. The optimal dosage is the amount of hGC-1 which results in treatment or prevention of cancer, in the absence of significant side effects.

Typically, the hGC-1 of this invention can be administered orally or parenterally in a dosage range of about 0.1 micrograms/kg to about 100 mg/kg or about 0.1 mg/kg to about 10 mg/kg depending on the clinical response that is to be obtained. Administration of hGC-1 can be stopped completely following a prolonged remission or stabilization of disease signs and symptoms and readministered following a worsening of either the signs or symptoms of the disease, or following a significant change in status, as determined by routine follow-up studies well known to a clinician in this field. Administration may be by any method which retains desired action.

The efficacy of administration of a particular dose of hGC-1 in treating a cancer, or a hGC-1 related disorder, as described herein can be determined by evaluating the particular aspects of the medical history, the signs, symptoms and objective laboratory tests that have a documented utility in evaluating pathophysiological activity of the particular hGC-1 associated disorder being treated. These signs, symptoms and objective laboratory tests will vary depending on the particular disorder being treated, as will be well known to any clinician in this field. For example, if, based on a comparison with an appropriate control group and knowledge of the normal progression of the disorder in the general population or the particular individual, 1) a subject's frequency or severity of recurrences is shown to be improved; 2) the progression of the disease or disorder is shown to be stabilized; or 3) the need for use of other medications is lessened, then a particular treatment can be considered efficacious.

In a particular example, in using the hGC-1 of the present invention to treat cancer, clinical parameters and symptoms which can be monitored for efficacy can include reduction in tumor size or full remission of the disease.

Once it is established that disease activity is significantly improved or stabilized by a particular hGC-1 treatment, specific signs, symptoms and laboratory tests can be evaluated in accordance with a reduced or discontinued treatment schedule. If a disease activity recurs, based on standard methods of evaluation of the particular signs, symptoms and objective laboratory tests as described herein, hGC-1 treatment can be reinitiated.

Additionally, the efficacy of administration of a particular dose of a peptide ligand in preventing an hGC-1 associated disorder in a subject not known to have an hGC-1 associated disorder, but known to be at risk of developing an hGC-1 associated disorder, can be determined by evaluating standard signs, symptoms and objective laboratory tests, known to one of skill in the art, over time. This time interval may be long (i.e., years/decades). The determination of who would be at risk for the development of an hGC-1 associated disorder would be made based on current knowledge of the known risk factors for a particular disorder familiar to clinicians and researchers in this field, such as a particularly strong family history of a disorder or exposure to or acquisition of factors or conditions which are likely to lead to development of an hGC-1 associated disorder.

Methods of administration can be, for example, oral, sublingual, mucosal, inhaled, absorbed, or by injection. It is also noted that not all methods of administering the present hGC-1 polypeptides or nucleic acids require a pharmaceutically acceptable carrier.

In the present invention, the hGC-1, hGC-1 antibody, or active fragment can be orally or parenterally administered in a carrier pharmaceutically acceptable to human subjects. Suitable carriers for oral or inhaled administration of hGC-1 can include one or more of the carriers pharmaceutically acceptable to human subjects. Suitable carriers for oral administration of hGC-1 include one or more substances which may also act as a flavoring agents, lubricants, suspending agents, or as protectants. Suitable solid carriers include calcium phosphate, calcium carbonate, magnesium stearate, sugars, starch, gelatin, cellulose, carboxypolymethylene, or cyclodextrans. Suitable liquid carriers may be water, pyrogen free saline, pharmaceutically accepted oils, or a mixture of any of these. The liquid can also contain other suitable pharmaceutical addition such as buffers, preservatives, flavoring agents, viscosity or osmo-regulators, stabilizers or suspending agents. Examples of suitable liquid carriers include water with or without various additives, including carboxypolymethylene as a pH-regulated gel. The hGC-1 may be contained in enteric coated capsules that release the polypeptide into the intestine to avoid gastric breakdown. For parenteral administration, a sterile solution or suspension is prepared in saline that may contain additives, such as ethyl oleate or isopropyl myristate, and can be injected for example, into subcutaneous or intramuscular tissues, as well as intravenously.

The invention also contemplates a method of reducing hGC1 activity in a subject by administering an antibody to hGC-1 and a pharmaceutically acceptable carrier. Alternatively, an antibody to a functional region of hGC-1 could be administered.

The "sample" of this invention can be from any organism and can be, but is not limited to, peripheral blood, plasma, urine, saliva, gastric secretion, feces, bone marrow specimens, primary tumors, embedded tissue sections, frozen tissue sections, cell preparations, cytological preparations, exfoliate samples (e.g., sputum), fine needle aspirations, amnion cells, fresh tissue, dry tissue, and cultured cells or tissue. It is further contemplated that the biological sample of this invention can also be whole cells or cell organelles (e.g., nuclei). The sample can be unfixed or fixed according to standard protocols widely available in the art and can also be embedded in a suitable medium for preparation of the sample. For example, the sample can be embedded in paraffin or other suitable medium (e.g., epoxy or acrylamide) to facilitate preparation of the biological specimen for the detection methods of this invention.

The term "antibody" is used herein in a broad sense and includes intact immunoglobulin molecules and fragments or polymers of those immunoglobulin molecules, so long as they exhibit any of the desired properties described herein. Antibodies are typically proteins which exhibit binding specificity to a specific antigen. Native antibodies are usually heterotetrameric glycoproteins, composed of two light (L) chains and two heavy (H) chains. The heavy and light chains are typically identical, but not necessarily so. Typically, each light chain is linked to a heavy chain by one or more covalent disulfide bond, while the number of disulfide linkages varies between the heavy chains of different immunoglobulin isotypes. Each heavy and light chain also typically has regularly spaced intrachain disulfide bridges. Each heavy chain typically has at one end a variable domain (V(H)) followed by a number of constant domains. Each light chain typically has a variable domain at one end (V(L)) and a constant domain at its other end; the constant domain of the light chain is typically aligned with the first constant domain of the heavy chain, and the light chain variable domain is typically aligned with the variable domain of the heavy chain. Particular amino acid residues are believed to form an interface between the light and heavy chain variable domains. The light chains of antibodies from any vertebrate species can be assigned to one of two clearly distinct types, called kappa (κ) and lambda (λ), based on the amino acid sequences of their constant domains. Depending on the amino acid sequence of the constant domain of their heavy chains, immunoglobulins can typically be assigned to different classes. There are approximately five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, δ, ε, γ, and μ, respectively.

The term "variable" is used herein to describe certain portions of the variable domains which differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a -sheet configuration, connected by three CDRs, which form loops connecting, and in some cases forming part of, the -sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest" National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain may be identical with or homologous to corresponding sequences in antibodies derived from a particular species or belonging to a particular antibody class or subclass, while the remainder of the chain(s) may be identical with or homologous to corresponding sequences in antibodies derived from another species or belonging to another antibody class or subclass, as well as fragments of such antibodies, so long as they exhibit the desired antagonistic activity (See, U.S. Pat. No. 4,816,567 and Morrison et al., Proc. Natl. Acad. Sci. USA, 81:6851-6855 (1984)).

As used herein, "antigen" when used in the detection context generally means detecting the antigen, specifically hGC-1, or a fragment thereof. The antigens of this invention can also be used to detect antibodies to hGC-1, or fragments thereof.

One example of the method of detecting the antigen is performed by contacting a fluid or tissue sample from the patient with an amount of a an antibody, possibly purified, reactive with the antigen, cells containing the antigen, or fragments of the antigen, and detecting the reaction of the antibody with the antigen. The fluid sample of this method can comprise any body fluid which would contain the antigen or a cell containing the antigen, such as blood, plasma, serum, saliva and urine, sputum, mucus and the like. An antibody used to detect the antigens of this invention is preferably specifically reactive with the antigen.

In the present invention, the step of detecting the binding of the antibody with the antigen can be further aided, in appropriate instances, by the use of a secondary antibody or other ligand which is reactive, either specifically with a different epitope or nonspecifically with the ligand or reacted antibody. The antibody can be labeled with a detectable marker.

Enzyme immunoassays such as immunofluorescence assays (IFA), enzyme linked immunosorbent assays (ELISA) and immunoblotting can be readily adapted to accomplish the detection of the antigen. An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. Other assays for detecting the binding of an antibody to an antigen can be used.

The nucleic acids of this invention can be detected with a probe capable of hybridizing to the nucleic acid of a cell or a sample. This probe can be a nucleic acid comprising the nucleotide sequence of a coding strand or its complementary strand or the nucleotide sequence of a sense strand or antisense strand, or a fragment thereof. The nucleic acid can comprise the nucleic acid of the hGC-1 gene, or a sequence associated with a gene that is associated with the hGC-1 gene, such as the hGC-1 receptor gene. Thus, the probe of this invention can be either DNA or RNA and can bind either DNA or RNA, or both, in the biological sample. The probe can be the coding or complementary strand of a complete gene or gene fragment. The nucleotide sequence of the probe can be any sequence having sufficient complementarity to a nucleic acid sequence in the biological sample to allow for hybridization of the probe to the target nucleic acid in the biological sample under a desired hybridization condition. Ideally, the probe will hybridize only to the nucleic acid target of interest in the sample and will not bind non-specifically to other nucleic acids in the sample or other regions of the target nucleic acid in the sample. The hybridization conditions can be varied according to the degree of stringency desired in the hybridization. For example, if the hybridization conditions are for high stringency, the probe will bind only to the nucleic acid sequences in the sample with which it has a very high degree of complementarity. Low stringency hybridization conditions will allow for hybridization of the probe to nucleic acid sequences in the sample which have some complementarity but which are not as highly complementary to the probe sequence as would be required for hybridization to occur at high stringency. Since sequence divergence can exist between individuals for cancer or tumor-related genes, one skilled in the art can take these population differences into account when optimizing hybridization conditions. The hybridization conditions will therefore vary depending on the biological sample, probe type and target. An artisan will know how to optimize hybridization conditions for a particular application of the present method.

The nucleic acid probes of this invention can be modified nucleic acids. These modified nucleotides are well known in the art and include, but are not limited to, thio-modified deoxynucleotide triphosphates and borano-modified deoxynucleotide triphosphates (Eckstein and Gish, Trends in Biochem. Sci., 14:97-100 (1989) and Porter Nucleic Acids Research, 25:1611-1617 (1997)).

The nucleic acid probe can be commercially obtained or can be synthesized according to standard nucleotide synthesizing protocols well known in the art. Alternatively, the probe can be produced by isolation and purification of a nucleic acid sequence from biological materials according to methods standard in the art of molecular biology (Sambrook et al. 1989. Molecular Cloning: A Laboratory Manual, 2d Ed., Cold Spring Harbor Laboratory Press, Cold Spring Harbor, N.Y.). The nucleic acid probe can be amplified according to well-known procedure for amplification of nucleic acid (e.g., polymerase chain reaction). Furthermore, the probe of this invention can be linked to any of the detectable moieties of this invention by protocols standard in the art.

The detectable moieties to which the nucleic acid probe of this invention can be linked to include, but are not limited to, a hapten, biotin, digoxigenin, fluorescein isothiocyanate (FITC), dinitrophenyl, amino methyl coumarin acetic acid, acetylaminofluorene and mercury-sulfhydryl-ligand complexes, as well as any other molecule or compound which can be linked to a probe and detected either directly or indirectly according to the methods described herein. One skilled in the art will, therefore, appreciate that a probe, such as a nucleic acid probe or an antibody, can be labeled with a detectable moiety that can be directly detected, such as a flurorochrome or a dye, such as a chromogenic dye, and the use of secondary reagents to detect the probe is not strictly required.

It is further contemplated that the present invention also includes methods for oligonucleotide hybridization wherein the hybridized oligonucleotide is used as a primer for an enzyme catalyzed elongation reaction such as in situ PCR and primed in situ labeling reactions, whereby haptenized nucleotides are incorporated in situ. Additionally included are methods for in situ hybridization, employing synthetic peptide nucleic acid (PNA) oligonucleotide probes (Nielsen et al., 1991. "Sequence-selective recognition of DNA by strand displacement with a thymine-substituted polyamide." Science 254:1497-1500; Egholm et al., 1993. "PNA hybridizes to complementary oligonucleotides obeying the Watson-Crick hydrogen bonding rules." Nature 365:566-568).

The levels of protein in this invention can be detected by ELISA, FIA, immunoblotting or any other immunodetection method. These methods can be combined with histochemical or microscopic analysis to determine the levels of proteins in samples.

By "active hGC-1 gene product" is meant a product of the hGC-1 gene which can exert a biological function associated with the hGC-1 gene. An active hGC-1 gene product may act as a transcriptional activator to elicit downstream effects. The hGC-1 gene product may also function from outside of the cell either as a ligand which could bind to its cell surface receptor and participate in signal transduction, or it may function through the interaction with other secreted proteins and extracellular matrix molecules outside of cells. Any effect associated with hGC-1 associated cancers is also contemplated by this invention.

The term "inhibition" is familiar to one skilled in the art and is used herein to describe any reduction in the activity of the hGC-1 gene product. The degree of inhibition does not have to be complete, such as completely inhibiting the activity of the hGC-1 gene product, and therefore comprises any inhibition of the activity of the hGC-1 gene product relative to the activity of the hGC-1 gene product in a similar environment in the absence of the inhibiting compound.

The "cells" of this invention include any cell type, cancerous or noncancerous, that may express or be affected by the expression of a hGC-1 gene or the activity of a hGC-1 protein. Examples include, but are not limited to, prostate cancer cells.

The following Examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention.

EXAMPLES

The following examples are put forth so as to provide those of ordinary skill in the art with a complete disclosure and description of how the compounds, compositions, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in □C or is at ambient temperature, and pressure is at or near atmospheric.

One important aim of the study of hematopoiesis is to understand how hematopoietic stem cells undergo lineage restriction (Ogawa, M. (1993) *Blood* 81, 2844-53). A major advantage of the modified two-phase liquid culture system described herein is that it permits the isolation of a relatively synchronized committed cell population from early hematopoietic progenitors to late progenitors (phase I) and from lineage-committed late progenitor cells (phase II). This system enabled easy manipulation of the culture conditions and isolation of hematopoietic cells at various stages. Other systems involving the expansion of hematopoietic stem cells in liquid cultures of human progenitor cells have been described (Warren, M. K., Rose, W. L., Beall, L. D. & Cone, J. (1995) *Stem Cells* 13, 167-74). There are some inherent limitations of the system used in the present study, including the use of conditioned medium and fetal calf serum. However, these were largely controlled for by explicitly comparing cultures grown in the presence of one lineage-specific cytokine (e.g., EPO) and not the other two (e.g., G-CSF or TPO), with other culture conditions remaining constant. Cells were further enriched by using FACS with lineage-restrictive cell markers (FIG. 1). In this manner, and given the fact that culture conditions prior to the application of G-CSF and EPO were identical, the individual cytokines became the dominant parameter in determining the subsequent differential gene expression profiles in the modified two-phase liquid culture system.

Differential display technology was used to analyze differential gene expression among early precursors of erythroid, myeloid and megakaryocytic lineage cells, expecting to find novel lineage-specific genes or markers and, thus, clues to possible novel functions of known genes in hematopoiesis. Others have applied this approach to identify differentially expressed genes in very immature (CD34+/CD38– vs. CD34+/CD38+) progenitors (Graf, L. & Torok-Storb, B. (1995) *Blood* 86, 548-56) or to compare gene expansion profiles in normal CD34+ cells with those in clones derived from acute myeloid leukemia patients (Bond, H. M., Bonelli, P., Mesuraca, M., Agosti, V., Masone, C., Cuomo, C., Nistico, A., Tassone, P., Tuccillo, F., Cecco, L., Iacopino, L., Barbieri, V., Cerra, M., Costanzo, F. S., Morrone, G. & Venuta, S. (1998) *Stem Cells* 16, 13643). The current Examples, below, used very stringent criteria to define a gene as differentially expressed, including a greater than three-fold increased expression of the gene of interest in one lineage in two independent experiments and subsequent confirmation by reverse dot blots and northern blots.

Herein presented is the isolation and characterization of one gene so identified: the human olfactomedin-like gene hGC-1. hGC-1 appeared to be a useful marker for the early stage of myeloid lineage development, showing strong lineage- and differentiation stage-specific expression. In the modified two-phase liquid culture system, hGC-1 showed an expression pattern limited to early precursors of the granulocytic lineage, not erythroid or megakaryocytic precursor cells.

As shown, hGC-1 expression in the multipotent prepromyelocytic cell line HL-60 was observed only after induction of granulocytic differentiation, not monocytic differentiation. Because of the characterization and kinetics of hGC-1 expression, we hypothesize that hGC-1 is under developmental controls during granulocytic differentiation. Our results from two-phase liquid culture systems showed that hGC-1 was strongly expressed in all three lineages during the first day of transition from phase I to phase II. The reason for this biphasic expression pattern remains unknown. Further investigation of the hGC-1 promoter and its genomic structure will allow this to be determined and may provide a means of investigating the regulation of lineage-specific and differentiation-related gene expression.

The diverse roles of the extracellular matrix are reflected in its highly complicated structure; the number of known matrix components increases continually. Yet the mechanisms of extracellular matrix assembly and how they influence cell behavior are only just beginning to be understood. It is now widely accepted that many functions of cells and tissues are dynamically regulated by the extracellular matrix. In addition to its conventional role in providing a scaffold for building tissues, the extracellular matrix acts as a directional highway for cellular movement and provides cells with instructions promoting survival, proliferation and differentiation.

hGC-1 and other olfactomedin-related proteins are secreted glycoproteins with a conserved C-terminal motif. This family of proteins is named for their amino acid sequence similarity to olfactomedin, an extracellular matrix protein of the bullfrog olfactory epithelium (Snyder, D. A., Rivers, A. M., Yokoe, H., Menco, B. P. & Anholt, R. R. (1991) *Biochemistry* 30, 9143-53; Bal, R. S. & Anholt, R. R. (1993) *Biochemistry* 32, 1047-53; Yokoe, H. & Anholt, R. R. (1993) *Proc Natl Acad Sci USA* 90, 4655-9). The glycoprotein olfactomedin is specifically expressed in the olfactory neuroepithelium, forming homopolymers held together by disulfide bonds and carbohydrate interactions. On the basis of its sequence and predicted structure, olfactomedin may function in the maintenance, growth, or differentiation of olfactory cilia. hGC-1 shares homology with full-length olfactomedin, not only its C-terminal region, and has a very similar secondary structure. However, olfactomedin and hGC-1 have totally different tissue distributions. Olfactomedin is mainly expressed in the brain and nervous system; hGC-1 is only expressed in the digestive system, prostate and bone marrow. Interestingly, another olfactomedin-related glycoprotein, Noelin-1, also has a restricted tissue distribution. Noelin-1 is confined to the dorsal neural tube, the ontogenetic precursor of the neural crest, and has an important role in making the neural tube competent to form neural crest. These data suggest that hGC-1 has a causative role in the development of the organs and tissues in which it is expressed.

So far, several members of the family of human olfactomedin-related proteins have been cloned; their functions are still being deciphered. The first link between an olfactomedin-related protein and human disease came with the discovery of the TIGR protein (Nguyen, T. D., Chen, P., Huang, W. D., Chen, H., Johnson, D. & Polansky, J. R. (1998) *J Biol Chem* 273, 6341-50); a genetic defect in this molecule may cause juvenile open angle glaucoma (Stone, E. M., Fingert, J. H., Alward, W. L., Nguyen, T. D., Polansky, J. R., Sunden, S. L., Nishimura, D., Clark, A. F., Nystuen, A., Nichols, B. E., Mackey, D. A., Ritch, R., Kalenak, J. W., Craven, E. R. & Sheffield, V. C. (1997) *Science* 275, 668-70). A possible involvement of TIGR in glucocorticoid-induced glaucoma is also speculated, in which molecular interactions between TIGR and other extracellular matrix proteins of the trabecular meshwork may influence humoral outflow. A recombinant C-terminal truncated TIGR cannot exit the cell, and accumulation of this mutated form inside the cell reduces secretion of the endogenous form (Caballero, M., Rowlette, L. L. & Borras, T. (2000) *Biochim Biophys Acta* 1502, 447-60).

Additionally, a homologous olfactomedin domain has been found in the N-terminal extracellular region of CIRL (Krasnoperov, V. G., Bittner, M. A., Beavis, R., Kuang, Y., Salnikow, K. V., Chepurny, O. G., Little, A. R., Plotnikov, A. N., Wu, D., Holz, R. W. & Petrenko, A. G. (1997) *Neuron* 18, 925-37; Ichtchenko, K., Bittner, M. A., Krasnoperov, V., Little, A. R., Chepurny, O., Holz, R. W. & Petrenko, A. G. (1999) *J Biol Chem* 274, 5491-8), a G-protein-coupled receptor containing domains characteristic of cell adhesion proteins. These data suggest that the C-terminal olfactomedin domain may have an important role in secretion of hGC-1 and in extracellular protein signal transduction.

In addition to their common structural domain, olfactomedin family members share the trait of having tightly restricted tissue-specific expression, with different family members being expressed in distinct sets of tissues. These features point to possible involvement of olfactomedin-like proteins in tissue-specific extracellular regulation of differentiation pathways. The current characterization of the human olfactomedin-like gene, hGC-1, may contribute to a better understanding of the structure and possible functions of this superfamily.

In summary, a modified method for the liquid culture of human hematopoietic stem cells to enrich for lineage-expanded progenitor/precursor cells was developed RNA derived from these cells was used to clone gene products preferentially or exclusively expressed in early erythroid, myeloid, or megakaryocytic cells. One of these, hGC-1, is primarily expressed as a major extracellular glycoprotein during granulopoiesis. Characterization of this gene and its products suggests that hGC-1 may be an extracellular matrix effector of myeloid differentiation.

Methods and Materials

Cell Culture and Cell Line

Informed consent was obtained from all blood donors. Peripheral blood mononuclear cells (pbmcs) obtained from normal human blood donors were isolated by centrifugation on a gradient of Ficoll-Hypaque (Organon Teknika Corporation, Durham, N.C.), harvested, and washed twice in Dulbecco's PBS. The pbmcs were cultured in a modified two-phase liquid culture system that has been reported previously to permit the growth of erythroid, myeloid and megakaryocytic cells (Liu, W., Wang, M., Tang, D.C., Ding, I. & Rodgers, G. P. (1999) *Br. J. Haematol.* 105, 459-69). In brief, following 7 days of culture (phase I), the nonadherent cells were harvested, washed and recultured in a phase II medium. Human recombinant EPO (1 U/ml, Ortho Pharmaceutics, Raritan, N.J.), G-CSF (10 ng/ml, Sigma, St. Louis, Mo.), or TPO (10 ng/ml, Gene Technologies Inc., Rockville, Md.) was added at the beginning of phase II to induce erythroid, myeloid or megakaryocytic lineage differentiation, respectively. The K562, HL-60, MEG-01 and MOLT-4 cell lines were purchased from ATCC (Manassas, Va.) and cultured in RPMI-1640 medium supplemented with 10% FBS in 5% $CO_2$. HL-60 cells were maintained in continuous logarithmic growth at densities between 5 and $10 \times 10^5$ cells/ml. Experimental cultures were seeded from the parental culture at $5 \times 10^5$ cells/ml and induced to differentiate by treatment with 1 µM all-trans retinoic acid (RA) or 10 ng 12-O-tetradecanoylphorbol-13-acetate (TPA), respectively. The differentiation of early precursors of these three lineages and HL-60 cells was assessed morphologically on cytocentrifuge slides stained with May-Grunwald and Giemsa stains (Sigma, St. Louis, Mo.). 293 cells (ATCC, Manassas, Va.) were maintained in DMEM containing 10% fetal bovine serum.

Cell Purification by FACS

Monoclonal antibodies (mabs) used for sorting precursors of erythroid, myeloid and megakaryocytic lineages included a fluorescein isothiocyanate (FITC)-conjugated anti-glycophorin antibody (Immunotech, Coulter, Westbrook, Me.), and anti-CD13 and anti-CD61 antibodies conjugated to PE (Pharmingen, San Diego, Calif.). On day 5 of phase II, cells were suspended in 0.5 ml of phase II culture medium and incubated with the appropriate antibodies at the recommended dilution at 4° C. for 30 min. The cells were then washed twice with PBS and resuspended in 1 ml of culture medium for fluorescence activated cell sorting (FACS) on a flow cytometer (Epics Elite, Coulter, Hialeah, Fla.).

Differential Display

Cells isolated by FACS were washed twice in PBS, and RNA was extracted using Trizol Reagent (Molecular Research Center Inc., Cincinnati, Ohio). Differential display was performed with an RNA Image Kit (GenHunter, Nashville, Tenn.). Total RNA was treated with DNase I to remove chromosomal DNA contamination with a Messageclean Kit (GenHunter) prior to performing differential display experiments. Reverse transcription was carried out by incubating a 20-μl reaction mixture containing 0.2 μg DNA-free total RNA, 1.6 μl of each dNTP (250 μM), 4.0 μl 5×RT buffer, 2.0 μl of one of the three different one-base anchored $H-T_{11}M$ primers (2 μM, where M may be G, A, or C) at 65° C. for 5 min, 37° C. for 60 min, and 75° C. for 5 min. After the tubes had been held at 37° C. for 10 min, the thermocycler was paused; 1 μl of MMLV reverse transcriptase was added to each tube and quickly mixed by finger tapping before continuing incubation. The polymerase chain reaction was carried out with 16 arbitrary primers (H-AP1 through H-AP16). In a total volume of 20 μl, the reaction mixture contained 2 μl RT-mixture from the previous step, 1.6 μl of each DNTP (25 μM), 2.0 μl 10×PCR buffer, 2.0 μl H-AP primer (2 μM), 2 μl $H-T_{11}M$ (2 μM), 0.2 μl [$\alpha$-$^{33}$P]-dATP (2000 Ci/mmole), and 0.2 μl Taq DNA polymerase (Qiagen Inc., Valencia, Calif.). PCR was carried out using a Thermal Cycler 480 (Perkin Elmer, Norwalk, Conn.) at 94° C. for 30 seconds, 40° C. for 2 min, and 72° C. for 30 seconds for 40 cycles, followed by 72° C. for 5 min. The resulting PCR products were subjected to 6% denaturing polyacrylamide gel electrophoresis (PAGE). The gels were then dried and exposed to Biomax film (Kodak, Rochester, N.Y.) overnight. Each reaction was performed in duplicate from independent RNA sample preparations. Only the differentially expressed bands that were reproducible on the gel were excised and eluted by boiling the gel slices along with the associated 3M drying paper for 15 min. Eluted proteins were then precipitated with 100% ethanol in the presence of 3 M sodium acetate and 10 mg/ml glycogen as a carrier. Reamplification was performed using the same primer set and PCR conditions, except that the dNTP concentrations were 20 μM instead of 2 μM and no isotope was added. The PCR products were run on agarose gels and checked to see if the sizes of reamplified PCR products were consistent with their sizes on the PAGE gel. The reamplified cDNA probe was extracted from the agarose gel using a Qiaex II gel extraction kit (QIAGEN).

cDNA Cloning and Sequence Analysis

5'-RACE and 3'-RACE were performed using the Marathon™ cDNA Amplification Kit and bone marrow Ready Marathon™ cDNA (Clontech, Palo Alto, Calif.). Gene-specific primers were designed according to the original hGC-1 partial cDNA sequence derived from differential display. The PCR products of 5'-RACE and 3'-RACE were purified from a 0.8% agarose gel and cloned into the TA vector. The full-length cDNA sequence was obtained by overlapping sequences derived from 5'RACE, 3'RACE and the original differential display sequence. GCG (Genetics Computer Group, Madison, Wis.) Version 8 was used to carry out homology searches of GenBank, EBI, SwissProt, and EST databases.

Fluorescence in situ Hybridization and Chromosomal Mapping of hGC-1

Metaphase chromosome spreads were prepared from human peripheral blood lymphocytes. Standard FISH protocols were followed (Pack, S. D., Zbar, B., Pak, E., Ault, D. O., Humphrey, J. S., Pham, T., Hurley, K., Weil, R. J., Park, W. S., Kuzmin, I., Stolle, C., Glenn, G., Liotta, L. A., Lerman, M. I., Klausner, R. D., Linehan, W. M. & Zhuang, Z. (1999) *Cancer Res* 59, 5560-4). BAC DNA containing hGC-1 was labeled by nick-translation (Roche, Indianapolis, Ind.) with digoxigenin-11-dUTP, and ethanol-precipitated in the presence of a 50-fold excess of herring sperm DNA and a 50-fold excess of $C_o$t-1 human DNA. Biotinylated probes were detected with FITC-conjugated avidin (Vector) and digoxigenin-labeled probes and a rhodamine-conjugated anti-digoxigenin antibody (Roche, Indianapolis, Ind.). Chromosomes were counterstained with 4,6-diamidino-2-phenylindole (DAPI). Images were captured with a Zeiss epifluorescence microscope equipped with a thermoelectrically cooled CCD camera (Photometrics CH250). As a second independent mapping method, PCR was also performed to detect hGC-1 sequences in the Genebridge 4 Radiation Hybrid Screening Panel (Research Genetics, Inc.) using a set of primers designed based on the cDNA sequence of hGC-1: 5'-CTGATGGCAG TGACAAAGTGC-3' (SEQ ID NO:5), 5'-TGTAGTGTATGTGGTCGTTC-3' (SEQ ID NO:6). PCR was carried out in a 20-μl reaction volume for 35 cycles. Each cycle consisted of denaturation at 94° C. for 30 s and annealing at 68° C. for 3 min, and 10 μl of each reaction was analyzed by electrophoresis through an 0.9% agarose gel in TAE buffer. The PCR results of the radiation hybrid panel were mapped for genes relative to the radiation hybrid map of the human genome (Hudson, T. J., Stein, L. D., Gerety, S. S., Ma, J., Castle, A. B., Silva, J., Slonim, D. K., Baptista, R., Kruglyak, L., Xu, S. H. & et al. (1995) *Science* 270, 1945-54).

Northern Blotting

Total RNA (10 μg) extracted from glycophorin A+ (erythroid), CD13+ (myeloid) and CD61+ (megakaryocytic) cells and four cell lines (K562, HL-60, MEG-01 and MOLT-4 cells) was subjected to electrophoresis on denaturing formaldehyde gels with 1% agarose. The RNA was then transferred to a NYTRAN nylon membrane overnight using the Turboblotter™ System (Schleicher & Schuell, Keene, N.H.) and exposed to UV light for cross-linking as above. The cDNA probes were made by random primer labeling with [$\alpha$-$^{32}$P]-dCTP using the Prime-It® RmT Kit (Stratagene, La Jolla, Calif.) and purified on Probe Quant™ G-50 microcolumns as above. Membranes were pre-incubated with ExpressHyb solution (Clontech) at 68° C. for 30 min. and hybridized with a radiolabeled probe at 68° C. for one hour. After removal of the radiolabeled probe, the membrane was washed first in a solution containing 2×SSC, 0.05% SDS at room temperature for 30 min., then washed in 0.1×SSC, 0.1% SDS solution with continuous shaking at 50° C. for 40 min. The membrane was exposed to X-ray film at −70° C. overnight. Membranes were stripped between probes by incubating the blots in sterile $H_2O$ containing 0.5% SDS at 95° C. for 10 min. Expression of hGC-1 in multiple human tissues was determined by hybridization of cDNA probes to Multiple Tissue Northern (MTN™) Blots (Clontech) according to the hybridization conditions described above.

Reverse Transcriptase (RT)-PCR

Total RNA was prepared from cells by using Trizol reagent, (Molecular Research Center, INC. Cincinnati, Ohio), and cDNA was prepared from 2 μg of total RNA with oligo(dT) priming using the Superscript Preamplification System (Life Technologies, Gaithersburg, Md.). RT-PCR analyses were performed by using 1/40 of the reverse transcription reaction mixture (the amount of cDNA derived from 50 ng of total RNA) as a template to maintain a constant amount of input cDNA for all samples analyzed. PCR amplification using AmpliTaq (PE Biosystems, Poster City, Calif.) was carried out so that the reaction was completed within the exponential cycling phase. The PCR conditions were 5 minutes at 94° C., followed by cycling for 30 seconds at 94° C., 15 seconds at 60° C., and 30 seconds at 72° C., followed by elongation for 7 minutes at 72° C.; both hGC-1 and β-actin were amplified for 35 cycles. PCR products (20 μl) were fractionated on 2% agarose gels and visualized after ethidium bromide staining. Because yields of RNA preparations may vary, equal amounts of RNA were used for cDNA preparations. For all samples, cDNA derived from 50 ng of total RNA was amplified, and β-actin message levels were assessed. Oligonucleotide PCR primers (shown with final product size) were as follows: β-actin (650 bp) 5'-CTGGCCGGGACCT-GACTGACTACCTC-3' (SEQ ID NO:7) and 5'-AAA-CAAATAAAGCCATGCCAA TCTCA-3' (SEQ ID NO:8); hGC-1 (630 bp), 5'-GATTACTCTCCCCAGCATC-3' (SEQ ID NO:9) and 5'-CTCTTT CACCCTAACTCC-3' (SEQ ID NO:10).

In vitro Translation and N-Glycosylation of hGC-1

To define the biochemical features of hGC-1, in vitro translation and posttranslational processing were carried out. The PCR-amplified hGC-1 protein coding region was subcloned into the PCR II TOPO vector (Invitrogen). The resulting PCRII-TOPO-hGC-1 construct was sequenced to confirm that it had the same sequence as the cDNA. hGC-1 plasmids PCRII-TOPO-hGC-1 and pcDNA-E-hGC-1-his-$V_5$ (subcloned as described below) were employed as templates, using a TNT Quick T7 coupled transcription/translation system (Promega) with [$^{35}$S]-methionine (15 mCi/ml, Amersham Pharmacia Biotech). Labeled hGC-1 was analyzed on 4-12% Bis-Tris gels after incubation with or without canine pancreatic microsomal membranes (CPMM) (Promega) to N-glycosylate the protein.

Transfection, Western Blotting and N-Glycanase Analysis of hGC-1

The PCR-amplified hGC-1 coding region was subcloned into the pUni/V5-His-TOPO donor vector (Echo Cloning System, Invitrogen). The resulting pUni-hGC-1 was sequenced to confirm that it had the same sequence as the cDNA. By mixing the donor pUni-hGC-1 with the acceptor vector pcDNA3.1-E and the Cre recombinase, a fusion plasmid pcDNA3.1-E-hGC-1 was created. This plasmid contained the V5-His epitope tag, and could be used to express the hGC-1 product in vitro and in 293 cells. 293 cells were transfected with pcDNA3.1-E-hGC-1 by calcium phosphate coprecipitation. Thirty-six hours after transfection, 293 cells in 10-cm culture dishes were harvested by gentle scraping in 1 ml of ice-cold PBS and pelleted by centrifugation at 1200 rpm at 4° C. The PBS was aspirated and the cell pellet ($10^6$ cells) resuspended in 0.5 ml of ice-cold buffer A [which contained 50 mM Tris-Cl (pH 7.4), 150 mM NaCl, 5 mM EDTA, 0.5% NP-40, 1 mM phenylmethylsulfonyl fluoride, 10 μg/ml aprotinin, 10 μg/ml leupeptin]. The lysis mixture was rotated 360° for 30 min at 4° C. and then cleared by centrifugation at 12,000×g for 10 min at 4° C. Cell lysates from non-transfected and pcDNA-E-hGC-1-his-$V_5$ transfected 293 cells were treated in the presence or absence of PNGase (New England BioLabs). Samples containing 10 μg of protein were subjected to electrophoresis on 4-12% SDS-PAGE, followed by western blotting with a horseradish peroxidase-conjugated anti-$V_5$ mab (1:5000) (Invitrogen). $V_5$ immunoreactivity was visualized directly with enhanced chemiluminescence (ECL System, Amersham, Arlington Heights, Ill.) according to the manufacturer's instructions.

Example 1

In vitro Induction of Three Hematopoietic Lineages and Enrichment of Glycophorin A+ (Erythroid), CD13+ (Myeloid) and CD61+ (Megakaryocytic) Cells Peripheral blood mononuclear cells were isolated as described above and incubated in phase I medium for one week. The cells were then collected and washed, and lineage-specific cytokines were added. For erythroid and myeloid lineage differentiation, EPO (1 U/ml) and G-CSF (10 ng/ml) respectively were added to the phase II medium (containing 30% FBS) at the beginning of phase II. For megakaryocytic lineage development, TPO (10 ng/ml) was added to serum-free medium that contained 20% BIT (FIG. 1). On day 5, in phase II culture medium, glycophorin A+ (erythroid), CD13+ (myeloid) and CD61+ (megakaryocytic) cells were isolated using their corresponding FITC- or PE-conjugated mabs and FACS (FIG. 1). The average percentage of positive cells in each induced cell population in presorted samples was 9.4%, 8.6% and 6.2%, respectively. The development of the three lineages was monitored morphologically on cytocentrifuge slides (FIG. 1).

Example 2

Differential Display and Determination of the Full-Length cDNA Sequence

Total RNA was isolated from glycophorin A+, CD13+ and CD61+ cells, reverse-transcribed, and amplified by PCR in the presence of [α-$^{33}$P]-dATP. A total of 16 5'-arbitrary primers (H-AP1 through H-AP16) in combination with three 3' one-base-anchored oligo(dT) primers (H-$T_{11}$A, H-$T_{11}$C and H-$T_{11}$G) were used. The PCR products were displayed on 6% DNA sequence gels and autoradiographed. Each differential lane yielded 75-100 discrete bands, allowing evaluation of more than 10,000 RNAs, thought to represent about 50% of the estimated repertoire of 15,000-20,000 cellular mRNAs. Bands that showed at least a three-fold increased expression pattern among the three lineages, and were reproducible in two independent mRNA sample preparations, were eluted and subjected to PCR reamplification. Among the 48 primer sets, 130 bands of interest were excised and eluted, of which 112 bands were reamplified successfully.

Figure 2A:
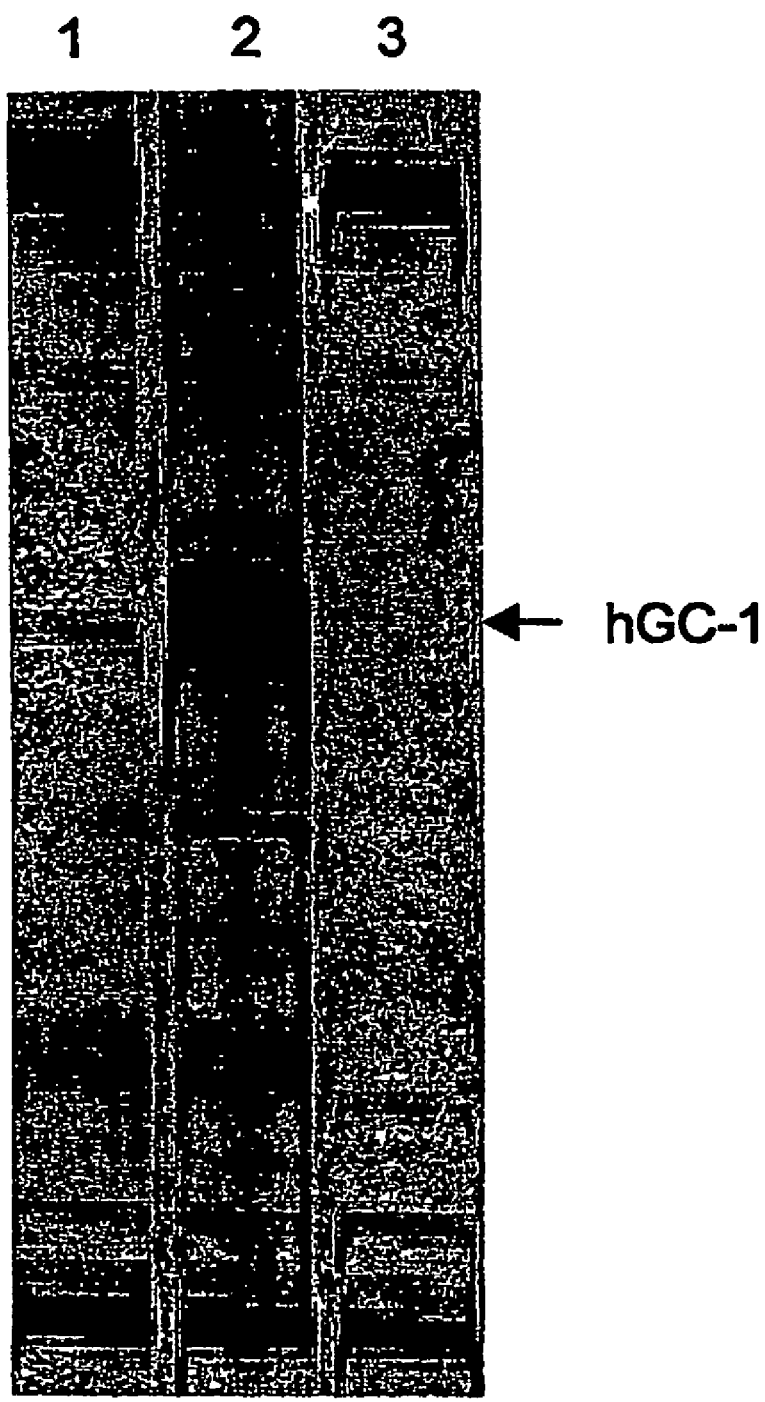
FIG. 2. (A) Differential display of PCR products from total RNAs of glycophorin A+ (erythroid), CD13+ (myeloid) and CD61+ (megakaryocytic) cells. [$\alpha$-$^{33}$P]-dATP-labeled PCR products amplified with 5'-AP primers and 3'-oligo(dT) primers were electrophoresed through a 6% denaturing polyacrylamide gel and exposed to x-ray film for 24 hours. The differentially displayed hGC-1 fragment is indicated by arrows. (B) Deduced cDNA and protein sequence of hGC-1 (SEQ ID NO:4). Nucleotides composing the region identical to the original DD-PCR fragment are underlined with a single solid line. The N-terminal amino acid of mature hGC-1 is aspartic acid, indicated by an arrow. It is preceded by a 20-amino acid signal peptide, indicated by the boxed area, which contains the initiating methionine. hGC-1 protein contains six potential N-linked glycosylation sites, indicated by arrowheads. The polyadenylation motifs are further underlined with curved dashed lines. The star indicates the termination codon.

The cDNA fragment on differential display gels that led to the hGC-1 myeloid clones we eventually analyzed is shown in FIG. 2A. 5'-RACE and 3'-RACE were performed using a Marathon cDNA amplification kit and bone marrow Marathon-Ready cDNA (Clontech). The original hGC-1 sequence comprising 200 bp from the differential display isolate was used to design gene-specific primers as follows: 5'-RACE: 5'-GCACATCACATACACCAGCAAGG-3' (SEQ ID NO:11). 3'-RACE: 5'-CAGTGCAGT AGTTGGAAACCT-TGCTGG-3' (SEQ ID NO:12). The full-length sequence of hGC-1 was obtained by overlapping the 5'-RACE, 3'-RACE and original differential display sequences. FIG. 2B shows the nucleotide sequence of hGC-1 (SEQ ID NO:2). This sequence was also confirmed by screening the hGC-1 sequence against the database of human expressed sequence tags (dbEST) at the NCBI (http://www.Ncbi.nlm.nih.gov/ dbEST). cDNA clones with significant homology were identified, obtained from Genome Systems and sequenced. The human EST clone encoding the full-length hGC-1 cDNA was deposited by the I.M.A.G.E. consortium (I.M.A.G.E. ID: 457140) and distributed by Genome Systems. The hGC-1 cDNA is 2849 nucleotides in length, and its polyadenylation signal is located at nucleotide 2818.

Example 3

Gene Structure and Chromosomal Localization of hGC-1

Using the basic BLAST search, we screened all sequences in the GenBank, EMBL, DDBJ and PDB databases with hGC-1 cDNA and obtained a human genomic DNA sequence from clone RP11-209J19 on chromosome 13 (Accession: AL390736) with significant homology. Then intron-exon boundaries were defined by comparing the genomic sequence and the cDNA sequence. As shown in FIG. 3A, the hGC-1 gene consists of 5 exons spanning over 23 kb. The sizes of the exons range from 156 (exon 2, 4) to 801 bp (exon 5, last exon), whereas those of the introns vary from 0.98 (intron 3) to 7.4 kb (intron 2).

To identify the chromosomal localization of hGC-1, we performed FISH and radiation hybrid mapping. We performed FISH analysis with full-length hGC-1 cDNA as a probe and observed a weak signal on chromosome 13q. Therefore, we performed a labeling FISH analysis with the BAC clone containing the hGC-1 gene. We obtained strong signals at chromosome position 13q14.3 (FIG. 3B). To confirm this localization, we employed radiation hybrid mapping using the Genebridge 4 radiation hybrid panel. PCR products of the expected size (300 bp) were amplified from 29 out of 93 hybrid cell lines. Comparison with the human chromosomal content of the hybrids, as determined by the Whitehead Institute/MIT Center for Genome Research, localized the hGC-1 gene to chromosome 13 and placed it 2.63 cR from D13S153, locating it on human chromosome 13q14.3 (FIG. 3C). Both Rb and BRCA-2, two important tumor suppressors, are also located on 13q14.

Example 4

Expression Patterns in Leukemia Cell Lines and Multiple Tissues

To further characterize hGC-1, we examined the expression patterns of homologous transcripts in K562, HL-60, MEG-01 and MOLT-4 cell lines (FIG. 4A) and 22 normal human tissues (FIG. 4B) by northern blot hybridization. hGC-1 was specifically expressed in the myeloid (CD13+) lineage, but not expressed in K562, HL-60, MEG-01 or MOLT-4 cell lines. The prepromyelocytic cell line HL-60 expresses hGC-1 only when these cells are induced to differentiate towards granulocytes, but not under conditions of forced monocytic differentiation. The protein sequence of hGC-1 indicates that it is a member of the olfactomedin-related family of glycoproteins, which includes olfactomedin, TIGR, NOELIN-2 and latrophilin-1. Like other olfactomedin-like genes with tissue-restricted patterns of expression, hGC-1 is expressed only in prostate, small intestine, colon, bone marrow, and stomach, and is absent in all other tissues examined. In vitro translation and ex vivo expression showed that hGC-1 is an N-linked glycoprotein.

Example 5

Kinetics of hGC-1 Expression During Hematopoiesis

Figure 5A:
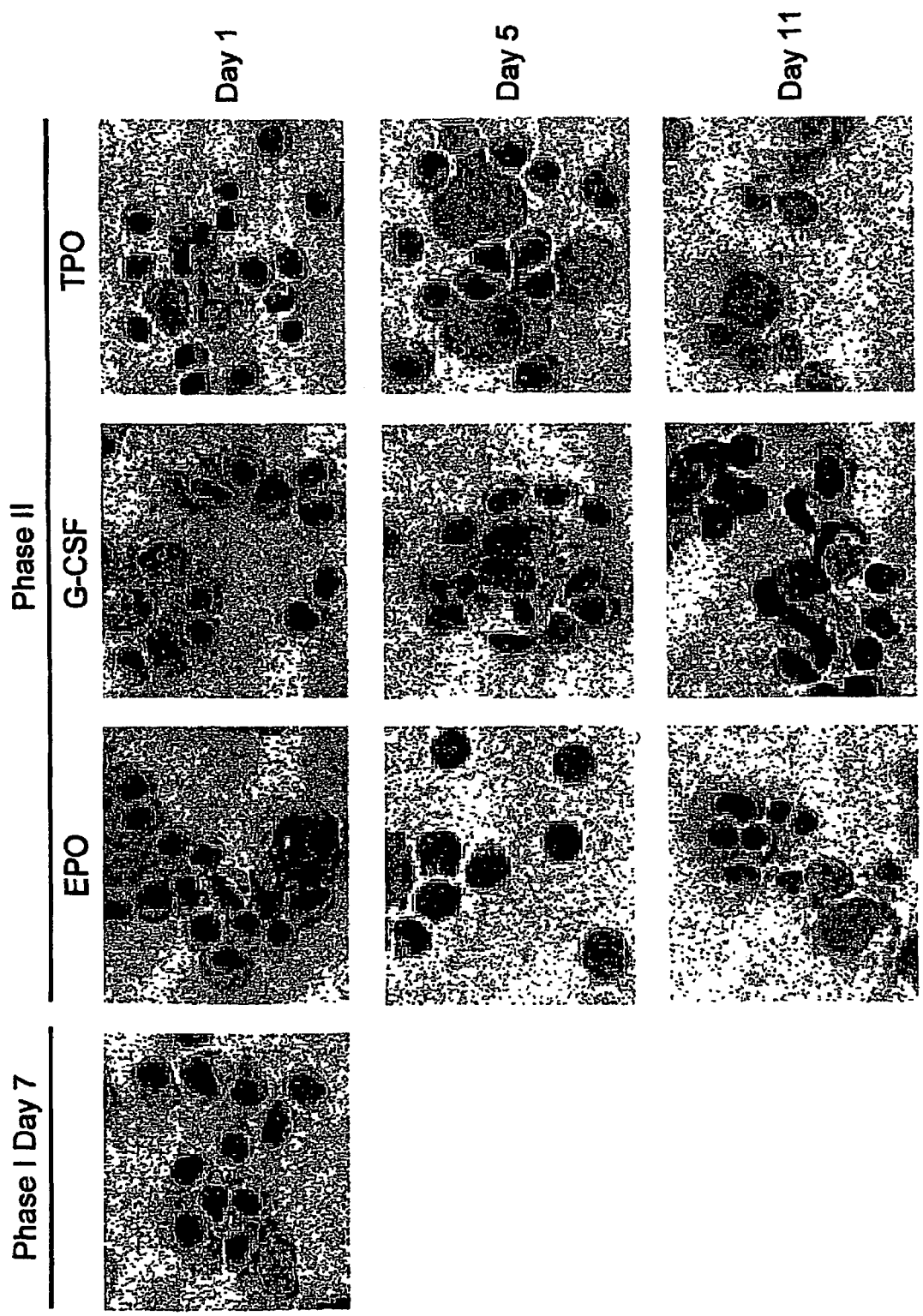
FIG. 5. (A and B) Induction of hGC-1 expression in a two-phase liquid culture system and in the HL-60 cell line. (A) Wright-Giemsa-stained cytocentrifuge preparations of cells from two-phase liquid cultures induced to differentiate toward the erythroid, myeloid, and megakaryocytic lineages. Representative images from cultures at 1, 5 and 11 days are shown. (B) EtBr-stained PAGE of the RT-PCR products of the hGC-1 and β-actin mRNAs from two-phase cell cultures collected on days indicated. (C and D) Induction of hGC-1 expression during differentiation of HL-60 cells toward granulocytes and monocytes. (C) Wright-Giemsa-stained cytocentrifuge preparations of HL-60 cells induced to differentiate toward granulocytes and monocytes. Representative images from cultures at 1, 2, 3, 5 and 7 days are shown. (D) EtBr-stained PAGE of RT-PCR products of the hGC-1 and β-actin mRNAs from HL-60 cells collected on the days indicated.
Figure 5B:
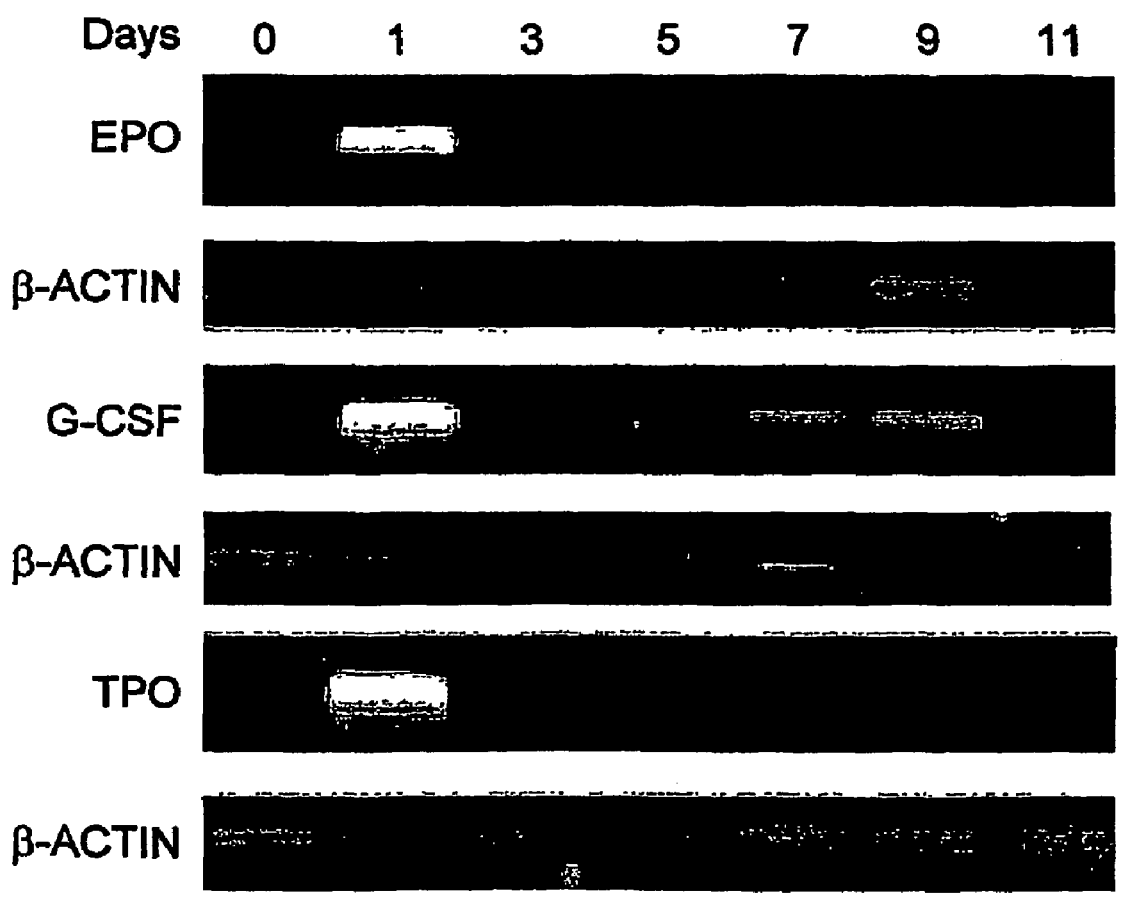
Figure 5C:
Figure 5D:
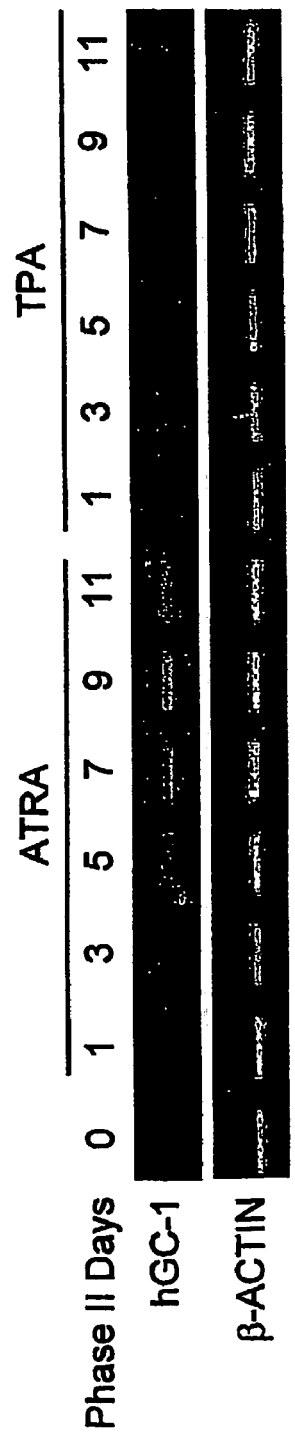

Our studies of hGC-1 expression using differential display and northern analysis indicated that expression of this gene is limited to the myeloid lineage. To gain more insight into the time course of hGC-1 expression during myeloid lineage development, we performed the more sensitive RT-PCR assays. Peripheral blood mononuclear cells were isolated as described above and incubated in phase I medium for one week. The cells were then collected and washed, and lineage-specific cytokines were added. For erythroid and myeloid lineage differentiation, EPO (1 U/ml) and G-CSF (10 ng/ml) were respectively added to medium containing 30% FBS at the beginning of phase II. For megakaryocytic lineage development, TPO (10 ng/ml) was added to serum-free medium containing 20% BIT. On days 1, 3, 5, 7, 9, and 11, cells were collected, and hGC-1 expression was determined by RT-PCR (FIG. 5B). Interestingly, on day 1, hGC-1 was expressed in all three lineages. But after that, hGC-1 was expressed only in the myeloid lineage, not in the erythrocytic or megakaryocytic lineages. The promyelocytic HL-60 cell line was established from cells of a patient with AML type M2; these cells can be induced to differentiate toward cells carrying granulocytic or monocytic markers when cultivated with certain physiologic or nonphysiologic inducers. Although hGC-1 expression was not detected before differentiation, it was expressed after RA-induced granulocytic differentiation, but was not detected after phorbol ester-induced monocytic differentiation (FIG. 5D). These findings confirm the results of the kinetics of hGC-1 expression determined in the two-phase culture system, and suggest that hGC-1 expression is specific to the myeloid lineage.

Example 6 hGC-1 is an Olfactomedin-Related Glycoprotein

Figure 6A:
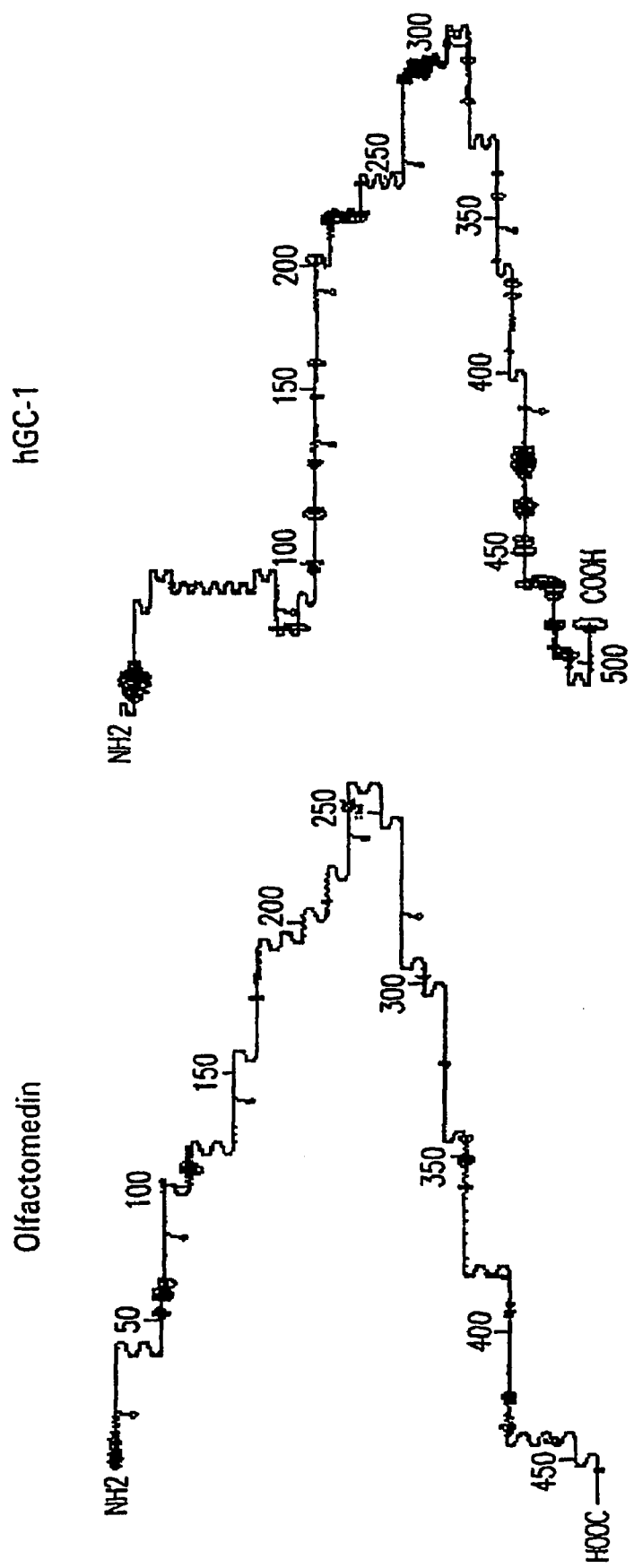
FIG. 6. (A) Chou-Fasman analysis. Predicted secondary structures of olfactomedin and hGC-1 protein: α-helices are shown with a sine wave, β-sheets with a sharp saw-tooth wave, turns with 180 degree turns, and coils with a dull saw-tooth wave. Red indicates KD hydrophilicity≧1.3; purple indicates KD hydrophobicity≧1.3. (B) hGC-1 sequence homology to olfactomedin-related proteins: comparison of olfactomedin from bullfrog olfactory tissue, hGC-1, noelin-2, TIGR and latrophilin-1. hGC-1 showed significant homology to the mucus glycoprotein olfactomedin. A stretch of 233 amino acids in the carboxyl terminus of hGC-1 is highly conserved among all these proteins.

The largest open reading frame of the hGC-1 cDNA predicted a protein of 510 amino acids (FIG. 2B). The predicted protein had a signal sequence, but no apparent transmembrane domain. The mature protein, which consisted of 490 amino acids, had a calculated molecular weight of 55,642, which is in close agreement with the observed size of in vitro translated hGC-1 (55 kDa). hGC-1 contained six potential N-linked glycosylation sites evenly distributed throughout its sequence. Structural analyses of the hGC-1 cDNA sequence demonstrated its protein to be an extracellular molecule with very high amino-acid sequence similarity (65%) to olfactomedin, a glycoprotein found in the olfactory epithelium of the bullfrog (Yokoe, H. & Anholt, R. R. (1993) *Proc Natl Acad Sci USA* 90, 4655-9). Olfactomedin was subsequently found to be expressed throughout the mammalian brain. The TIGR/myocilin olfactomedin-related protein is expressed in the eye and is associated with the pathogenesis of glaucoma. The link between TIGR/myocilin and ocular hypertension and the fact that several of these proteins are expressed in various mucus-lined tissues suggests that they function in regulating specific physical properties of the extracellular environment. Based on Chou-Fasman analysis, hGC-1 was predicted to have a secondary structure significantly similar to olfactomedin, which has a predominantly α-helical structure at its N-terminal, a mostly β-sheet configuration near its C-terminal third, and a region characterized by several turns in the center (FIG. 6A). One significant difference between these two molecules was that hGC-1 is more hydrophobic than olfactomedin. The C-terminal region of hGC-1 also had 46% amino acid similarity to Noelin-1 (Barembaum, M., Moreno, T. A., LaBonne, C., Sechrist, J. & Bronner-Fraser, M. (2000) *Nat Cell Biol* 2, 219-25), a secreted protein that has the ability to prolong neural crest production, 49% similarity to the TIGR protein (trabecular-meshwork inducible glucocorticoid response protein), which has been implicated in some glaucomas (Nguyen, T. D., Chen, P., Huang, W. D., Chen, H., Johnson, D. & Polansky, J. R. (1998) *J Biol Chem* 273, 6341-50), and 47% similarity to CIRL (calcium-independent receptor of a-latrotoxin), a member of the G-protein-coupled receptor family (Krasnoperov, V. G., Bittner, M. A., Beavis, R., Kuang, Y., Salnikow, K. V., Chepurny, O. G., Little, A. R., Plotnikov, A. N., Wu, D., Holz, R. W. & Petrenko, A. G. (1997) *Neuron* 18, 925-37). These analyses suggested that the C-terminal olfactomedin-like domain is highly conserved among these proteins (FIG. 6B).

Example 7

In vitro Translation and N-Glycosylation of hGC-1 Protein

Figure 7A:
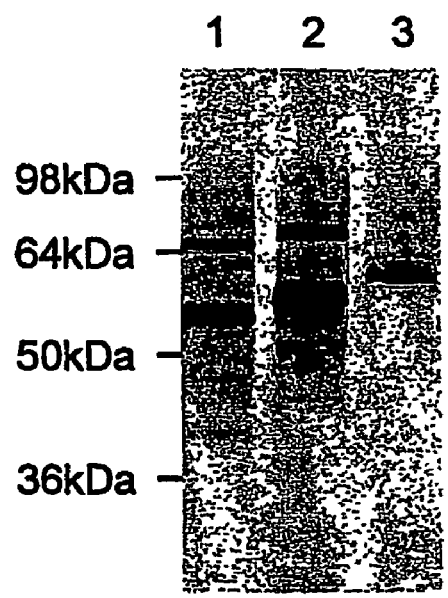
FIG. 7. (A) In vitro transcription-coupled translation and N-glycosylation analysis of hGC-1 protein. In vitro translation products with and without CPMM treatment were analyzed by 12% SDS-PAGE. Lane 1, pCRII-hGC-1; lane 2, pcDNA-E-hGC-1-his/V5; pcDNA-E-hGC-1-his/V5+CPMM. (B) Western blot analysis and N-glycanase treatment of hGC-1. Cell lysate proteins were prepared from either parental 293 cells or 293 cells transfected with pcDNA-E-hGC-1-his/V5, fractionated by 12% SDS-PAGE, and blotted onto Hybond NC membranes. hGC-1 was visualized by an anti-V5 mab. The dilution of the antibody is shown. Parental 293 cell lysates were used as controls (lanes 1 and 2). Cells were incubated in either the presence (+) or absence (−) of the N-glycanase PNGase. Molecular mass markers are shown in the left margin.

To assess ER translocation and early processing events during biosynthesis, hGC-1 was translated in vitro, in either the absence or the presence of CPMM as an ER and N-glycosylation source, and analyzed by SDS-PAGE. In the absence of CPMM, in vitro translated hGC-1, with or without a c-His-V5 tag, migrated as a single band with a molecular mass slightly higher than the predicted molecular mass of 53 kDa (FIG. 7A). In the presence of CPMM, the hGC-1 proteins exhibited a slower migration pattern, suggesting that they may be differentially glycosylated. These in vitro studies indicated that hGC-1 could be glycosylated.

Example 8

Western Blotting and N-Glycanase Analysis of hGC-1 Protein

Figure 7B:
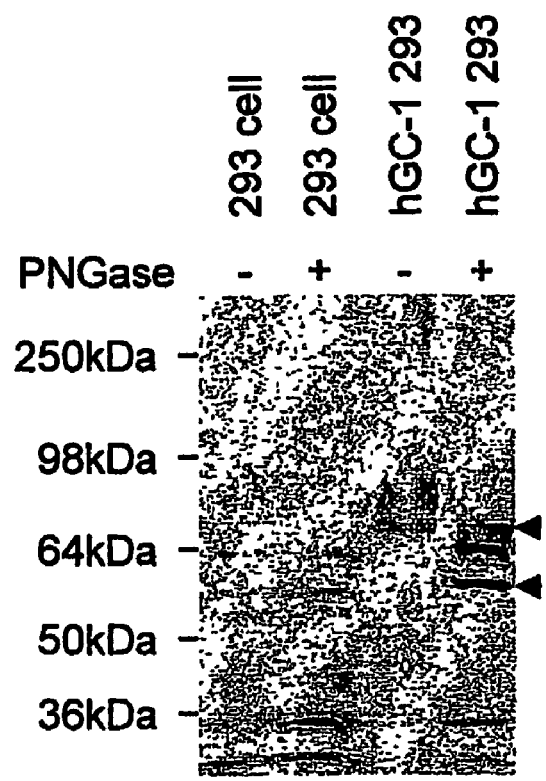

To establish the in vivo expression of hGC-1 as a glycoprotein, cell lysate proteins were isolated from 293 cells transfected with the hGC-1-His/V5 construct. Western blots probed with the anti-V5 monoclonal antiserum showed a major protein band with a molecular mass of ~64 kDa (FIG. 7B, line 3); this size was slightly larger than that of in vitro glycosylated hGC-1 (FIG. 7A, lane 3). After N-glycanase treatment, the size of hGC-1 decreased to 54 kDa (FIG. 7B, lane 4), equivalent to that of in vitro translated but unglycosylated hGC-1 (FIG. 7A, lane 2). This result indicated that the same AUG initiation codon was used for hGC-1 synthesis both in vivo and in vitro.

Example 9

Molecular Studies on Presence and Expression of hGC-1

Studies were done to determine whether hGC-1 was present in and expressed in various cell lines and prostate tissues. FISH, PCR, and RT-PCR were conducted as described above or as described in the literature. The results of these studies are shown in Table 1. The results indicate that, while a copy of hGC-1 appears to be present in the normal and cancer tissues and cells tested (FISH), hGC-1 is not expressed in prostate cancer or myeloma cell lines, or in prostate cancer tissue or benign prostate hypertrophy (BPH) tissue (RT-PCR). Additionally, the gene was found to be expressed in 2/2 normal tissue, but only in 10/66 prostate cancer on a multi-tumor tissue array developed by the NCI (Table 2). These results suggest that while the gene may be intact in most of the tissues studied, hGC-1 is more likely not to be expressed in pre-cancerous or cancer cells.

TABLE 1

Results of detection of hGC-1 in various cells and tissues.

| | | Cells | | | Tissues (prostate) | | |
|---|---|---|---|---|---|---|---|
| | Prostate | Cell lines | | | | | |
| Technique | epithelial cells | Prostate | Myeloma | Colon | BPH | Normal | Cancer |
| Number tested | 1 | 4 | 4 | 4 | 4 | 5 | 7 |
| FISH | + | + | +(2) | + | −(3) | +(3) | +(5) |
| | | | −(2) | | N/A (1) | N/A (2) | N/A (2) |
| PCR (DNA) | + | +(3) | N/A | N/A | −(3) | +(1) | −(4) |
| | | −(1) | | | N/A (1) | −(2) | N/A (3) |
| | | | | | | N/A (2) | |
| RT-PCR (RNA) | + | − | − | N/A | − | +(2) | − |
| | | | | | | −(3) | |

+ = presence of gene found
− = gene not found
N/A = Not available
(x) = number of samples for result if not all samples tested the same

TABLE 2

Detection of hGC-1 Gene in Prostate Multitissues

| Techniques | Prostate Multitissues | |
|---|---|---|
| | Normal (2) | Tissues (with Prostate Cancer) |
| ISH | +(2) | +(10/66) |

Example 10

Identification of Mouse GC-1 as an Olfactomedin-Related Glycoprotein

As described above, cloning of human GC-1 demonstrated that this gene includes the conserved C-terminal motif that characterizes the olfactomedin-related glycoprotein family of genes. To determine whether the C-terminal olfactomedin motif was also conserved in mice, we screened a mouse expressed sequence tag (EST) database using the hGC-1 cDNA sequence. Several mouse cDNA clones with significant homology to hGC-1 were identified. These ESTs were obtained from Incyte Genomics (Palo Alto, Calif.) and subjected to complete DNA sequence analysis. The largest of these cDNA clones contained an open reading frame of 1515 bp flanked by 5'- and 3'-untranslated regions and encoded a polypeptide of 505 amino acids with a predicted molecular mass of 54 kDa. Comparison of the coding sequence of mGC-1 with hGC-1 revealed that these proteins share 93% identity at the amino acid level.

Example 11

Gene Structure, Chromosomal Localization, and Expression of the Mouse GC-1 Gene Using the basic BLAST search, we screened all sequences in the gene databases of Celera Genomics (Rockville, Md.) with the mGC-1 cDNA and identified a mouse genomic DNA sequence on chromosome 14 (Accession: AL390736) with significant homology. Intron-exon boundaries were defined by comparing the genomic sequence and the cDNA sequence. The mGC-1 gene contains five exons spanning over 23 kb, with sizes ranging from 156 bp (exons 2 and 4) to 801 bp (exon 5); the size of the introns ranges from 0.98 (intron 3) to 7.4 kb (intron 2). We localized mGC-1 by FISH (fluorescence in situ hybridization) and radiation hybrid mapping. A labeling FISH analysis with the BAC clone containing the mGC-1 gene gave strong signals at chromosome position 14D3. We examined the expression pattern of mGC-1 in twelve tissues of normal adult mice by Northern blot analysis. A transcript of approximately 2.4-kb was detected most intensely in small intestine, and was also expressed in kidney, spleen, stomach, and thymus. To determine the distribution of mGC-1 mRNA during murine embryogenesis, in situ hybridization studies were performed on tissue sections from intact mouse embryos on days 8, 9, 10, 11, 12, 13, 14, 15, and 16 during development. This analysis revealed that mGC-1 was not expressed until day 15. Analysis of E15 and E16 embryos and newborn mice showed that high-level expression of mGC-1 mRNA occurred primarily in the digestive system. mGC-1 was weakly expressed in the pancreas on day 15, and strongly expressed in the pancreas on day 16. hGC-1 was expressed in the digestive tracts of newborn mice. To determine the specific distribution of mGC-1 within the digestive system, sections of the adult mouse digestive tract were subjected to in situ hybridization. As expected, mGC-1 expression was detected in the small intestine and stomach. Interestingly, a very clear demarcation of the hGC-1 signal was evident in the intestine, where mGC-1 was specifically expressed between the enterocytes lining the villi, but not in the lamina propria or in the muscularis layers. There was a similar, albeit weaker, pattern of mGC-1 expression in stomach. mGC-1 expression during 32D cell differentiation induced by G-CSF. 32D is a murine interleukin 3 (IL-3)-dependent myeloblastic cell line that can be induced to differentiate toward granulocytes by exposure to G-CSF. Although mGC-1 was not expressed prior to differentiation, it was expressed on day 7 after G-CSF-induced granulocytic differentiation. This result is consistent with our findings from the two-phase culture system, showing that hGC-1 expression is specific to the human granulocytic lineage. Thus, these findings suggest that mouse GC-1 expression is also specific to the mouse granulocytic lineage.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated nucleic acid encoding a protein having the amino acid sequence of SEQ ID NO: 4.

2. The nucleic acid of claim 1, wherein said nucleic acid has the sequence of SEQ ID NO: 1.

3. A vector comprising the nucleic acid of claim 1, wherein the vector is suitable for expressing the nucleic acid.

4. A vector comprising the nucleic acid of claim 2, wherein the vector is suitable for expressing the nucleic acid.

5. An isolated cell comprising the vector of claim 3.

6. An isolated cell transfected or transformed with the nucleic acid of claim 1.

7. The cell of claim 6, wherein the cell is a mammalian, bacterial, yeast, or insect cell.

8. An isolated cell comprising the vector of claim 4.

9. An isolated cell transfected or transformed with the nucleic acid of claim 2.

10. A kit comprising a packaging, containing: the nucleic acid of claim 1.

11. An isolated nucleic acid of at least 750 nucleotides with 95% or greater overall homology to the nucleic acid of SEQ ID NO: 1.

12. An isolated nucleic acid having a sequence with 96% or greater homology to the nucleic acid of claim 11.

13. An isolated nucleic acid having a sequence with 97% or greater homology to the nucleic acid of claim 11.

14. An isolated nucleic acid having a sequence with 98% or greater homology to the nucleic acid of claim 11.

15. An isolated nucleic acid having a sequence with 99% or greater homology to the nucleic acid of claim 11.

16. An isolated nucleic acid of at least 750 nucleotides fully complementary to SEQ ID NO:1 or its complement.

* * * * *

SEQUENCE LISTING

<160> NUMBER OF SEQ ID NOS: 12

<210> SEQ ID NO 1
<211> LENGTH: 23324
<212> TYPE: DNA
<213> ORGANISM: Genomic hGC-1

<400> SEQUENCE: 1

```
cctcttttcc tacatgctgg ccatggggaa atcaccactg ggcactataa gaagcccctg      60
ggctctctgc agagccagcg gctccagcta agaggacaag atgaggcccg gcctctcatt     120
```

```
tctcctagcc cttctgttct tccttggcca agctgcaggg gatttggggg atgtgggacc      180
tccaattccc agccccggct tcagctcttt cccaggtgtt gactccagct ccagcttcag      240
ctccagctcc aggtcgggct ccagctccag ccgcagctta ggcagcggag gttctgtgtc      300
ccaggtgagg aggccccaga atctgaatga gctgcattca ttcccttcca tttgcttttg      360
ggtacctgaa tacaatttca tggatggcta gacctgggca ctctaaaaga tttacgactc      420
attttgttaa ctataggtgc cccggaaatg aattaaagcc tcagtaaaat aattaaattg      480
ttagcaagag agacgatatc gcagttctcc agctgggact tttgggaata tctatgcttt      540
agaggaattc tcaaatctgg ctgcacatta aatgggtgg ccgggggac tctaaaagta       600 cagatgcctg ggttctgtac ttaaaaaaat cctacataga tgtatacaaa tcaaatattt      660
taaaaaacct ctccccaggt gattctaata tatagtccaa gatgggaact gttagggaaa      720
gactctgtga gttgcagctc tgggaagttt gtccagttgt tttgctgcct ggcaggatcc      780
cggaatggtg aacagtagcc ctcgagggag tgagagccgc agtgccctag ttgaagccct      840
gaccatttct cttggcctgg tttataaagg aggtgggtgt cagaaataag gggggagtta      900 ctggtctttta gcaaagtgtt attaccagtg gacattcgcc taggggagtg ttcactcttt     960
gcagtcttct ttacagggaa tcttcaggac catttccagc tccaaacaac agtagcaaca     1020
aacaaacaaa accaaaagtc atgcattaca acgaggctgg tacagctagg ctaagtgcat     1080
tgaaggcata gtaagccagt tccgtggggg atgagtcctc tttggatctc ctttaaagaa     1140
aggagaatgg gctggagggc atgagaggtt aggaggtaag aagcagttat tcatttcact     1200
ctgggccttt ctgcgggaac cccactctgc aaacctccta ggctattttt gctaaggtat     1260
aacttggggt gggggagtct tatctgggcc aaagcttctc tctctaagcc tctaggatct     1320
ttcctcacag gtcaggtagc tgcttacatt atcatgcttg aatggaaggg caaatgggag     1380 aaggggggagg aaaagacttt tatttgtttt atttttgacca tcagaaatta cagataataa     1440
aaatgtgata attaacaaat gatttggata gggcctagat agaaacagca gcaataacat     1500
ttactgtgtg tctaataaat gccaggacta ggttaagtac ataatatata tcttttttgtt     1560 gttgttgttg tttgtttgtt ttttgagaca gagtctcatt ctgtcaccca ggctggagtg     1620
cagtggcacg atctcggctc actgcaacct ccgcctacca ggttcaagcg attgtcccac     1680
ctcagcctcc tgagtagctg ggattacagg cacccgccac cacgcctggc taattttttgt    1740 attttttagta gagatggagt ttcaccatgt tggtcaggct ggtctcgaac tcctgacctc    1800
atgatctgcc tgcctcagcc tcccaaagtg ctgggattac aggcatgagc caccgcacct    1860
ggcctgtatt atcttattta accctaagag gtaggtacaa ttaatggtcc cattttagag    1920
atgtgaaaac taaggcttat caaggtgaag tcattagttt taagtcacta agctagcaag    1980
ttatatagct caaaattagt ctgtccattc tcttcaccat gtctgtacat ataggtttct    2040
atatttccaa ggagtataga tgaaaattgc ttatttttta gttagaggag ggaggcttgg    2100
gaatcataag taggcacaag gattctttgc agtcagaaat cagttacata agtttattct    2160
gtgatactca atgattctg gggatgatca gaattgtcta gcactctttt ttggactgag     2220
gttaacaata ataatttatt atgaagctcc atcaccagtc agaaaccagc atttgggtaa    2280
gattatcaac tataataata gaaatgaaaa tacagatcaa gaaacagaga atccagaat    2340 gcctattgtc tggtaaaaag acagatattt aaaagtagat gagacatggt agttaaattg    2400
gacttagagg ttttaatttt ccttttact tatctctccc tggtgagtca gtatcacaac     2460 tccaacttttt tttttatact ggactaggag tcaatttcac tatcaaccta attttctggg    2520
```

```
gctggctgtc agcttgatga gctctttgga aggtggtaga aaaccctttt ataactgtca   2580
ttgagtaagt tccaaacata tcattttctg tactttgaaa atgttgagta ccattatttt   2640
ataccttgaa tctttgctga cacttagcct tggctactaa ttagagccag ttgcaacatt   2700
aaatcacctt aaatgtgagt tgcaccttct gctgtaagca ctcagagtac tctctgcctc   2760
agacgtctcc ctcctgagga ggggcctctg caggtcctc aattcacaag actaggaaaa    2820
gcctcaatgc tcactccaca gagtaactgg tatagttgga actgcaacga gtcacgtgtt   2880
ttcttgtcat caggctacaa ggctggtttg aaaaaacaag tagggctttc agagtgacag   2940
tgggcctgat tcctgggcag aaattgagtc ttaatcatct ccctaaagcc agaacctggc   3000
atagtgtaga catcagtaaa tgttaattga acacgtgctt agggaaaacc taccaatata   3060
aggtgtcttg tgaggtactc agggtcctat ttgccctaca aaggggaat cgcatattct     3120 tccaaaggcc aaggggacaa gctcttgtct ttgtctccca tccccatgc ttcattcatg     3180 tagagtttgg gcattcaccg cagagagaga ctcatcacca ttagcttcat tgtctttgaa   3240
tgcgaggagc agaaatatct ctaatgggag acactgatca aacttatgga ccattttgat   3300
gtcagctgag catgctgggc tgatgataag caggatggaa gctggggag tccacagctt    3360 tgggacagag atgttcaata gaaaccgatg gaatggctga cagcagggct cataattact   3420
tgtctgtctt tcaagtgaac ttcaggacta aaagttgtta gctagtggtt cctaattgac   3480
tgtctagaga ttgcttgatg atatccactg ttttctgagt tggcagaatt tttcagagaa   3540
ctctgagaat ggcccaaccc tgtttgtgca gctaattaaa ctccccttgt taaaatgcaa   3600
tgcaagattt ttttttttgct agactgttat tataataagc tatttcttca aaagtccttg   3660
atatgtcggt cttttctgta aaagccttgg catgcttgag ttggagtctt tctatctttg   3720
gagaaatgag taaagctggt ttcaagggaa gctggcctct ctgataggtt cctggtgtat   3780
cttaccgagt ctttattcat ctctggcaaa gacccttccc ctattcaaac cctgctgtcc   3840 accectatgt tcgacataaa tctgcttgtt tctcctccct actcctgaac tgtttcccac   3900
gtagggatgt gattggaaaa gaaaattgag accaaggtaa taaattttga ctaaacacat   3960
aaaaaatatg attggataca cacacatatt tttttttct gctcatcttg aaacttaaat     4020
taaattaaaa acaacttaga tgcaaaagcc ttgattggcc ccgaggccag tgataaaata   4080
agtcttcatt atagaagcat ctagacccag cttgatcagg cattatggag gttggtggcc   4140
attaaatgca caggacccat tacaccacct gcagctggct gacctgaact ttgagagaca   4200
tggccagagt cacttctggc tctgaagacc attgctgtct ccttagaggt ttcataaaaa   4260
gtcccttcag gctgatgttc cacaggtgag cttttggggttg gctttcagat gagatcatta   4320
aaaggcacag caaattggct gccaagggtt actctgtaag gcaatagtag taataaaaaa   4380
atgttaattg tgctgggatc tccttgggga agttcaaagg ggacaaaaga aaacaggat    4440 ctttcaaaag tgtcatttaa aaatatgcgg tggcactgaa gtgtgagtct gaatatctta   4500
aatgaacata aaatatttta aaatgacttt ttctgcaaat ggtaagctgg aaaaaaactt   4560
ttattaaaaa aaattgcaca aaaccttcaa gctcatacgc tattcacttt ctaacaaatg   4620
gctggttccc atttttgaagg atgttaattt gcaatttccc aggcgatgag aggatatgaa   4680
tttgcatcat atattttcac tgtagcccac atctttggtg attccctcat tctgatgaaa   4740
aggaattgga ttgggttggg gtgaaggtga ggaagagaaa atgagcagta gaaggaaaga   4800
gaatgtgaca ttttcagatc acctactctg tgccagggac ttggctcaca ttacttcgtt   4860
```

```
aatactgagg acaaccctgt gaagtaggtt atctctattt tacagatgaa ggaactaaga    4920
attaaggaga tttcacatct agcaagtgct agaattgaaa ttcaaactta gcactctcat    4980
agcttcttta tttcccttc cttgcataga gataggaata atctccttta agactccaga    5040
atggccgggc gcggtggctc acgcctgtaa tcccagcact ttgggaggcc gaggtgggtg    5100
gatcacgagg tcaggagatc gagaccaccc tggctaacac ggtgaaactc cgtctctact    5160
gaaaatacaa aaaattagcc aggcgtggtg gcgggctgta gtcccagcta cttgggaggc    5220
tgaggcagga gcatagagta aacccgggag ccggagcttg cagtgagccg agatcgcgcc    5280
actgcactcc agcctgggcg acagagtgag actccgtctc aaaaaaaaaa aaaaaaaaa    5340
aaaaagcctc gagaatgggg aatcttcctt taggtaaagt ctgctggcgt agtggttttc    5400
gtacaaccag tggcgatgtg gctaaacgct gggtggtccc cacctgtgaa acaaagctg    5460
ttttagcttg tttctatgat tctattcatt tatgtattgg actccactta cttgcctgta    5520
agtactctcg acaagccaat ttctgtcact ccagttgcca aaagctcaga ttccagcttg    5580
ttattgatgt tcaacttgtt attatttgca gttgttttcc aatttcaccg gctccgtgga    5640
tgaccgtggg acctgccagt gctctgtttc cctgccagac accacctttc ccgtggacag    5700
agtggaacgc ttggaattca cagctcatgt tctttctcag aagtttgaga agaactttc    5760
caaagtaagc attttctttt caaacaatat cttgataaag agaaacaaaa caaatgtgt    5820
tttaatttag gattttataa gcaatcattc ttcactatca aagacatcac gttttattc    5880
tatggtgatt ttagtattta ttttatagga caccaatgga gttcttatta aggcagggaa    5940
aatgagagca caggaagaaa gtggggttca aattgttcac gccgtggata aactcactat    6000
agtattgtgg tacttaggca gttggaaaga agccttgagc tctccttgca aaccccaacc    6060
tgcaatttt attttgttt gacgctgctt cttccttttg gtcttctagg tctttcctca    6120
agctttgctt tcttttcttt cttctcctct atcccctta gttctattct atctcccttc    6180
tcttttcct tttcttctat ttctattcca ttcctgcatc ctttagtttc ttatttctct    6240
tgcctcaatc cttgccctta ttcatcccctt ctaatctctc ttttcctttc ctggttaatt    6300
cttttttggg ggggacattt ttgggtattt tcttactttt agatgatctt ttttttccctc    6360
cttcttttcc cttcctccac ttccactcct tcaaatcctc tccctctcat cctcctccct    6420
ccctctctct ttccttaac ccttttttat ctttacaaat tgctcacttc cttctctctc    6480
ccctcactc tcttttttg tgacaataag ttgtagtctc ttttattttt ttctattttc    6540
tccaagtgaa atccaaggtt gtagtctctt tattttaat cttattttt tttggtgtat    6600
agtaggtgta tgtattaatg gggtacatga gataccctga gacaggcatg caatgcgtaa    6660
taatcacatc atggaaaatg gagtgtccat cccctcaagc atttatcttt tgtgttacaa    6720
accatccaat tagactcttt tacttatttt aaaatgtaca atgaaattat tatggactat    6780
agtcaccctg ttgtgctgtt gaatactagg tcttatttat tctttctaac tactttttatt    6840
ttttacccctt taactatccc cacttccatc ctcaccctcc atctctttct tgatggttat    6900
cttctattgt ctcagcagga acattacatt tgatgtgtcc aatattagac aaaaattgaa    6960
ggcttccctg ggaatttgaa tcaagactaa taggtttctc agccttggta aaaacactga    7020
cttgaactct gattactgtt ttttctttta gccagaggaa gttatcttaa agggtttgcc    7080
tttctctggg ctggctggag caatgtgact tggtgttcta gttttgactc cttccacctt    7140
ttcagcccaa gttaaaaatc aattagaaaa gttcctattt tctgcacagg tgaagtccaa    7200
gctagtctat aatcacatta tgcattattt aatacaactc cattaattta caaggagctc    7260
```

```
tggctttact gcaagattca gaataagttt tcctaagaaa tttgagcttt gccacctcaa    7320
catccaacat agttatcctt taaaacaaaa attatgatga ggctgagacc ctactttcag    7380
cctgaattgg tagataaata ttctaagttt aaatgagtgt ccaggaaaat gtgtttgact    7440
actctagaaa cctagctgct taagaaatat aatgtccttg aattaatcag tggaaaaggc    7500
acagcattaa attataaatt ctaaccatta atattcatag ccttattcca gcataatcaa    7560
gtacagataa gaagttatgc ataaaaacat aacaagtaga ggaaaatcct aggtaaagat    7620
cttttcagtt agagtcattt gctttgaaat agtggaaact actgatttac atgttgtctt    7680
tgctggcagc agtgtgaaag gcagtttgaa accttatgtg ctccagggag agtatgtggc    7740
ttgccaggtt tgtgaatatg ggacatttaa ttccaatact gtacgggggg ctggtaacat    7800
ctgctttgct aatgacagat agggaagaag tgcagaatag gtgggaaagt tttagttctg    7860
aatgtgtcgg tggctgctct gatcccaaaa aaactgtgat tgtggcctaa gaaaaaagtt    7920
tatctgctag ctaggattta tataatcgat ttagtgtgac aggtgataat aacaacaata    7980
atagtagcag tttgtttgtg cttttttcaaa tgcttccagt tctattctct cctctcaagt    8040 aacccttaa ggcagatagg ccaggtgttg tctctcccat tttagagaca gtaaaactgc    8100
agttcataaa ggtaaggaga cttgcccaag gtcattcctc tcttggctgg ttaagccagg    8160
tcagaattcg agtcttcaaa atcatctcaa ctctctttcc tcttggccat gctgttagca    8220
tcctccaagg taggcccagg aagagatgca gtagtaatgc cttcaaatcc aaagttatcc    8280
ctttagctga gggctttcga atttccaagt gagttattac agctgtccct aggttgcctt    8340
gaaaattgtc atttatccgg gggcctggga gaatgcccgt ttaggacagg ccagtagaaa    8400 aggttttga ctgccttaca ttgattcatt gtctgtcagt acacagagaa gacagggagc    8460
tgcctctgca taagatgctg aaagcatttt atacttttct gttgtttacg gtatgtcctt    8520
ttgtgactat acttaggaaa gggatggcac aaaaggcagc tcaggatttt ctctttctct    8580
ggaggcttat ggtctttggc atgagttatt taatatgaca catttgctag tagatcctca    8640
tgcacgggaa ggttgaggca gcctaggaga cattaaggca acccataaag aaataacatt    8700
gattgagccg tatttgtata gtgaaatata ataaattaaa aggtcagatt ggaaaatgct    8760
gaaattactg tttctctatt aatttctata attcataggg cctccattaa ctaggcactt    8820
aacgtacatt atctctagtc tttatgataa tcttgtaagc tcagtatcat tacccccagt    8880
ttacaggaaa ctaagggtta aagaaattaa gtgatttgcc cactaagtac tgaagttaga    8940
tttgagtcta gttgggtcta gctccaaagt actttatatg tctttacaat cactccaggc    9000
tcaatgaacc ctgttacgtt tactttgaaa catatattga aaatagtagt atgttgcaaa    9060
gtaaacgtac ttatttcaaa tagtctggcc atagttataa tcacaggttt tgagagactg    9120
gcagaaacat gaaccagatt aattctttag cttgctagca ctacccctt atttattaca    9180 agaccacatt aattataagg aacaataaca ggcaccctca atcaacgct cacacaaatt    9240 ttattcctca tcaatgatat agtatgtgca taacaagcaa aataaaatgg aagctgtgaa    9300
tgttaggctg gtggcttaaa ggctcaacta aaacatagat gagccatcta gtgctcagac    9360
ttgtcatgat gaggagcttc gagataaaga tgttgacaca ggacgtgtct cctcaaggct    9420
agacccatat tcttgataga atgtttagca gcgtccctgg tctttagatg ccaatagcac    9480
tcgcccaccc cccagttatg agaaccagga caaaatcacc accactaccg ccctccctcc    9540
atttagaacc acttttctag atcaaaatac agccataggt cagctaaaga cagggacatg    9600
```

```
ttctgataaa tgcatcgtta ggtgatttta acattggtga acgtcattgt atacttacac    9660
aaacctagag ggtgtagcca actacacact caggctatat gatatagcct attgccaggc    9720
tacaaacctg tacagcctgt gactgtactg aataatgtag gcaattataa tacaatggta    9780 agttttttgtg tgtgcatata tatctaaaca tagaaaaggt acagtaaaaa tatgatattt    9840
ataatctcat gggaccactg tcatatatgc agtctgtcat agacaaaaat gttatgcagc    9900
aaatgactgt attttccaga agaagaaaaa aatgcagaaa gtgccccaag tgccagatgt    9960
gggactggag gctcccaggc aggctgggct gcctctccca agactgcacc tcccaggagg   10020
agctgacatg tggtcagcat tgtccacgca ttcccaaagc tacagattca tatatgtgaa   10080
aagttcatat gaatgattta cttaaattag taaagttcac actctgaagt ctttctggcc   10140
catccccaag ctcttttgtg tcttctctaa ctccatggat gattgccatt ttcctgaaca   10200
ccactgagca tcctttaagt gtcagctgaa gaaccttgag ttttttcctc aaatggatct   10260
ttacagaccc ttcattttgt ctgcaccagg gcaggcacac cacacatttt tataggtaac   10320
aaactccaga atatgccttg cttttttttg tgaaaatcta ggagaaccac attttattta   10380
gcagagatga cagttgaatc actcattttt gtagaacaac agctgcgatg tgccaccaaa   10440
atgttccaga gaagctgagg gtgtttcatt tgttccaaga gctggcaagg ccaaatgcca   10500
acaagcatat ttatttctca aacttccatt tctgtaatgg attggcactt tatttatttt   10560
tatcatagtc aaggttttat gcctgagttt tgtagacact ggaacctggc agccctatat   10620
ctgcagtgca cttctcaggg ggacttgtta ggttttatat atagtgagcc ctccatagcc   10680
ttggttccgc atctgcagat ataaccaaac tcagattgaa aaatttcacg gaaaaaaact   10740
aataaaaata accatgtaac aacaggaact atacaaataa aaaacaatac aacaatgatt   10800
tatatagcat ttacattgtt ttaggtatta taagtaatct agacttgatt taaagtattt   10860
gggaggatgt gtgtagattg taggcaaata ctgtaccatt ttctgtcaga gtcttaagca   10920
tccttgaatt ttgttattct tgggaggttc tgaaaccaat ccaccatgga tactaagagg   10980
tggccgtata tatgtttttaa cctccctatc caccaaaata tcaccagctt tgtcatcctc   11040
cgagttatgg tacatccaat ggcagtgagc atcagttgcc cgaggagata cactagcagt   11100
gccaaggact gttttttcga ctttcattaa aatcctttt gcctgaagcc ctagcccttc   11160
aggtctgtgg tctatgagtc tactttaatt tgcacaatgg ggttaagtgg aagggctgaa   11220
atgacagaag ttaggattgc ttttggtata agaaggatta aaggccaaca tctggctcta   11280
aattcatcca ggcactgtgg atcagctact tgatattagt gtagttttgg gaaaagtatc   11340
acttcagttc aaattttaa aaagcatata aagccagcaa cttatttaat gagcaggtcc   11400
ttaaaaaagc catggcattt tctttagaga tcagacacag aaagaaccac caactgtgtt   11460
tattaaaata tccacttgga tattccaatt atacactaaa ctgccaaggg aattttggga   11520
agtattttaa cttaatgatc agacattcaa atatatgcaa caaatctgta atttaaaggt   11580
ctgattgcaa taatcagttc ttggaataaa tgtgggtgca cttaatgaaa tgtgtactct   11640
acagggcaca cacactcaca tattgtgtag taggttggat ctctatgcca ctttgtaaaa   11700
ggcagagggg atcaaaacta attgtatatg gcgatcaaag aaggaattcg gcatagcgca   11760 tttctcccctt ctccagaaaa tacttagatg tagagccatg tttctaaatg gaaggagggt   11820
ggtgttggcc gtggcaacga ttttgtcccc agggaacatt tagcaatgcc cagagacatt   11880
tttggttatc ataactggag agtggttgga tgcaactggc atgaagaagc cagggatgct   11940
gcttaatatt gtgtaattca cagcacaacc cccacaagaa atgacaatcc agtcccaaat   12000
```

```
gctaacagtg ctgaggttga gaaacaatta gagtaagtgt gttgaaggga ggagagatgg    12060
caagagacta tgatacaaac cagtttagtt tggggagtta atgtcttcaa acattaaaat    12120
ggagattaag aaaaaagggc tcaatatcac ttgatcatta gagaaatgca aatcaaagcc    12180
atagtaagat accatctcat accagtccag aatggctatc attaaaaagt aaaaaaataa    12240
cagatgctgg tgagatggca gaggaaaggg aacatttata cactgttggt gggagtgtaa    12300
attagttcag ccattgtgga aagcagtgtg gtgactcgaa gaactaaaaa gaactattat    12360
tcaacctagc aatcccttta ctgggtatat gcccaaagga atataaattg ttctaccata    12420
aagatacatg ggcgtgtgtg tacattgcag tactattcac aatagcaaag acatgaaatc    12480
aacctaaatg ctcatcaatg gtacactgga taaagaaaat atgggccata tacaccatgg    12540
aatactttgc aaccataaga aagaatgaga tcatgttctt tgtaggaaca tggatagaga    12600
gctggaagcc attctccgaa gcaaattaac acaagaacag aaaaccaaat accacatgtt    12660
ctcacatata aatgagagct aaatgatgag aacacatgga cacaaagagg agaacaacag    12720
aagcgtactt gagggtggag ggtgaaagga gggagaggaa caacaacaaa aaaatctatt    12780
gggtgctagg tttagtacct gcgagacaaa ataacctttta caacaaaccc ccatgacatg    12840
agtttaccta tataacaaac ctgggtatat accoctgagc ctaaaacctt tttaaaaaat    12900
ggagattaaa atatacctgc aaatgatgat gctgaagcaa aattatgttt agcctagcaa    12960
agtataaaat ctacctccct tcaattggag taataagttc tttgtatatg gatagatttt    13020
aaaaatctag ttaaatgtat ttttgatcta tttatttaca aaacacaatg attggcaaga    13080
atcaaatagt tctcaactca agggctcggt agtggaagaa gatggtgtga tactactcag    13140
ggaattggct tgaaccttt gattttcttt caggtgaggg aatatgtcca attaattagt     13200
gtgtatgaaa agaaactgtt aaacctaact gtccgaattg acatcatgga gaaggatacc    13260
atttcttaca ctgaactgga cttcgagctg atcaaggtag aagtgaagga gatggaaaaa    13320
ctggtcatac agctgaagga gagttttggt ggaagctcag aaattgttga ccagctggag    13380
gtggaggtaa ggagtgaact cacttcttgg taaattaata ataaactccc ttcagtgact    13440
gtaagcaagt actagtacca ggaagtgaaa ctatctcttc caacttctaa ttctctactg    13500
tctcatggcc acatggcata tcactatgtt ctgttttgga taagggcatg tgtttgaata    13560
gtaagttaag cacattggga atgtgctgac ttaggagcag atgttgtcta atggtcagaa    13620
tcctgcccca gaataaaatg cccttttcaac ttctctgaaa aggagctggc ataaagttga    13680
acaacggttc atggccaagc tatatgaggt gtcttctctg ctctagattt atcctcatgg    13740
aactagaaat ccacaatata cctgattgtg gtaaaattgc taggtttgtt tctccttttg    13800
aataacctgg aatccttctc tgcaaactgg aaaccccctt taagaaattt cttgtatatt    13860
tctgtaaagc cttttaagat ctgtggataa agaccatcac attaacgtta tggttgggta    13920
atttatatca acaaaaattt actagcacag tcatgacatg ggctataatt gagaattcta    13980
gttacgtatt ttagaattta agctttctct ggccctcacc attcattaga atcttaatta    14040
taatacaaca tgagtaaaca caagtttata ggggaaggtt attagaaatg aactttaatg    14100
gacatttgtg gatgctgagg atgagcttgg gctctattat taaagctatt aaaatctttg    14160 ccatttttctt cttgtcacac acatctgcct gagatctgac aggcattcat gctaaaccat    14220
aaaatgtatt cttccaaatg aaaccattca gaagaatctc tggtgtattc tctggcaatg    14280
tttcactaaa tgacaaattc agccctggaa tgttatgaa agaaattgca ccataatata    14340
```

```
aagtcactct gaattttat  ttccttagat  aagaaatatg  actctcttgg  tagagaagct   14400
tgagacacta  gacaaaaaca  atgtccttgc  cattcgccga  gaaatcgtgg  ctctgaagac   14460
caagctgaaa  gagtgtgagg  cctctaaaga  tcaaaacacc  cctgtcgtcc  accctcctcc   14520
cactccaggt  aagcatgcca  gttttttaa   ccacttgtgc  cagaccccat  aaggagctgt   14580
gagtggggtg  gggaagggat  tgggattgc   aatggtgaaa  gaagaaggtg  ggttgttttt   14640 tttttttt    tttcagttct  cagttttctc  ttccatgttt  taaaattccc  ttcctcccaa   14700
gtattctaca  tgctatcata  ttctgggttt  caaagaggaa  gagcacaaac  aatgagttga   14760
tttaaagcaa  aatccacgag  ttacacgtat  tctctttgca  ttttctaaca  gggaacaaaa   14820
atctctatgg  tgatggaggc  cctatcaggg  gcctcagggg  aaagcctctg  gaatctgtgt   14880
gtggcatcca  ctttcctgtg  gagttaagga  ctgattggct  cacttatctg  atgagctggg   14940
tttatgcctt  tgatgctgcc  atcttctctc  tctccttctg  tttctcttta  attttttctt   15000
ttttcttcct  ataaatgcat  gctgagcacc  tgctatattg  tgtgtcctga  gattcagtga   15060
ggattaaagg  aatgacccca  catatcatgt  gcttgtgggt  gtgtcttgcc  attcctcatg   15120
gattgtgagt  tcttggagta  ggggtggcat  gttcgtcttt  aatgaattct  cattggggtt   15180
aagtacagca  cagaggtggg  tgttctgcaa  atatacccat  gaacagaggc  agtggagtgt   15240
agggtacaag  aacatagctt  tagaattcca  aagacctgag  cttctcagct  aggtggctgc   15300
agcaaaaagg  atccttaata  tcctcatttg  taaaatggga  gaataatagt  gcctgccttg   15360
cagggtggct  gtggggatta  atgagtcagt  gcttgggaag  ctcggaacct  tatgatcggc   15420
actcacacgc  tggcaatgga  tattgttaat  aatgttgata  attgaagcga  aagccttgca   15480
gcaaaacaaa  agcagtgcca  gattactgtg  ccctgcaatg  cattccttca  ggtaaactaa   15540
agcctctcag  ccacagtgtt  cagccccatc  ctttagagat  atcaatgaca  cagggacctt   15600
ctctctgcag  gtcctgagca  tcttagcctg  agtggggact  gtatcttttc  atcaaatcat   15660
gcaatccttt  tatttttatg  aattccaatc  ctcacacctg  ctttctttta  gactgtgttt   15720
ctggattatt  gtcattgtaa  ctgatttttt  aaggcttcaa  ttattaaata  ggtatagcca   15780
tagatataag  cctcttggtc  ttcttcaggt  ggatttttt   cctccctctg  caaataggag   15840
tgtgtcctac  tatgacaggt  gtcatctaat  ggttagaatc  ctgccccaga  atgaaatggc   15900
ctttcaactt  ctccagaaag  gaggtgacat  aaatttgaac  aactgttcaa  atttcgcatc   15960
ctgcatagga  ggtttagggc  agacaacatg  gtctgtcctc  tgtaataaac  taaggctaaa   16020
tttagtctgg  gattagtggt  gcaaaaatgt  agcaaatgag  agctgtttct  ggtggaccac   16080
agaggactca  ctgaggcaga  ggctgaagca  atgacaactc  ctgataatcc  ctgaacgagc   16140
tccccaacac  cccttgcaaa  tcctcctcat  ggaatagatt  tttctggcac  aattttctat   16200
gcatccctta  gaatgaggac  attttagatg  aaggaatatt  cagggccatc  taacttagcc   16260
tcgtcttgtc  tcagaggaga  agacgtggat  ggtaagaacg  ctgcttttcc  tgaggccaca   16320
caagtagtta  atgacagagc  agaagctgca  aggcaagggt  ctttgctccc  tggtcagttc   16380
aggaccgaag  gtgtcaggca  gcagtaatcc  aaggacaacg  gtggggagaa  atgcattgc    16440 ttagtatcca  gggaagaaaa  caagtgagcc  tgttgggttg  ttttgttgg   attttttt    16500 tcccagaact  ttcccctagg  ccctcacact  tagacttctg  tgatccatcc  tagcccagct   16560
gtgttgttta  agcaaattgg  acccagattt  ttactcactt  tcccacaacc  ttggctgtac   16620
ctgaatccct  gccaagccac  ttggctctct  tccagctttg  ttcatattat  atttatgatg   16680
tttatattaa  actgactttt  ggtcatgttt  ttaaatcaat  ttctttcact  tgctctcttt   16740
```

```
                                                      -continued ctgtttggat tggttgataa tgcagaattg gaaaatcccc aagcaccaca aacttgtgag    16800
cctgtggaga ctttaattaa agttattctc tattatggga ctttaaaatc tggcctgtct    16860
gcttttttca ctgcagagtt gcacagaata aaaaagacta tatgcaagtc tcagctctaa    16920
agtaactctg cgctctctgg gcccctccc ttatagctac agtttgctga cccagtggtc    16980
agcttgaact tagaacaagt gaatgtatcc caggttcaat aaaatatgct tcctatttgg    17040
tttttgctac aaacaacgtc ctttttctgc ctcatttcat agaactttct aatctaaaat    17100
aattggcctt ctactcatta acttttttcc cttaaaactt cagtctgtct ctgttttgcc    17160
tgtgaatcta aatgactgta tataggccaa atgtgatcgg gtgctcaggg gttgatctcc    17220
agtttgcttg gggatgcaag gttctgtgct ggtccatagt gatgctcagt aagtagctga    17280
tgattaaatg gggtctgaaa gaaatggggt gacctgctaa aatctcaagc ttagggaaga    17340 gcccacatgtt gaacagcata tatccaacac ttcagagtca atttagtctt aatcatttta    17400
tgactatgat tgttttaatt gcctaattct tataagtcaa tcatattctc ctcctggctc    17460
aaacaaagtt cagttgccca gttgagagag tgcattaata gatccaagac taattttcct    17520
ctgtaggcat ataattattg gcttcaaaaa aatgctacta accatgatac ttttaaaaag    17580
ccaagtcaga atattttaaa ttctcatgat tatggcttcc tcaggtattt tcagagtacc    17640
atggtgccat ctaatgaatt gcatgatgaa gagagtgcca accaaggcta aacttctata    17700
gagggttcct caaattatgt tccatggagt aaatgccagg cttttgaaa aaccagatat    17760 gtagcagggt agaaggctag tgttttataa ataagggtaa gctgagttta ggtgacttga    17820
ttaatctttc attcctttat tccacaaaca taatttggtg ccactgtgtg gctggccctg    17880
ttctgggtac tggggttacc agcatgagta aagaaacctc cagaagccac tatctaggaa    17940
atgagacatc taaacctcca gttgtaacat gatgtgatta tattgagata tttaccattt    18000
actgagtaac atttacatgt cttctctgta ttttcgtaa ctattttgca gagttggtat    18060 tattttttctt ctgacatgag gaaactgagg ctcagaaggt taagtaactt gctcaaggat    18120
acacaactac tgttggaatc aggctttgaa ttagaatctg tctagtagta ttttccatac    18180
taggctgcct tccatagctg ctctaacaga gaggtgcacc tgtgatttct ggagtgaaaa    18240
gaaaattcca acaactcacc tatctgctta acaccaaatt attttgctt ccttggtagt    18300 ggagtaggta aaagggtact gttgctcctg acagttctgt gctgtgtgtt ctcttccacc    18360
agaaaatgca aaatgattca atggtctttc agaattcttg gatcatgatt gggcaatggg    18420
ctgttgccca agtgtcaggg tgaaattggg atggaaactg ggtatgaagt atggaatgaa    18480
gtatgtctaa gaccttgaca tgaaggaagg ggctggcaag gagcatgaga taagggaggg    18540
tggtgagaag ctcagtgaag atgggatggg gggatgggga ctctgaggaa cagtgggcac    18600
tggactggct gtcagtttca gtatcgtgtc caagatggtt tgctgccagg agtcgaggaa    18660
gcccgccata gcattttcc tggtctgaca ttgttgtggc cacatttgta gcattggcag    18720
caatgttgag ttctcatccc catttccact tcctttctac cacagccggg gccctaaaaa    18780
tagcccttta tccttaccca tagaggataa aaggaggata acaaatgaac aggaaagtgt    18840
ttaggaatgt ttgggaggtg agaaaaacaa agtttcatac attttaatat ttacactggg    18900
caatttgaat tttctggtca acttatgaaa tgatgagcca ctattactat tagtagtagt    18960
aacaatagta atagtactaa tactattata ctaataataa tgcaattagt tttatgataa    19020
tagcagtagt aatagtaatt ttttgagaag tttattttgg ttccttcatg tctaaaaatt    19080
```

```
tccacatctg gggacagaat agtttaacct cttggtagtg cttgaataag ttatatgcat    19140
catcaatttt ccttaaatat tttgttgctg tcggtttggg atattttctt ttcaggaagg    19200
caagactcaa tgaagcaaac aattattgtc ttccaacctg aaagaaaaaa aagtgactttt   19260
cctcagagtg aaatgtagtt aaataaataa gttctcagga agatacttta gctagaaaat    19320
ccagtttgta gcatatggaa acttgaacag ttttttgttat cattaaactg aacacaccgc   19380
taactttatt ttaataattc atgcattgtt tcataaacaa aagcaaacaa gcattcatct    19440
gagagatcac ttttagtaga agaaataata atttataatt ttatttatta tttcttcagt   19500
ggagaatagt ctcttggctg aaaacacgtt gctttttat ttatgaaatg gcacatgcat     19560
tattaaaata aacctgtgac tgtgttctgc ttaatgatat gcaaaattat ttgaggttgg   19620
atacagagtg gtttcatttc tctacctgtt gtatggttgg ctggctttct caccaactgt   19680
ggatttatga gagcatttaa ggagcatata tttaattctg gaccaaaaa gccccagccg    19740
attggaaaaa taaaaacaga atttctagta atggtttcac ctttgagcag tccttgggtg   19800
aggaggatgg ggagggaaag catttagcaa ggaaaggaat gggtctttcc atattggaca   19860
cagcagagac ccagagacaa aggctttgct ccccccttccc cgcctccatg ctaatctcag  19920
gcaattcttt ggagctctgc ttttggctcc agctcacctc atgttcctca atggctctct   19980
gagtccctgc aagtatttca ggccaaatcc aacaattcag gttctgctcc tttcctgtct   20040
cacctgctct gctctgagca gcaggacgag ggaaaatgac ctcaaatata cttgaagttg   20100
ggttttcttt gttatccaat aaaccatctc atgagttttt ttgagtgtta agatcccaga   20160
aaatgtgtgt tcaactcttt ggatagttat tataaaaata ctggaggaac tttatttat    20220
ttttatagct cataaactcc tgggatggca ggcatttcag cgggagtaca atgtgaaggg   20280
ttgatcgccc agactgagtt atttacccaa gtgttacagg gaatgtagat tcagtggacc   20340
agtgaatctt gtcccacttg attgtacaca ttgtgacaat gacagtgtct ggatggaaag   20400
atgaaatact tgcatgtcat tctatggcac aatagcatat gggttatgaa cagcaggact   20460
caccatgtaa ctctgcagca ggacggtcag caagtgattt attgatgggc tgtgcattgg   20520
gtacggagca ggcaatgttg ccccaaaata actttatggc ttctcaaggg tgaaatccca   20580
ccattatagg accatctttc tggatctata aaatgctata tttaaaacat cctcttctga   20640
gaatagctta aagcaggatt ggtacctggc gtggatgtgc aattgggggt cccaaggaag   20700
gggagagtga ggaagggcat gaagccttgc ctgggaaaat cttctccctc atcactattc   20760
tttctgggat agatttctat aaatcttgtg gatttataga aatagggtag gattgtggaa   20820
taatcttgct tccttgattt tgctataaga aaaacaaaat aagataatat ttgcaaaatg   20880
ctttctgata gaaggaaata tattaaattc accaagtctc cctttcctct ctctgggcct   20940
ccaaactttt taaatatagt tcttgctggt ttcattattc ctattttcca gattgaaagc   21000
ccacccatgg aaacagaatg tagttctctg tagagctgac attgggtttg cattgagact   21060
gaatgcactg aactaagagg aggtttggct cttctccatc agaaccactg ttgttattga   21120
accttgacag gaaaaatatt tatagattcc tttggtgctt aggatattaa actatttgta   21180
tcctgtcatt ccttttctct aaaaatgcct ttttattttc ttgtttgtat agggagctgt   21240
ggtcatggtg gtgtggtgaa catcagcaaa ccgtctgtgg ttcagctcaa ctggagaggg   21300
ttttcttatc tatatggtgc ttggggtagg gattactctc cccagcatcc aaacaaagga   21360
ctgtattggg tggcgccatt gaatacagat gggagactgt tggagtatta tagactgtac   21420
aacacactgg atgatttgct attgtatata aatgctcgag agttgcggat cacctatggc   21480
```

-continued

| | |
|---|---|
| caaggtagtg gtacagcagt ttacaacaac aacatgtacg tcaacatgta caacaccggg | 21540 |
| aatattgcca gagttaacct gaccaccaac acgattgctg tgactcaaac tctccctaat | 21600 |
| gctgcctata ataaccgctt ttcatatgct aatgttgctt ggcaagatat tgactttgct | 21660 |
| gtggatgaga atggattgtg ggttatttat tcaactgaag ccagcactgg taacatggtg | 21720 |
| attagtaaac tcaatgacac cacacttcag gtgctaaaca cttggtatac caagcagtat | 21780 |
| aaaccatctg cttctaacgc cttcatggta tgtggggttc tgtatgccac ccgtactatg | 21840 |
| aacaccagaa cagaagagat ttttttactat tatgacacaa acacagggaa agagggcaaa | 21900 |
| ctagacattg taatgcataa gatgcaggaa aaagtgcaga gcattaacta taaccctttt | 21960 |
| gaccagaaac tttatgtcta taacgatggt taccttctga attatgatct ttctgtcttg | 22020 |
| cagaagcccc agtaagctgt ttaggagtta gggtgaaaga gaaaatgttt gttgaaaaaa | 22080 |
| tagtcttctc cacttactta gatatctgca ggggtgtcta aaagtgtgtt cattttgcag | 22140 |
| caatgtttag gtgcatagtt ctaccacact agagatctag gacatttgtc ttgatttggt | 22200 |
| gagttctctt gggaatcatc tgcctcttca ggcgcatttt gcaataaagt ctgtctaggg | 22260 |
| tgggattgtc agaggtctag gggcactgtg ggcctagtga agcctactgt gaggaggctt | 22320 |
| cactagaagc cttaaattag gaattaagga acttaaaact cagtatggcg tctagggatt | 22380 |
| ctttgtacag gaaatattgc ccaatgacta gtcctcatcc atgtagcacc actaattctt | 22440 |
| ccatgcctgg aagaaacctg gggacttagt taggtagatt aatatctgga gctcctcgag | 22500 |
| ggaccaaatc tccaactttt ttttcccctc actagcacct ggaatgatgc tttgtatgtg | 22560 |
| gcagataagt aaatttggca tgcttatata ttctacatct gtaaagtgct gagttttatg | 22620 |
| gagagaggcc ttttatgca ttaaattgta catggcaaat aaatcccaga aggatctgta | 22680 |
| gatgaggcac ctgcttttc ttttctctca ttgtccacct tactaaaagt cagtagaatc | 22740 |
| ttctacctca taacttcctt ccaaaggcag ctcagaagat tagaaccaga cttactaacc | 22800 |
| aattccaccc cccaccaacc cccttctact gcctacttta aaaaaattaa tagttttcta | 22860 |
| tggaactgat ctaagattag aaaaattaat tttctttaat ttcattatga acttttattt | 22920 |
| acatgactct aagactataa gaaaatctga tggcagtgac aaagtgctag catttattgt | 22980 |
| tatctaataa agaccttgga gcatatgtgc aacttatgag tgtatcagtt gttgcatgta | 23040 |
| attttttgcct ttgtttaagc ctggaacttg taagaaaatg aaaatttaat ttttttttct | 23100 |
| aggacgagct atagaaaagc tattgagagt atctagttaa tcagtgcagt agttggaaac | 23160 |
| cttgctggtg tatgtgatgt gcttctgtgc ttttgaatga ctttatcatc tagtctttgt | 23220 |
| ctattttttcc tttgatgttc aagtcctagt ctataggatt ggcagtttaa atgctttact | 23280 |
| ccccctttta aaataaatga ttaaaatgtg ctttgaaaaa agtc | 23324 |

<210> SEQ ID NO 2
<211> LENGTH: 2849
<212> TYPE: DNA
<213> ORGANISM: hGC-1 cCNA

<400> SEQUENCE: 2

| | |
|---|---|
| aagatgaggc ccggcctctc atttctccta gcccttctgt tcttccttgg ccaagctgca | 60 |
| ggggatttgg gggatgtggg acctccaatt cccagccccg gcttcagctc tttcccaggt | 120 |
| gttgactcca gctccagctt cagctccagc tccaggtcgg gctccagctc agccgcagc | 180 |
| ttaggcagcg gaggttctgt gtcccagttg ttttccaatt tcaccggctc cgtggatgac | 240 |

-continued

```
cgtgggacct gccagtgctc tgtttccctg ccagacacca cctttcccgt ggacagagtg     300
gaacgcttgg aattcacagc tcatgttctt tctcagaagt tgagaaaga actttccaaa     360 gtgagggaat atgtccaatt aattagtgtg tatgaaaaga aactgttaaa cctaactgtc     420
cgaattgaca tcatggagaa ggataccatt tcttacactg aactggactt cgagctgatc     480
aaggtagaag tgaaggagat ggaaaaactg gtcatacagc tgaaggagag ttttggtgga     540
agctcagaaa ttgttgacca gctggaggtg gagataagaa atatgactct cttggtagag     600
aagcttgaga cactagacaa aaacaatgtc cttgccattc gccgagaaat cgtggctctg     660
aagaccaagc tgaaagagtg tgaggcctct aaagatcaaa acaccccctgt cgtccaccct     720 cctcccactc cagggagctg tggtcatggt ggtgtggtga acatcagcaa accgtctgtg     780
gttcagctca actggagagg gttttcttat ctatatggtg cttggggtag ggattactct     840
ccccagcatc caaacaaagg actgtattgg gtggcgccat gaatacaga tgggagactg      900 ttggagtatt atagactgta caacacactg gatgatttgc tattgtatat aaatgctcga     960
gagttgcgga tcacctatgg ccaaggtagt ggtacagcag tttacaacaa caacatgtac    1020
gtcaacatgt acaacaccgg gaatattgcc agagttaacc tgaccaccaa cacgattgct    1080
gtgactcaaa ctctccctaa tgctgcctat aataaccgct tttcatatgc taatgttgct    1140
tggcaagata ttgactttgc tgtggatgag aatggattgt gggttattta ttcaactgaa    1200
gccagcactg gtaacatggt gattagtaaa ctcaatgaca ccacacttca ggtgctaaac    1260
acttggtata ccaagcagta taaaccatct gcttctaacg ccttcatggt atgtggggtt    1320
ctgtatgcca cccgtactat gaacaccaga acagaagaga ttttttacta ttatgacaca    1380
aacacaggga agagggcaa actagacatt gtaatgcata agatgcagga aaaagtgcag     1440
agcattaact ataaccctt tgaccagaaa ctttatgtct ataacgatgg ttaccttctg     1500
aattatgatc tttctgtctt gcagaagccc cagtaagctg tttaggagtt agggtgaaag    1560
agaaaatgtt tgttgaaaaa atagtcttct ccacttactt agatatctgc aggggtgtct    1620
aaaagtgtgt tcattttgca gcaatgttta ggtgcatagt tctaccacac tagagatcta    1680
ggacatttgt cttgatttgg tgagttctct tgggaatcat ctgcctcttc aggcgcattt    1740
tgcaataaag tctgtctagg gtgggattgt cagaggtcta gggccacctg tgggcctagt    1800
gaagcctact gtgaggaggc ttcactagaa gccttaaatt aggaattaag gaacttaaaa    1860
ctcagtatgg gcgtctaggg attctttgta caggaaatat tgcccaatga ctagtcctca    1920
tccatgtagc accactaatt cttccatgcc tggaagaaac ctggggactt agttaggtag    1980
attaatatct ggagctcctc gagggaccaa atctccaact ttttttttccc ctcactagca   2040 cctggaatga tgctttgtat gtggcagata agtaaatttg gcatgcttat atattctaca    2100
tctgtaaagt gctgagtttt atggagagag gccttttttat gcattaaatt gtacatggca    2160
aataaatccc agaaggatct gtagatgagg cacctgcttt ttcttttctc tcattgtcca    2220
ccttactaaa agtcagtaga atcttctacc tcataacttc cttccaaagg cagctcagaa    2280
gattagaacc agacttacta accaattcca cccccccacca ccccccttct actgcctact    2340
ttaaaaaaat taatagtttt ctatggaact gatctaagat tagaaaaatt aattttcttt    2400
aatttcatta tgaactttta tttacatgac tctaagacta taagaaaatc tgatggcagt    2460
gacaaagtgc tagcatttat tgttatctaa taaagacctt ggagcatatg tgcaacttat    2520
gagtgtatca gttgttgcat gtaatttttg cctttgttta agcctggaac ttgtaagaaa    2580
atgaaaattt aatttttttt tctaggacga gctatagaaa agctattgag agtatctagt    2640
```

-continued

| | |
|---|---|
| taatcagtgc agtagttgga aaccttgctg gtgtatgtga tgtgcttctg tgcttttgaa | 2700 |
| tgactttatc atctagtctt tgtctatttt tcctttgatg ttcaagtcct agtctatagg | 2760 |
| attggcagtt taaatgcttt actccccctt ttaaaataaa tgattaaaat gtgcttcgaa | 2820 |
| aaaaaaaaaa aaaaaaaaa aaaaaaaaa | 2849 |

<210> SEQ ID NO 3
<211> LENGTH: 2508
<212> TYPE: DNA
<213> ORGANISM: Mouse GC-1 cDNA

<400> SEQUENCE: 3

| | |
|---|---|
| ctcgagcact gttggcctac tggagcatct taacttagaa ggcacgatga gttacagcct | 60 |
| tctctttctc ctggcccttc agttctgcct tggctctgcc tcccggacaa ctctgacctc | 120 |
| tgcacattcc cgggaattga ccacacctcc aacatcaccc caggctacag ctgcctggtt | 180 |
| gcctccggga ggcacttctt gggcagaagg tgggactgtg tctcagccac tttccaattt | 240 |
| cactgggtct gtggacagcc atgggacctg ccagtgttct gtttccctgc cggataccgc | 300 |
| cttccccgct gacagagtgg agcgcttaga gtacacagct cacatccttt ctcagaaatt | 360 |
| cgagagagag ttttctaagg tgaaggagta tgtccagcta ataagtgtgt atgagaagag | 420 |
| gctcctgaac ctgacggtcc gagtagaggt catggagaag acagcatct cttacacaga | 480 |
| actggacttt gagttgatca agctggaagt gaaggagatg caaaaactgg tcttacagct | 540 |
| gaagaagaat tttgttggaa gtacacatat tattgacatg ctcgaagtgg agataaggaa | 600 |
| tatgaccctc ttggtagaga agctggagtc tctagaccaa aacaatgtcc ttagcattcg | 660 |
| ccgccagatc ttggctctga gaccaagct gaaagaatgt gaggcctcca aaagtgacct | 720 |
| tgtgcctgcc acacccctc ctcctgctcc tggaagctgt agtcatggtg gcgtggtgaa | 780 |
| catcagcgct ccttctgtga ttcagctcaa ctggctgggg tttagttata aatatgggtgc | 840 |
| ctggggccga gattactctc ctcagcatcc agagagaacc ctgtactggg tggcacctt | 900 |
| gaatacagat gcaagggctc tagagtatta cagactttac gactcattgg acaatttgtt | 960 |
| aatctattcc cacttccgag actatcggat tcgctatggc caaggaggtg gtacagtagc | 1020 |
| attcaacaac aacctgtatg tgaattggta caatgggggg aacattgcca aaattaatct | 1080 |
| aactaccaat gtagttgatg tgaatcggcc cctccctctg gctgcctaca taatcgctt | 1140 |
| ctcatatgct aatgtgaatt ggcaagacat tgaccttgct gtggatgagc aagcactgtg | 1200 |
| ggcaatttat gcaactgagg ccagcactgg taacatagtg attagtaaac tcaatgacac | 1260 |
| cactcttgag gtgataagca cttgggttac caagcagtac aagccatctg tttcgaatgc | 1320 |
| cttcatggta tgtggagttc tttatgctac tcgcactttg aacaccaaaa cagaagagat | 1380 |
| cttttactat tatgacacaa acacagagag ggaaggcaac ctaggcatca aatgagaaa | 1440 |
| gatgcaggaa agaattcaga gcatcaatta ccatcccttt gaccaagaac tttatgtcta | 1500 |
| taatgatggt tatcttctga actatgatct tgtcttctta cagacgccca ggcaacctgt | 1560 |
| ctaagtgtta gggtgaagga ggaatgaaat gtttgatggc aattttcttc tctacatatt | 1620 |
| tagacagctt cagggaagtc taggagtgtg tttctttagt catgatgtta gtagagatag | 1680 |
| ttttatcaca atagagacct aggctatttg tctcagtttg atttctcttg ggaattatca | 1740 |
| tcctctttgg atagatttaa caaatgaaat aaggtctttg caagtaaagt tctcagcggc | 1800 |
| tagggggtgct atgagcctaa taaagttct agtgaggtaa agtctagaag ataaagaact | 1860 |

```
taaggggtac ttagtatgaa ttctgggaat tctttctctt agaaaatttg catggtgacc    1920
caccacatag aaccattgag ttgtgcatga cagaaaggac gctggggctt aattaggtag    1980
atcaacatca ggaggtggac atgagagcaa atatttagct ttgttttcct cctggctcct    2040
gaaacctgtg tatagcagat aggtaaattt ggcatcttaa atgatatctc tcagacattt    2100
tgagttttt gcagaatgga cctactttat gttaagttgc acagtgcaaa tatgtcctgg    2160
aagggttttc agatgatata cttgggtttt cttttctctc attcttcacc tacacaattc    2220
agtagacccc tttacctcat aattcaggtc ccagggcaac cataagatta gaaacagact    2280
taacaaccag tcacatttct ttactgctta tgtgtttttc ttagacatta actagttttt    2340
ttttttatgg gtcagatata aaatcaatga actttctctt gtattttcct gcaattttgg    2400
tttatgtaat tacaagactg taaaaaaata ccagttgtta gtgatgttgc tggttgcatt    2460
tctagctata taataaagat cgtgaaataa aaaaaaaaaa aggccaca                 2508
```

<210> SEQ ID NO 4
<211> LENGTH: 510
<212> TYPE: PRT
<213> ORGANISM: hGC-1 amino acid sequence

<400> SEQUENCE: 4

```
Met Arg Pro Gly Leu Ser Phe Leu Leu Ala Leu Leu Phe Phe Leu Gly
 1               5                   10                  15

Gln Ala Ala Gly Asp Leu Gly Asp Val Gly Pro Pro Ile Pro Ser Pro
            20                  25                  30

Gly Phe Ser Ser Phe Pro Gly Val Asp Ser Ser Ser Phe Ser Ser
         35                  40                  45

Ser Ser Arg Ser Gly Ser Ser Ser Arg Ser Leu Gly Ser Gly Gly
 50                  55                  60

Ser Val Ser Gln Leu Phe Ser Asn Phe Thr Gly Ser Val Asp Asp Arg
 65                  70                  75                  80

Gly Thr Cys Gln Cys Ser Val Ser Leu Pro Asp Thr Thr Phe Pro Val
                85                  90                  95

Asp Arg Val Glu Arg Leu Glu Phe Thr Ala His Val Leu Ser Gln Lys
            100                 105                 110

Phe Glu Lys Glu Leu Ser Lys Val Arg Glu Tyr Val Gln Leu Ile Ser
        115                 120                 125

Val Tyr Glu Lys Lys Leu Leu Asn Leu Thr Val Arg Ile Asp Ile Met
130                 135                 140

Glu Lys Asp Thr Ile Ser Tyr Thr Glu Leu Asp Phe Glu Leu Ile Lys
145                 150                 155                 160

Val Glu Val Lys Glu Met Glu Lys Leu Val Ile Gln Leu Lys Glu Ser
                165                 170                 175

Phe Gly Gly Ser Ser Glu Ile Val Asp Gln Leu Glu Val Glu Ile Arg
            180                 185                 190

Asn Met Thr Leu Leu Val Glu Lys Leu Glu Thr Leu Asp Lys Asn Asn
        195                 200                 205

Val Leu Ala Ile Arg Arg Glu Ile Val Ala Leu Lys Thr Lys Leu Lys
    210                 215                 220

Glu Cys Glu Ala Ser Lys Asp Gln Asn Thr Pro Val Val His Pro Pro
225                 230                 235                 240

Pro Thr Pro Gly Ser Cys Gly His Gly Gly Val Val Asn Ile Ser Lys
                245                 250                 255

Pro Ser Val Val Gln Leu Asn Trp Arg Gly Phe Ser Tyr Leu Tyr Gly
```

-continued

```
                      260                 265                 270

Ala Trp Gly Arg Asp Tyr Ser Pro Gln His Pro Asn Lys Gly Leu Tyr
            275                 280                 285

Trp Val Ala Pro Leu Asn Thr Asp Gly Arg Leu Leu Glu Tyr Tyr Arg
        290                 295                 300

Leu Tyr Asn Thr Leu Asp Asp Leu Leu Leu Tyr Ile Asn Ala Arg Glu
305                 310                 315                 320

Leu Arg Ile Thr Tyr Gly Gln Gly Ser Gly Thr Ala Val Tyr Asn Asn
                325                 330                 335

Asn Met Tyr Val Asn Met Tyr Asn Thr Gly Asn Ile Ala Arg Val Asn
            340                 345                 350

Leu Thr Thr Asn Thr Ile Ala Val Thr Gln Thr Leu Pro Asn Ala Ala
        355                 360                 365

Tyr Asn Asn Arg Phe Ser Tyr Ala Asn Val Ala Trp Gln Asp Ile Asp
    370                 375                 380

Phe Ala Val Asp Glu Asn Gly Leu Trp Val Ile Tyr Ser Thr Glu Ala
385                 390                 395                 400

Ser Thr Gly Asn Met Val Ile Ser Lys Leu Asn Asp Thr Thr Leu Gln
                405                 410                 415

Val Leu Asn Thr Trp Tyr Thr Lys Gln Tyr Lys Pro Ser Ala Ser Asn
            420                 425                 430

Ala Phe Met Val Cys Gly Val Leu Tyr Ala Thr Arg Thr Met Asn Thr
        435                 440                 445

Arg Thr Glu Glu Ile Phe Tyr Tyr Tyr Asp Thr Asn Thr Gly Lys Glu
    450                 455                 460

Gly Lys Leu Asp Ile Val Met His Lys Met Gln Glu Lys Val Gln Ser
465                 470                 475                 480

Ile Asn Tyr Asn Pro Phe Asp Gln Lys Leu Tyr Val Tyr Asn Asp Gly
                485                 490                 495

Tyr Leu Leu Asn Tyr Asp Leu Ser Val Leu Gln Lys Pro Gln
            500                 505                 510
```

```
<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 5
ctgatggcag tgacaaagtg c                                            21

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 6
tgtagtgtat gtggtcgttc                                              20

<210> SEQ ID NO 7
<211> LENGTH: 26
<212> TYPE: DNA
<213> ORGANISM: Artificial Sequence
<220> FEATURE:
```

```
<223> OTHER INFORMATION: Description of Artificial Sequence; Note =
      synthetic construct

<400> SEQUENCE: 7
ctggccggga cctgactgac tacctc                                              26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 8
aaacaaataa agccatgcca atctca                                              26

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 9
gattactctc cccagcatc                                                      19

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 10
ctctttcacc ctaactcc                                                       18

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 11
gcacatcaca tacaccagca agg                                                 23

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence; Note =
      synthetic construct

<400> SEQUENCE: 12
cagtgcagta gttggaaacc ttgctgg                                             27
```